United States Patent
Aebi et al.

(10) Patent No.: US 6,790,860 B2
(45) Date of Patent: Sep. 14, 2004

(54) PYRROLIDINE DERIVATIVES

(75) Inventors: Johannes Aebi, Basel (CH); Daniel Bur, Therwil (CH); Alexander Chucholowski, San Diego, CA (US); Henrietta Dehmlow, Grenzach-Wyhlen (DE); Eric Argirios Kitas, Arlesheim (CH); Ulrike Obst, Grenzach-Wyhlen (DE); Hans Peter Wessel, Heitersheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/373,622

(22) Filed: Feb. 25, 2003

(65) Prior Publication Data

US 2003/0199569 A1 Oct. 23, 2003

Related U.S. Application Data

(62) Division of application No. 09/906,980, filed on Jul. 17, 2001, now abandoned.

(30) Foreign Application Priority Data

Jul. 19, 2000 (EP) .............................................. 00114949

(51) Int. Cl.[7] ........................ C07D 207/04; A61K 31/40
(52) U.S. Cl. ........................ 514/423; 548/530; 548/539; 548/541; 514/424
(58) Field of Search ................................ 548/541, 542, 548/424, 425

(56) References Cited

FOREIGN PATENT DOCUMENTS

| EP | 0 182 213 | 5/1986 |
|---|---|---|
| EP | 0 333 175 | 9/1989 |
| EP | 0 528 678 | 2/1993 |
| EP | 0 747 381 | 12/1996 |
| WO | WO 97/30046 | 8/1997 |
| WO | WO 98/08814 | 3/1998 |
| WO | WO 98/08815 | 3/1998 |

OTHER PUBLICATIONS

Yanagisawa, M. et al. Nature (Mar. 31, 1998), 332 (6/63), pp. 411–415.
Xu, D., et al., Cell (1994) vol. 78, pp. 473–485.
Oefner, et al., J. Mol. Biol. (2000) 296, pp. 341–349.
Chemical Abstract, "Preparation of 3–pyrrolidinylthio–1–aza–bicyclo '3.2.0' hept–2–ene–2–carboxylic . . . " JP 06 263761 (Fujisawa Pharmaceutical Co., Ltd. JP), Sep. 20, 1994.
Chemical Abstract, "Synthesis and antimicrobial evaluation of 3–(substituted)pyrrolidine cephalosporins", (Yoo, Ji–Seak et al., JP) (1999).

*Primary Examiner*—Joseph K. McKane
*Assistant Examiner*—Golam M M Shameem
(74) *Attorney, Agent, or Firm*—George W. Johnston; John P. Parise

(57) ABSTRACT

The present invention relates to pyrrolidine derivatives useful as inhibitors of metalloproteases, e.g. zinc proteases, and which are effective in treating disease states associated with vasoconstriction.

23 Claims, No Drawings

PYRROLIDINE DERIVATIVES

This application is a divisional of Ser. No. 09/906,980, filed Jul. 17, 2001, now abandoned.

BACKGROUND OF THE INVENTION

Endothelins are peptides that exist in three isoforms, ET-1, ET-2, and ET-3, each encoded by a distinct gene. They have been originally discovered in the conditioned medium of porcine endothelial cells in 1988 by Yanagisawa (Yanagisawa M; Kurihara H; Kimura S; Tomobe Y; Kobayashi M; Mitsui Y; Yazaki Y; Goto K; Masaki T: A novel potent vasoconstrictor peptide produced by vascular endothelial cells [see comments]. NATURE (1988 Mar. 31), 332(6163), 411–5.). The active ETs are peptides of 21 amino acids with two intramolecular disulfide bridges. They are produced from preproproteins of 203 to 212 amino acids, which are processed by furin-like endopeptidases to the biologically inactive big-endothelin (big-ET). The big-ETs are specifically processed to mature ETs by a hydrolytic cleavage between amino acids 21 and 22 that are $Trp^{21}$-$Val^{22}$ (big-ET-1, big ET-2) and $Trp^{21}$-$Ile^{22}$ in big-ET-3 respectively. Already in 1988 a specific metalloprotease was postulated to be responsible for this specific cleavage. In 1994 ECE-1 (endothelin converting enzyme-1) was purified and cloned from bovine adrenal (Xu D, Emoto N, Giaid A, Slaughter C, Kaw S, de Witt D, Yanagisawa M: ECE-1: a membrane-bound metalloprotease that catalyzes the proteolytic activation of big endothelin-1. Cell (1994) 78: 473–485).

ECE-1 is a membrane bound type II zinc-endopeptidase with a neutral pH optimum and a zinc binding motif HExxHx(>20)E. It belongs to subfamily M13 and has a large 681 amino acid ectodomain that comprises the active site. Other members of the M13 family are NEP24.11 (neutral endopeptidase), PEX, a phosphate regulating neutral endopeptidase, and Kell blood group protein that has recently been described as a big-ET-3 processing enzyme. Members of the M13 family of human origin are characterized by a high molecular weight (>80 kDa) a number of conserved disulfide bridges and a complex glycosylation pattern. The structure of NEP has recently been solved. (Oefner et al, J. Mol. Biol. 2000, 296, 341–349). The catalytic domain of ECE and related human M13 proteinases are significantly larger (>650 amino acids) than members of matrix metalloproteases (MMPs). Unlike the family of the MMPs which belong to the metzincins and display a typical HExxHxxGxxH pattern members of the M13 family are gluzincins comprising a HExxHx(>20)E pattern. These two families are clearly different in size of catalytic domains, structure and zinc coordinating pattern of ligands. Active sites of the two families show clear differences which has clear impact on type of inhibitors and the potential selectivity.

SUMMARY OF THE INVENTION

The present invention relates to compounds of formula (I)

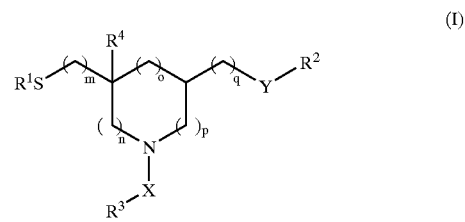

wherein $R^1$ is hydrogen, alkylcarbonyl, or arylcarbonyl;

$R^2$ is alkyl, alkenyl, alkinyl, cyanoalkyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylcarbamoyl, diarylalkyl, aryl(carboxyalkyl)amide, arylamino, arylcarbonyl, arylsulfonyl, cycloalkyl, cycloalkylcarbonyl, cycloalkylalkyl, heteroaryl, heteroarylalkyl, heterocyclylalkyl, or the group $YR^2$ is heterocyclyl or $R^2$ is a group of the formula

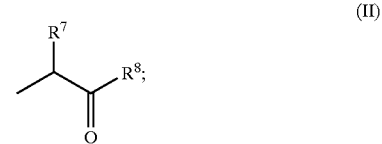

$R^3$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl(alkoxycarbonyl)alkyl, heteroaryl, heteroarylalkyl, heterocyclyl or heterocycylalkyl, and $R^3$ is hydroxy in case of X is $SO_2$;

$R^4$ is hydrogen in case m=1 or alkyl or hydrogen in case m=0;

$R^5$ is hydrogen, alkyl, aryl, or carboxyalkyl;

$R^6$ is hydrogen, alkyl, aryl, carboxyalkyl, arylcarbonyl, alkylcarbonyl, arylalkoxycarbonyl, or arylalkyl;

$R^7$ is hydrogen, aryl, alkyl, arylalkyl, heterocyclylalkyl, arylamino, alkyl(arylalkyl)amino, alkoxycarbonylalkyl, carboxyalkyl, or alkylthioalkyl;

$R^8$ is hydroxy, alkyl, aryl, cyanoalkyl, alkoxy, arylalkyl, arylalkoxy, mono- or dialkylamino, arylamino, aryl(alkyl)amino, cyanoalkylamino, arylalkyl(alkyl)amino, heteroaryl, heteroarylalkyl, or heterocyclyl; and X is —$S(O)_2$—, —$S(O)_2$—NH—, —C(O)—, —C(O)NR$^5$—, C(O)O—;

Y is —$CH_2$—, —O—, —$NR^6$— or —S—;

m and p independently are 0 or 1, n and q independently are 1, 2 or 3 and o is 0, 1 or 2 with the proviso that the sum of n, o and p is $\geq 2$ and $\leq 3$; and dimeric forms, and/or pharmaceutically acceptable esters, and/or pharmaceutically acceptable salts thereof, preferably pharmaceutically acceptable esters, and/or pharmaceutically acceptable salts thereof, and most preferably pharmaceutically acceptable salts thereof.

The present invention is directed to compounds which are useful as inhibitors of metalloproteases, e.g. zinc proteases, particularly zinc hydrolases, and which are effective in the prophylaxis and treatment of disease states which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. In addition the compounds are useful as cytostatic and cerebroprotective agents for inhibition of graft rejection, for organ protection and for treatment of ophthalmological diseases.

DETAILED DESCRIPTION OF THE INVENTION

The present invention is directed to compounds of formula (I):

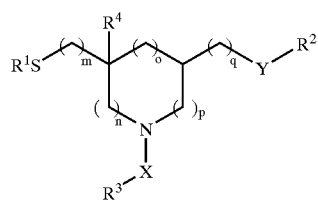

wherein
$R^1$ is hydrogen, alkylcarbonyl, or arylcarbonyl;
$R^2$ is alkyl, alkenyl, alkinyl, cyanoalkyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylcarbamoyl, diarylalkyl, aryl(carboxyalkyl)amide, arylamino, arylcarbonyl, arylsulfonyl, cycloalkyl, cycloalkylcarbonyl, cycloalkylalkyl, heteroaryl, heteroarylalkyl, heterocyclylalkyl, or the group $YR^2$ is heterocyclyl or $R^2$ is a group of the formula

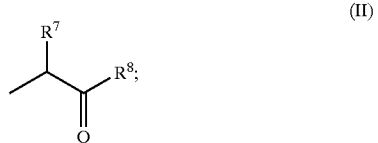

$R^3$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl (alkoxycarbonyl)alkyl, heteroaryl, heteroarylalkyl, heterocyclyl or heterocycylalkyl, and $R^3$ is hydroxy in case of X is $SO_2$;
$R^4$ is hydrogen in case m=1 or alkyl or hydrogen in case m=0;
$R^5$ is hydrogen, alkyl, aryl, or carboxyalkyl;
$R^6$ is hydrogen, alkyl, aryl, carboxyalkyl, arylcarbonyl, alkylcarbonyl, arylalkoxycarbonyl, or arylalkyl;
$R^7$ is hydrogen, aryl, alkyl, arylalkyl, heterocyclylalkyl, arylamino, alkyl(arylalkyl)amino, alkoxycarbonylalkyl, carboxyalkyl, or alkylthioalkyl;
$R^8$ is hydroxy, alkyl, aryl, cyanoalkyl, alkoxy, arylalkyl, arylalkoxy, mono- or dialkylamino, arylamino, aryl (alkyl)amino, cyanoalkylamino, arylalkyl(alkyl)amino, heteroaryl, heteroarylalkyl, or heterocyclyl;
X is $-S(O)_2-$, $-S(O)_2-NH-$, $-C(O)-$, $-C(O)NR^5-$, $C(O)O-$;
Y is $-CH_2-$, $-O-$, $-NR_6-$ or $-S-$;
m and p independently are 0 or 1, n and q independently are 1, 2 or 3 and o is 0, 1 or 2 with the proviso that the sum of n, o and p is $\geq 2$ and $\leq 3$; and
dimeric forms, and/or pharmaceutically acceptable esters, and/or pharmaceutically acceptable salts thereof.

The term "alkyl", alone or in combination, means a straight-chain or branched-chain alkyl group containing a maximum of 7, preferably a maximum of 4, carbon atoms, e.g., methyl, ethyl, n-propyl, 2-methylpropyl (iso-butyl), 1-methylethyl (iso-propyl), n-butyl, and 1,1-dimethylethyl (t-butyl).

The term "carboxy" refers to the group $-C(O)OH$.
The term "carbamoyl" refers to the group $-C(O)NH_2$.
The term "carbonyl" refers to the group $-C(O)-$.
The term "halogen" refers to the group fluoro, bromo, chloro and iodo.
The term "sulfonyl" refers to the group $-S(O_2)-$.
The term "alkenyl" refers to a hydrocarbon chain as defined for alkyl having at least one olefinic double bond (including for example, vinyl, allyl and butenyl).
The term "alkinyl" refers to a hydrocarbon chain as defined for alkyl having at least one olefinic triple bond (including for example propinyl, butin-(1)-yl, etc.
The term "alkoxy", alone or in combination, means an alkyl ether group in which the term 'alkyl' has the significance given earlier, such as methoxy, ethoxy, n-propoxy, isopropoxy, n-butoxy, isobutoxy, sec.butoxy, tert.butoxy and the like.
The term "alkoxycarbonyl" refers to a group of the formula $-C(O)R_c$ wherein $R_c$ is alkoxy as defined above.
The term "hydroxy" refers to the group $-OH$, the term "cyano" to the group $-CN$.
The term "hydroxyalkyl" means an alkyl group as defined above which is substituted by a hydroxy group.
The term "thioalkyl" and "cyanoalkyl" refer to an alkyl group as defined above which is substituted by a $-SH$ group or an $-CN$ group, respectively.
The term "halogenalkyl" refers to an alkyl group as defined above which is substituted by one to three halogen atoms, preferably fluoro, e.g. trifluoromethyl, 2,2,2-trifluoroethyl, etc.
The term "alkylthioalkyl" is a group of the formula alkyl-S-alkyl.
"Carboxyalkyl" means an alkyl as defined above which is substituted by a HOOC-group.
The term "alkylcarbonyl", alone or in combination, means an acyl group derived from an alkanecarboxylic acid, i.e. alkyl-C(O)—, such as acetyl, propionyl, butyryl, valeryl, 4-methylvaleryl etc.
The term "cycloalkyl" signifies a saturated, cyclic hydrocarbon group with 3–8, preferably 3–6 carbon atoms, i.e. cyclopropyl, cyclobutyl, cyclopentyl and cyclohexyl and the like.
The term "amino" refers to the group $-NH_2$.
The term "aryl" for $R^2$—alone or in combination—, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups independently selected from halogen, preferably fluoro, alkoxycarbonyl, e.g. methylcarbonyl, carboxy, cyano, alkyl, alkoxy, phenyl, phenoxy, trifluormethyl, trifluormethoxy, 1,3-dioxolyl, or 1,4-dioxolyl, more preferably fluor, alkoxycarbonyl, alkyl, trifluoromethyl and trifluoromethoxy and most preferably fluor. The most preferred aromatic groups are 2,5-difluorobenzyl and 2,4,5-trifluorobenzyl.

The term "aryl" for $R^3$—alone or in combination—, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups independently selected from halogen, alkoxycarbonyl, e.g. methylcarbonyl, carboxy, cyano, alkyl, alkoxy, phenyl, phenoxy, trifluormethyl, trifluormethoxy, 1,3-dioxolyl, or 1,4-dioxolyl, cyclohexyl, hydroxy, alkylamido, e.g. acetamido, nitro, alkylsulfonyl, e.g. methylsulfonyl, more preferably fluoro, chloro, bromo, alkoxy, carboxy, 1,4-dioxolyl, alkoxycarbonyl. The most preferred aromatic groups are phenyl, 4-fluorobenzyl, 4-carboxybenzyl, 2,3-dihydrobenzo[1,4]dioxihyl, 2-bromophenyl, 2-fluorophenyl, 2-methoxycarbonylphenyl, naphthyl and 4-methoxyphenyl.

The term "aryl" for $R^4$ to $R^{10}$—alone or in combination—refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups independently selected from halogen, preferably fluor, alkoxycarbonyl, e.g. methylcarbonyl, carboxy, cyano, alkyl, alkoxy, phenyl, phenoxy, trifluormethyl, trifluormethoxy, hydroxy, alkylamido, e.g. acetamido, nitro, alkylsulfonyl, e.g. methylsulfonyl, more preferably alkyl or alkoxy.

The term "aryloxy" refers to an aryl group as defined above attached to a parent structure via an oxy radical, i.e., aryl-O—.

The term "heteroaryl" for $R^2$ and $R^4$ to $R^{10}$—alone or in combination—refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, pyridinyl, pyrrolyl, imidazolyl, tetrazolyl, preferably pyridinyl, isoxazolyl or thiazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl.

The term "heteroaryl" for $R^3$—alone or in combination—refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are pyridinyl, thiophenyl, isoxyzolyl, isoquinolyl, quinolyl, and 1H-benzo[d][1,3]oxazin-2,4-dione and indolyl, pyrimidine, pyridazine, and pyrazine, preferably pyridinyl, thiophenyl, isoxazolyl, isoquinolyl, quinolyl, and 1H-benzo[d][1,3]oxazin-2,4-dione and indolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, oxo, alkoxycarbonylalkyl, preferably alkyl.

The term "heterocyclyl"—alone or in combination—refers to a non-aromatic mono- or bicyclic radical having 5 to 10, preferably 5 to 6 ring atoms, containing one to three heteroatoms, preferably one heteroatom, e.g. independently selected from nitrogen, oxygen or sulfur. Optionally the heterocyclic ring can be substituted by a group independently selected from halogen, alkyl, alkoxy, oxocarboxy, alkoxycarbonyl, etc. and/or on a secondary nitrogen atom (i.e. —NH—) by alkyl, arylalkoxycarbonyl, alkylcarbonyl or on a tertiary nitrogen atom (i.e. =N—) by oxido. Examples for heterocyclic groups are morpholinyl, pyrrolidinyl, piperidyl, etc., and especially for $R^2$ alkyl-pyran-triol-yl.

The term "dimeric form" means a compound wherein the two $R^1$ groups of two identical compounds of formula I have been replaced by a common single bond or wherein $R^1$ is glutathione-S— or cysteine-S— or ester and/or alkylcarbonyl or arylcarbonyl derivatives thereof, e.g. acetylcysteine-S— or benzoylcysteine-S—, preferably glutathione-S—, cysteine-S—, acetylcysteine-S— or benzoylcysteine-S—.

The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) are useful in inhibiting mammalian metalloprotease activity, particularly zinc hydrolase activity. More specifically, the compounds of formula (I) are useful as medicaments for the treatment and prophylaxis of disorders which are associated with diseases caused by endothelin-converting enzyme (ECE) activity. Inhibiting of this enzyme would be useful for treating myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma. In addition the compounds are useful as cytostatic and cerebroprotective agents for inhibition of graft rejection, for organ protection and for treatment of ophthalmological diseases.

In a preferred embodiment, the present invention comprises compounds of formula (I) wherein m and p are 0, n, o and q are 1. More specifically, the present invention comprises the above defined compounds of general formula (III).

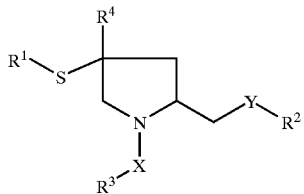

(III)

wherein $R^1$, $R^2$, $R^3$, $R^4$, X and Y are as defined as above.

In a preferred embodiment of the present invention, $R^1$ is hydrogen or alkylcarbonyl, preferably hydrogen or acetyl, and more preferably hydrogen.

In a further preferred embodiment of the present $R^2$ is aryl, arylalkyl, arylalkoxyalkyl, arylcarbamoyl, arylamino, arylcarbonyl, arylsulfonyl, cycloalkyl, cycloalkylcarbonyl, cycloalkylalkyl or heteroarylalkyl, more preferably aryl, arylalkyl, arylcarbamoyl, arylamino, arylcarbonyl, arylsulfonyl or heteroarylalkyl. In the most preferred $R^2$ is arylalkyl and specifically phenylalkyl optionally substituted with 2 to 3 halogen atoms, e.g. 2,4,5-trifluoro-benzyl or 2,5-difluoro-benzyl.

According to the present invention $R^3$ is preferably alkyl, halogenalkyl, alkylcycloalkyl, alkylcycloalkylalkyl, cycloalkyl, halogenalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl (alkoxycarbonyl)alkyl, heteroaryl, heteroarylalkyl or heterocyclyl, more preferably alkyl, arylalkyl, arylcarbonylalkyl, aryloxylakyl, alkylcycloalkyl, alkylcycloylkylalkyl, cycloalkyl, heteroarylalkyl or halogenalkyl and most preferably alkyl, arylalkyl, aryl, aryloxyalkyl or halogenalkyl, e.g. phenoxy-ethyl, 2,2,2-trifluoro-ethyl, 4-fluoro-benzyl, 4-carboxy-benzyl, 2,3-dihydrobenzo[1,4]dioxin-5-yl, 2-bromophenyl, butane-1-yl, methyl, benzyl, tert-butyl, 2-fluoro-phenyl, 4-fluoro-phenyl, 2-methoxy-carbonylphenyl, isopropyl, naphthalen-2-yl, naphthalen-2-yl, or 4-methoxy-phenyl.

In a preferred embodiment $R^4$ is hydrogen.

In the above-defined compounds X is preferably —S(O)$_2$—, —S(O)$_2$—NH—, —C(O)NR$^5$— or C(O)O—, and more preferably —S(O)$_2$—, —C(O)NH— or C(O)O—.

The invention comprises compounds as defined above, wherein $R^5$ is hydrogen, alkyl or carboxyalkyl, preferably hydrogen.

$R^6$ in the compounds described above is preferably hydrogen, alkyl or arylalkyl and more preferably hydrogen.

In further preferred embodiments of the present invention $R^7$ is hydrogen or aryl and $R^8$ is hydroxy or alkoxy.

In the present invention Y preferably is —O— or —NH—.

More specifically the invention comprises the above compounds wherein $R^1$ is hydrogen or alkylcarbonyl, $R^2$ is phenylalkyl substituted with 2 to 3 halogen; $R^3$ is alkyl, aryl, arylalkyl, aryloxyalkyl or halogenalkyl, e.g. e.g. phenoxy-ethyl, 2,2,2-trifluoro-ethyl, 4-fluoro-benzyl, 4-carboxy-benzyl, 2,3-dihydrobenzo[1,4]dioxin-5-yl, 2-bromophenyl, butane-1-yl, methyl, benzyl, tert-butyl, 2-fluoro-phenyl, 4-fluoro-phenyl, 2-methoxy-carbonylphenyl, isopropyl, naphthalen-2-yl, naphthalen-2-yl, or 4-methoxy-phenyl;
X is —SO$_2$—, —CONH—, —C(O)—O—; and Y is —NH— or —O—.

The present invention comprises compounds as defined above with the stereochemistry shown in formula (IV)

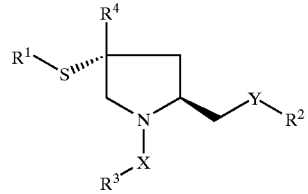

(IV)

wherein $R^1$, $R^2$, $R^3$, $R^4$, X and Y are as defined above.

In the most preferred embodiment the invention comprises compounds of formula (IV) wherein $R^1$ is hydrogen or acetyl and $R^2$ is difluorobenzyl or trifluorobenzyl, e.g. 2,4,5-trifluoro-benzyl or 2,5-difluoro-benzyl- and $R^3$ is phenoxy-ethyl, 2,2,2-trifluoro-ethyl, 4-fluoro-benzyl, 4-carboxy-benzyl, 2,3-dihydrobenzo[1,4]dioxin-5-yl, 2-bromophenyl, butane-1-yl, methyl, benzyl, tert-butyl, 2-fluoro-phenyl, 4-fluoro-phenyl, 2-methoxy-carbonylphenyl, isopropyl, naphthalen-2-yl, naphthalen-2-yl, or 4-methoxy-phenyl and $R^4$ is hydrogen, X is —S(O)$_2$—, —C(O)NH— or C(O)O— and Y is —O— or —NH—.

Preferred embodiments of the present invention are the compounds exemplified in the examples. Especially, the invention comprises the following compounds selected from the group consisting of a) (3R,5S)-5-[(2,5-Difluoro-benzylamino)-methyl]-1-(naphthalene-2-sulfonyl)pyrrolidine-3-thiol;

b) (2S,4R)-2-[(2,5-Difluoro-benzylamino)-methyl]-4-mercapto-pyrrolidine-1-carboxylic acid (2-fluoro-phenyl)-amide;

c) (2S,4R)-2-[(2,5-Difluoro-benzylamino)-methyl]-4-mercapto-pyrrolidine-1-carboxylic acid 4-methoxy-phenyl ester;

d) (2S,4R)-2-[(2,5-Difluoro-benzylamino)-methyl]-4-mercapto-pyrrolidine-1-carboxylic acid 4-fluoro-phenyl ester;

e) 2S,4R)-2-[(2,5-Difluoro-benzylamino)-methyl]-4-mercapto-pyrrolidine-1-carboxylic acid isopropyl ester;

f) (2S,4R)-2-[(2,5-Difluoro-benzylamino)-methyl]-4-mercapto-pyrrolidine-1-carboxylic acid naphthalen-2-yl ester;

g) (2S,4R)-2-[(2,5-Difluoro-benzylamino)-methyl]-4-mercapto-pyrrolidine-1-carboxylic acid 2,3-dihydro-benzo [1,4]dioxin-5-yl ester;

h) (2S,4R)-2-[(2,5-Difluoro-benzylamino)-methyl]-4-mercapto-pyrrolidine-1-carboxylic acid butyl ester;

i) (2S,4R)-4-Mercapto-2-(2,4,5-trifluoro-benzyloxymethyl)-pyrrolidine-1-carboxylic acid isopropyl ester;

j) (2S,4R)-4-Mercapto-2-(2,4,5-trifluoro-benzyloxymethyl)-pyrrolidine-1-carboxylic acid 2,3-dihydro-benzo[1,4]dioxin-5-yl ester;

k) (2S,4R)-4-Mercapto-2-(2,4,5-trifluoro-benzyloxymethyl)-pyrrolidine-1-carboxylic acid tert-butyl ester;

l) (2S,4R)-4-Mercapto-2-(2,4,5-trifluoro-benzyloxymethyl)-pyrrolidine-1-carboxylic acid butyl ester;

m) (2S,4R)-4-Mercapto-2-(2,4,5-trifluoro-benzyloxymethyl)-pyrrolidine-1-carboxylic acid 2-fluoro-phenyl ester;

n) (2S,4R)-4-Mercapto-2-(2,4,5-trifluoro-benzyloxymethyl)-pyrrolidine-1-carboxylic acid 2-methoxycarbonyl-phenyl ester;

o) (2S,4R)-4-Mercapto-2-(2,4,5-trifluoro-benzyloxymethyl)-pyrrolidine-1-carboxylic acid 2-bromo-phenyl ester;

p) (3R,5S)-1-(Butane-1-sulfonyl)-5-(2,4,5-trifluoro-benzyloxymethyl)-pyrrolidine-3-thiol;

q) (3R,5S)-1-Methanesulfonyl-5-(2,4,5-trifluoro-benzyloxymethyl)-pyrrolidine-3-thiol;

r) (2S,4R)-4-Mercapto-2-(2,4,5-trifluoro-benzyloxymethyl)-pyrrolidine-1-sulfonic acid benzylamide;

s) 4-Mercapto-2-(2,4,5-trifluoro-benzyloxymethyl)-pyrrolidine-1-sulfonic acid butylamide;

t) 4-Mercapto-2-(2,4,5-trifluoro-benzyloxymethyl)-pyrrolidine-1-sulfonic acid (2-phenoxy-ethyl)-amide;

u) 4-Mercapto-2-(2,4,5-trifluoro-benzyloxymethyl)-pyrrolidine-1-sulfonic acid (2,2,2-trifluoro-ethyl)-amide;

v) 4-Mercapto-2-(2,4,5-trifluoro-benzyloxymethyl)-pyrrolidine-1-sulfonic acid 4-fluoro-benzylamide;

w) 4-{[4-Mercapto-2-(2,4,5-trifluoro-benzyloxymethyl)-pyrrolidine-1-sulfonylamino]-methyl}-benzoic acid;

x) (2S,4R)-4-Acetylsulfanyl-2-(2,4,5-trifluoro-benzyloxymethyl)-pyrrolidine-1-carboxylic acid 2,3-dihydro-benzo [1,4]dioxin-5-yl ester;

y) (2S,4R)-4-Acetylsulfanyl-2-[(2,5-difluoro-benzylamino)-methyl]-pyrrolidine-1-carboxylic acid butyl ester; and z) (2S,4R)-4-Acetylsulfanyl-2-(2,4,5-trifluoro-benzyloxymethyl)-pyrrolidine-1-carboxylic acid 2-methoxycarbonyl-phenyl ester.

These compounds show activity values of 0.5 nM to 100 nM in the radioimmunoassay (E and F), see below.

The invention also refers to pharmaceutical compositions containing a compound as defined above and a pharmaceutically acceptable excipient.

A further embodiment of the present invention refers to the use of compounds as defined above as active ingredients in the manufacture of medicaments comprising a compound as defined above for the prophylaxis and treatment of disorders which are caused by endothelin-converting enzyme (ECE) activity especially myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

Further the invention refers to the use of compounds as described above for the treatment or prophylaxis of diseases which are associated with myocardial ischaemia, congestive head failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

In addition the invention comprises compounds as described above for use as therapeutic active substances, in particular in context with diseases which are associated with zinc hydrolase activity such as myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

The invention also comprises a method for the therapeutic and/or prophylactic treatment of myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gas trointestinal disorders, endotoxic shock and septicaemia, and for wound healing and control of menstruation, glaucoma, graft rejection, diseases associated withcytostatic, ophthalmological, and cerebroprotective indications, and organ protection, which method comprises administering a compound as defined above to a human being or animal.

The invention also relates to the use of compounds as defined above for the inhibition of zinc hydrolase activity.

The invention also refers to the above compounds whenever manufactured by a process as described below.

Compounds of formula (I) can be prepared by methods known in the art or as described below. Unless otherwise indicated, the substituents $R^1$, $R^2$, $R^3$, $R^4$, $R^5$, $R^6$, $R^7$, $R^8$, X, Y, m, p, n, q are as described above.

Step a) of scheme I describes the persilylation of hydroxy- and amino groups, e.g. by reaction of compound 1 with hexamethyldisilazan/140° C. followed by reaction with $R^3SO_2Cl$ in THF or di-t-butyldicarbonate/$NaHCO_3$ in dioxane/$H_2O$ (BOC protection). For inversion of the configuration (via mesylate) the resulting alcohol 2 is treated with $MeSO_3H/Ph_3P/DIAD$ in toluene (room temperature to 80° C.) or (via bromide) with $LiBr/DEAD/Ph_3P$ in THF (4° C. to room temperature) or (via chloride) with $Ph_3P/CCl_4$ in $CH_2Cl_2$ (3° C. to room temperature). In case of retention of the configuration (via mesylate) alcohol 2 can be transformed to a compound of formula 3 by reaction with $MeSO_2Cl$/pyridine/DMAP (0° C. to room temperature).

For the introduction of a protected thio moiety, e.g. triphenylmethanethiol or 4-methoxy-benzylmercaptane, compound of formula 3 are treated with K—Ot—Bu in DMF (for Br: 0° C. to room temperature; for Cl: 0° C.; for Mes: room temperature to 100° C. For step d the corresponding compounds of formula 4, 8 and 9 can be obtained according to methods known in the art, e.g. LAH in THF at −20° C. or Red-Al in Toluene/THF at −50° C.

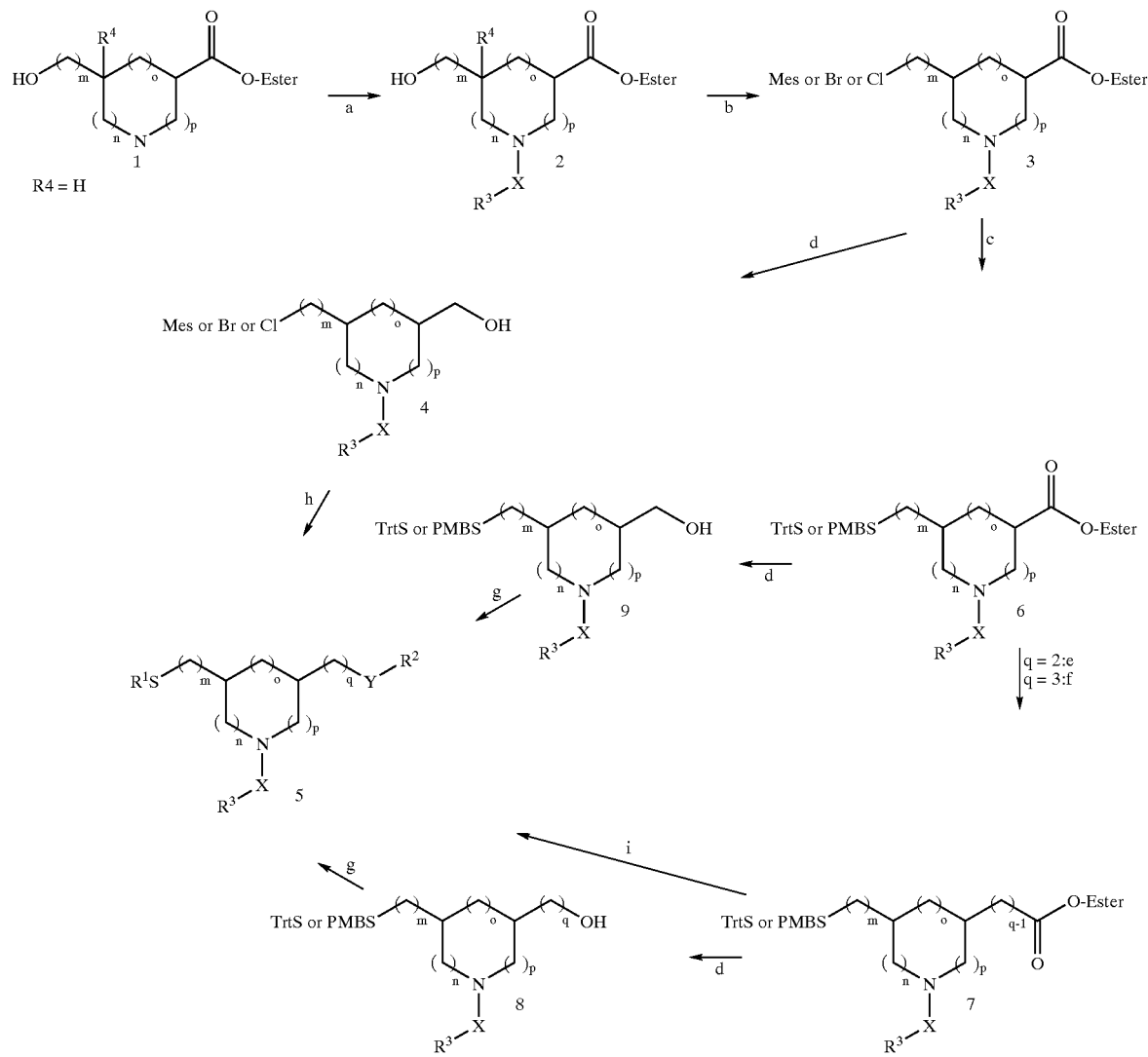

SCHEME 1

For the reaction of compound 6 to compound 7 the Arndt-Eistert reaction may be used (in case q=2: hydrolysis with NaOH in EtOH at room temperature followed by addition of $(COCl)_2$, cat DMF in $CH_2Cl_2$ at 0° C. to room temperature to give the corresponding acid chloride followed by reaction with trimethylsilyldiazomethane in THF/$CH_3CN$ at 0° C. to room temperature to give the corresponding diazoethanone and rearrangement to the methylester with silver benzoate in MeOH/THF at −25° C. to room temperature gave 7). For q=3 compounds of formula 6 are hydrolyzed (NaOH in EtOH at room temperature), followed by formation of the corresponding Weinreb amide (e.g. $HCl.H_2NOMe$/NMM, EDCI, HOBT) and conversion to an aldehyde (LAH, −78 to −30° C. in THF). The obtained compound can be converted by a Horner-Emmons reaction (e.g. $(EtO)_2P(=O)CH_2COOEt$, NaH in THF) followed by reduction of the double bond and reduction of the ester (a) Mg in MeOH, (b) LAH in THF at −20° C.) and BOC replacement (e.g. (a) TFA in $CH_2Cl_2$−20° C. to room temperature, (b) $NaHCO_3$/EtOAc, (c) $ClCOOR^3/Et_3N$ or conversion to all other $R^3X$ described later).

For the introduction of Y=$NR^2$, $SR^2$ or a N-heterocycle (step g) a compound of formula 8 or 9 may be mesylated (1.1 eq $MeSO_2$ Cl/1.5 pyridine/1 eq DMAP; in case Y is an amine the reaction is performed with e.g. 1 eq NaI, amine neat 100° C., for Y $R^2$ is pyrrole, imidazole or X is S, the reaction is performed with 1 eq NaI, NaH in DMF at 0° C. to room temperature, followed by thiol deprotection, e.g. by treatment with $TFA/Et_3SiH$, 0° C. to room temperature ($R^1$ is Trt) or $TFA/Et_3SiH$, 0 to 80° C. ($R^1$ is PMB). An alternative method for the introduction of Y=$NR^2$ would comprise the reaction of compound 8 or 9 with 1.1 eq $MeSO_2Cl$/1.5 eq pyridine/1 eq DMAP (mesylation) followed by treatment with $NaN_3$, DMF for 16 hours at 80° C. to obtain the azide. This compound is then converted to the Y=$NR^2$ (=amines or triazoles) after the introduction of new $R^3X$.

For the introduction of a new $R^3X$ in case $R^3X$ is BOC, the azide may be BOC deprotected by reaction with TFA, $CH_2Cl_2$ at −20° C. to room temperature, followed by reaction with $ClCO_2R^3$, $iPr_2NEt$, $CH_2Cl_2$ or $R^3NCO$ in THF at 0° C. to room temperature (or conversion to all other $R^3X$ described later), followed by reduction of the azide (e.g. $Ph_3P$, THF, $H_2O$ or $NaBH_4$, MeOH), followed by reductive amination (e.g. aldehyde, $SnCl_2$, $NaBH_3CN$, MeOH). In case $R^6$ has to be introduced the compound is treated with $R^6Br/K_2CO_3$ in acetonitrile at room temperature followed by thiol deprotection (e.g. $Et_3SiH$, TFA, 0° C. to room temperature or $Et_3SiH$, TFA, MeCN at room temperature or, for selective trityl-thiol deprotection in the presence of BOC by for example treatment with $iPr_3SiH$ in $TFA/CH_2Cl_2$, 0° C. to room temperature).

A further method for the introduction of new substituents $YR^2$ and $XR^3$ comprises the oxidation of an alcohol 8 or 9 to the aldehyde (e.g. with $(COCl)_2/DMSO/iPr_2NEt$ at −65° C. to room temperature in $CH_2Cl_2$), an imine formation (e.g. corresponding primary amine/$MgSO_4$, room temperature, 16 hours in $CH_2Cl_2$), reduction to the amine (e.g. $NaBH_4$ in MeOH at 40° C., FMOC-protection of Y=$NHR^2$ (e.g. FMOC-Cl/$iPr_2NEt$/cat DMAP, 0° C. to room temperature), BOC-deprotection (e.g. TFA in $CH_2Cl_2$, 0° C. to room temperature), followed by reaction with $R^3NHSO_2Cl$ (in e.g. $iPr_2NEt$, 0° C. to room temperature) (or conversion to all other $R^3X$ described later), FMOC-deprotection (e.g. $Et_2NH$ in THF), and thiol deprotection (e.g. $Et_3SiH$ in TFA at 80° C.).

Compounds wherein $YR^2$ is triazol may be prepared via step g by reaction of the above mentioned azide with the corresponding alkyl/amine$COCH_2$ keton/ester/amide/aryl and $K_2CO_3$ (in DMSO, 40° C. for 3 days) followed by thiol deprotection (e.g. $Et_3SiH$, TFA, 0° C. to room temperature or $Et_3SiH$, TFA, MeCN, room temperature). An alternative is the reaction of the corresponding azide with alkyl/amine$COCH_2$ ester, $K_2CO_3$, DMSO, 40° C. for 3 days, followed by hydrolysis of the ester(e.g. LiOH, THF) and thiol deprotection as described above.

In case of an introduction of a new substituent $R^3X$ in case $R^3X$ is BOC, the corresponding compound may be prepared via step g by BOC deprotection (TFA, $CH_2Cl_2$, −20° C. to room temperature), followed by reaction with a compound of formula $R^3OCOCl$ and $iPr_2NEt/CH_2Cl_2$ or conversion to all other $R^3X$ described later.

In case $YR^2$ represents a phenolether the phenol may be introduced via step g under Mitsunobu conditions (e.g. DEAD/$Ph_3P$/PhOH in THF) and in case $R^1$ is Trt followed by reaction with e.g. $TFA/Et_3SiH$ at 0° C. to room temperature or, in case $R^1$ is PMB, followed by reaction with e.g. $TFA/Et_3SiH$, at 0 to 80° C. In case $YR^2$ represents carbamates, the corresponding compounds 5 may by obtained via step g by reaction with isocyanate/NMM in toluene at room temperature followed optionally by reaction with the corresponding alkyl-, cycloalkyl-halogenide, alkylbromoacetate with NaH in DMF at 0° C. to room temperature. If $YR^2$ represents an ether the corresponding compounds 5 may be obtained via step g by O-alkylation (e.g. NaH, $R^2$-halogenide, DMF 0° C. to room temperature) or by O-alkylation with phase transfer conditions (e.g. $R^2$-halogenide/50% NaOH, $Bu_4NHSO_4$). This reaction may be followed by reaction with e.g. $TFA/Et_3SiH$ at 0° C. to room temperature ($R^1$ is Trt) or, in case $R^3$ is PMB, followed by reaction with e.g. $TFA/Et_3SiH$, at 0 to 80° C.

Compounds containing a group of formula (II) may be prepared via step g by reaction of the corresponding starting compound 8 or 9 with NaH, $R^2$-halogenide/NaI, DMF and in case $R^2$ contains a COOtBu (a) reaction with TFA in $CH_2Cl_2$ at −20° C. and (b) reaction with EDCI/HOBT amine in $CH_2Cl_2$ for formation of the corresponding amide—or, in case $R^2$ contains a COO-alkyl- (a) reaction with 1N NaOH in THF/EtOH to give the acid. Both pathways are completed by reaction with $Et_3SiH$ in TFA at 0° C. to room temperature.

Compounds wherein $YR^2$ is an ether the group $R^3X$ may be varied as followed: For O-alkylation compounds of formula 8 or 9 may be reacted with e.g. NaH/reactive $R^2Br$ in DMF at 0° C. to room temperature followed be BOC deprotection (e.g. TFA in $CH_2Cl_2$ at −20° C. to room temperature to get the amine as starting material.

In case $R^3X$ is a carbamate these starting compounds may be reacted with $R^3OCOCl$/pyridine in THF or by reaction with (a) $R^3OH/Cl_3COCl$/quinoline (formation of the chloroformate) followed by reaction with NaH. In case $R^3X$ is a sulfonamide the starting compounds may be reacted with $R^3SO_2Cl/(i-Pr)_2EtN$/cat DMAP in $ClCH_2CH_2Cl$ at room temperature. In case $R^3X$ is urea the starting compounds may be reacted with isocyanate in EtOH at room temperature. In case $R^3X$ is an alkylated urea, (i.e. introduction of $R^5$) the starting compounds may be reacted with isocyanate in EtOH at room temperature followed by reaction with the corresponding alkylhalogenide/K—OtBu at 0° C. to room temperature. In case $R^3X$ is an amide, the starting compounds may be reacted with RCOOH/EDCI/DMAP (with anhydride formation, and subsequent addition of the starting amine, −10° C. to room temperature) or as alternative with RCOOH/EDCI/DMAP at room temperature. In case $R^3X$ is a sulfamide (for $R^3$ is $NH_2$) the starting compounds may be reacted with sulfamic acid 2,4,6-trichlorophenylester/$Et_3N$ in $CH_2Cl_2$ at 40° C. or with other methods which are known in the art. In case $R^3X$ is $SO_2OH$ the starting compounds may be reacted with chlorosuphonic acid/2-picoline. In case $R^3X$ is an alkylated sulfamide (i.e. introduction of $R^5$) the starting compounds may be reacted with NaH/alkyl halide in DMF at 0° C. at room temperature. Thiol liberation can than be achieved by reaction in TFA/$Et_3SiH$ at room temperature.

Step h of scheme 1 includes a reaction pathway for the preparation of further derivatives by reaction of compounds of formula 4 with (a) NaH/reactive $R^2Br$ in DMF at 0° C. to room temperature followed by (b) reaction with KSAc in DMF at 100° C. The corresponding thiols could be obtained by reaction of the the above compounds with LiOH aqueous in EtOH at 0° C. to room temperature.

Step i of scheme 1 shows the preparation of compounds of formula 5 wherein Y is C. Compounds of formula 4 are treated with NaOH in EtOH at room temperature, followed by formation of a Weinreb amide (e.g. by reaction with $HCl.H_2NOMe$/NMM, EDCI, HOBT at 0° C. to room temperature), followed by formation of the corresponding ketone (e.g. by reaction with $R^2$—MgBr in THF, at 0° C. to room temperature), BOC deprotection (e.g. TFA in $CH_2Cl_2$, at −20° C. to room temperature) followed by reaction with $R^3OCOCl$/NMM in $CH_2Cl_2$ (or conversion to all other $R^3X$ described before) and reduction of the ketone to the methylene and thiol deprotection (e.g. $Et_3SiH$ in TFA at 80° C. for 18 hours).

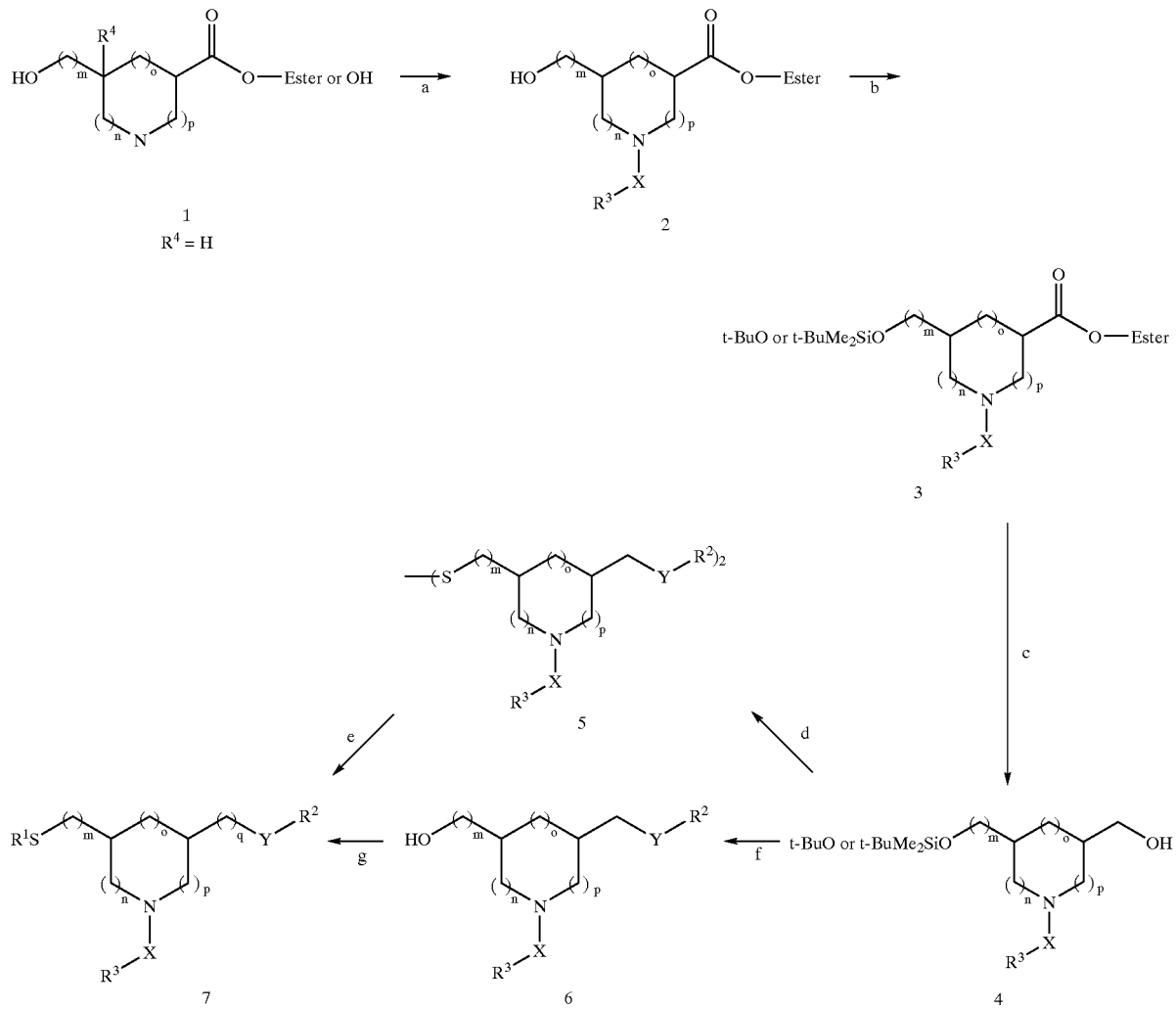

SCHEME 2

Further reaction pathways are shown in scheme 2: Compounds of formula 2 may be obtained by persilylation of the hydroxy- and amino groups of compounds 1 (e.g. reaction with HMDS, neat 120° C.) and preparation of the corresponding methyl ester (step a) (e.g. $R^3SO_2Cl$, $iPr_2NEt$, THF, if acid, then e.g. MeOH, HCl). Step b of scheme 2 shows the formation of the corresponding t-Butyldimethylsilylether or for example the t-butylether (e.g. by reaction with TBDMSCl/DBU in $CH_3CN$ at 0° C. to room temperature, or by reaction with isobutylene, $BF_3.OEt_2$ in $CH_2Cl_2$ at −30 to −20° C. Step c comprises the reaction of compound 2 with $LiBH_4$ in THF at −20° C. to room temperature or LAH at −15° C. in ether to obtain compounds 4.

In case $R^2Y$ is $R^2N$, step d of scheme 2 shows the introduction of a phthalimide under Mitsunobu conditions (e.g. phthalimide, DEAD/Ph$_3$P in THF, 3 to 80° C. This may be followed by t-butyldimethylsilylether deprotection (e.g. for t-BuMe$_2$Si: reaction with TBAF in THF at room temperature), followed by reaction with e.g. MeSO$_3$H/DIAD/Ph$_3$P in toluene at room temperature −80° C., followed by e.g. reaction with KSCOCH$_3$ in DMF at 100° C., followed by phthalimide deprotection and disulfide formation (e.g. by reaction with CH$_3$NH$_2$, EtOH for 2 days at room temperature which may be followed by reaction with R$^2$SO$_2$Cl or R$^2$COCl, DMAP in CH$_2$Cl$_2$ or R$^2$CO$_2$H, TPTU or N-alkylation by reaction with R$^2$Br and N-methylmorpholine in CH$_2$Cl$_2$. This may be followed by side chain manipulation e.g. hydrolysis with LiOH in THF/H$_2$O. Step e of scheme 2 shows the reduction of the disulfide to the thiol (e.g. by nBu$_3$P/CF$_3$CH$_2$OH/H$_2$O at 0° C. or DTT, 2 M K$_2$CO$_3$, MeCN).

In case $R^2Y$ is $R^2O$: Compounds of this type may be obtained by reaction shown in step f and g. These reaction may comprise (step f) reaction of compounds 4 with R$^2$Br/NaH in DMSO at room temperature or benzyl-2,2,2-trichloroacetimidate/CF$_3$SO$_3$H in CH$_2$Cl$_2$/cyclohexane at room temperature (here the R$^2$-side chains may be manipulated by reaction with 10% Pd/C/H$_2$ in EtOH/dioxane) or the reaction is performed with PhOH/Ph$_3$P/DIAD in THF at room temperature. All reactions may be followed by removal of the t-Bu-ether in TFA at 0° C. to room temperature. For the preparation of compounds of formula 7 (step g) compounds 6 (if m=0: for inversion of the configuration) may be obtained by thioacetate formation under Mitsunobu conditions (e.g. CH$_3$COSH/Ph$_3$P/DIAD in THF at 0° C. to room temperature) followed by formation of the thiol (e.g. by reaction with MeONa in MeOH at 0° C.; plus potential side chain manipulation with 1 N Na$_2$CO$_3$ in MeOH) or (if m=0: for retention of configuration) reaction of compounds 6 for e.g. formation of the mesylate (MeSO$_3$H/Et$_3$N/Ph$_3$P/DIAD in toluene at 0° C. to 85° C.) followed by preparation of the thioacetate (e.g. KSCOCH$_3$ in DMF at 100° C.) and formation of the thiol (MeONa in MeOH at 0° C.).

Scheme 3 shows a further route for the preparation of compounds of formula (I). Step a comprises the preparation of compounds 2 by reaction of compounds 1 with e.g. R$^3$SO$_2$Cl/DMAP in CH$_2$Cl$_2$ at room temperature or Et$_3$N in CH$_2$Cl$_2$ (reflux)) followed by monohydrolysis (e.g. 1 M NaOH in MeOH/H$_2$O for 20 min reflux and reduction of the acid with e.g. BH$_3$.THF in THF at 0° C. Step c shows an alkylation (e.g. with R$^2$Br/NaH in DMSO at room temperature) followed by ester reduction (e.g. LAH at −15° C. in ether). Step e comprises the formation of the thioacetate (e.g. by CH$_3$COSH/Ph$_3$P/DIAD in THF at 0° C. to room temperature followed by formation of the thiol (e.g. with MeONa in MeOH at 0° C. Step f shows the reduction of both esters (e.g. with LAH in THF at 0° C.) followed by monoalkylation (e.g. with R$^2$Br/NaH in DMF at −15° C., step g). This pathway may be continued by formation of the mesylate (e.g. with MeSO$_2$Cl/Et$_3$N in Et$_2$O at −20° C. to room temperature), formation of the thioacetate (e.g. with KSCOCH$_3$ in DMF at 100° C.) and formation of the thiol (LAH in Et$_2$O reflux). Step h depicts an additional way for preparing a mono-p-tosylate (e.g. with p-TosCl/Et$_3$N/cat DMAP in THF at room temperature) followed by introduction of the tritylthiolate (e.g. with Ph$_3$CSH/KOt—Bu in DMF at room temperature), formation of the mesylate (step i, with MeSO$_2$Cl/Et$_3$N in THF at 0° C. to room temperature) followed by the formation of the phenolether (e.g. with PhOH/NaH in DMF at room temperature) or alternatively alkylation of the alcohol directly with R$^2$Br/NaH in DMF at −15° C. to room temperature and finally formation of the thiol (e.g. with Et$_3$SiH in TFA at 0° C. to room temperature).

SCHEME 3

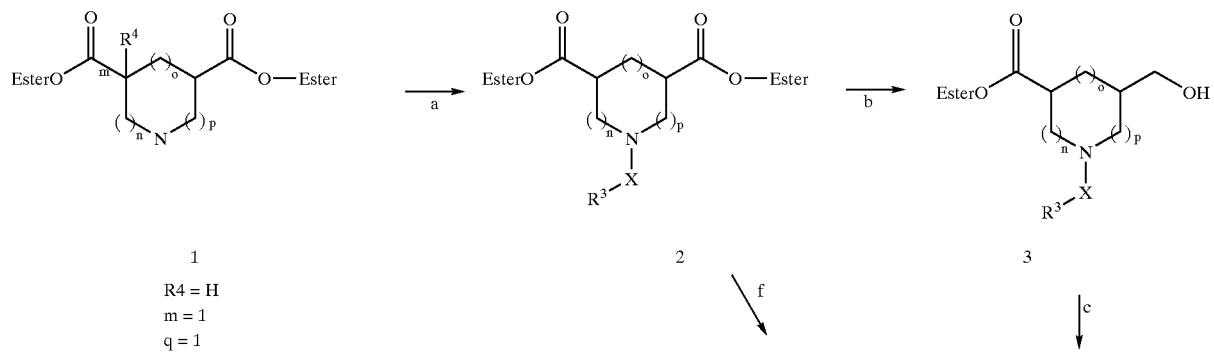

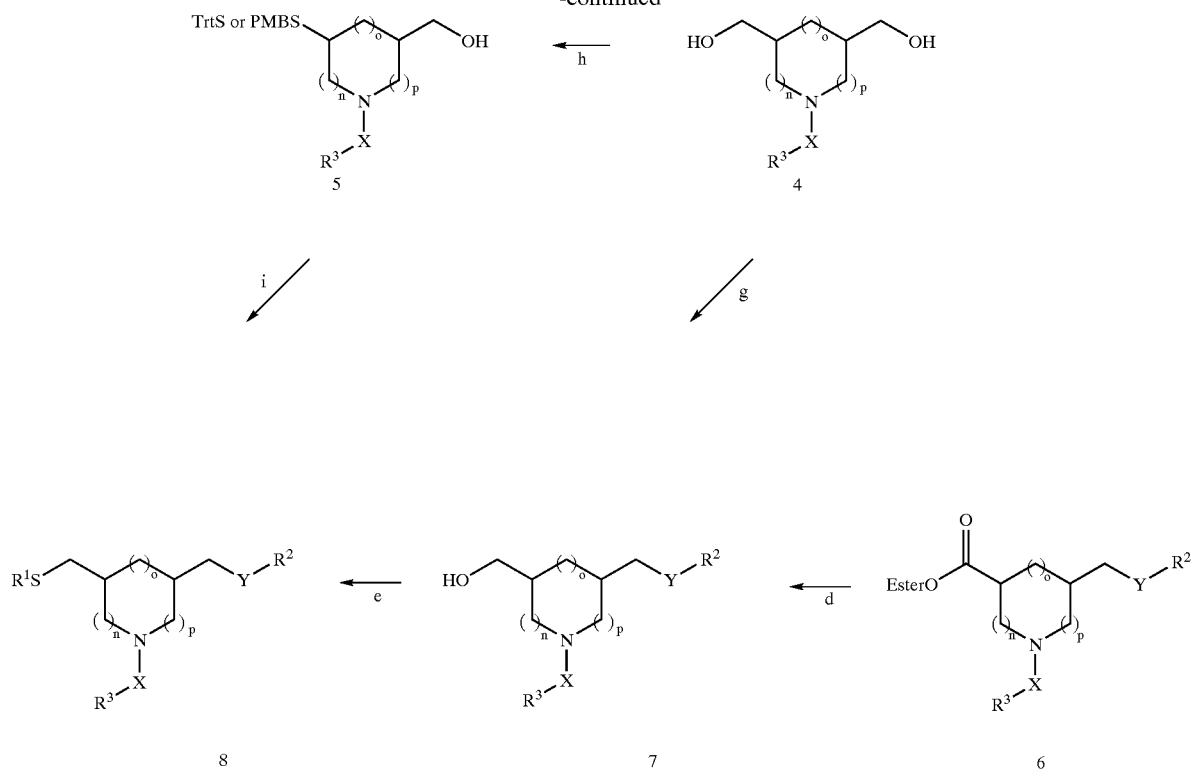

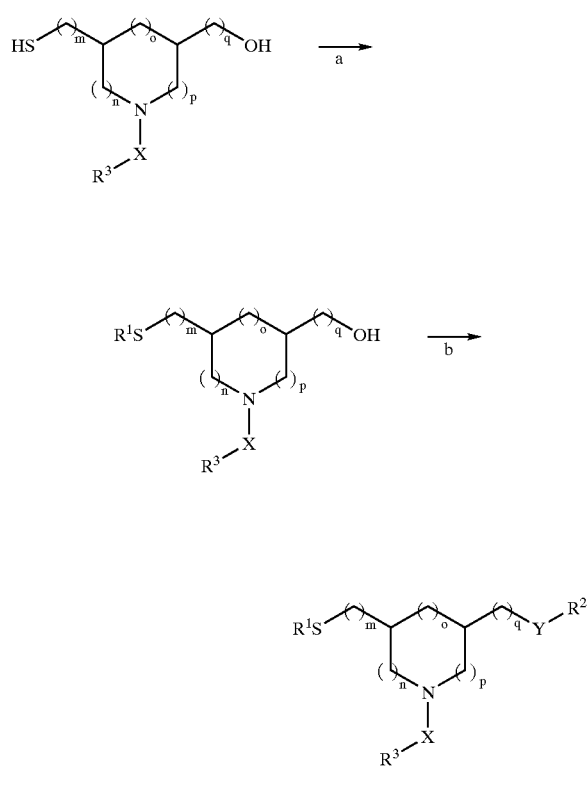

SCHEME 4

Scheme 4 shows in step a the selective protection of the thiol group (e.g. by reaction with $Ac_2O$/pyridine in $CH_2Cl_2$ at room temperature; the starting compound can be received by a deprotection of a STrt or SPMB protected alcohol described above, e.g. $Et_3SiH$ in TFA). The S-acetylated alcohol was then reacted with (a) 1,2,3,4-tetra-O-acetyl-t-deoxy-beta-L-mannospyranose/trimethylsilyl-trifluoromethanesulphonate in $CH_2Cl_2$ at 0° C. followed by cleavage of all acetyl group with NaOMe in MeOH at 0° C.

Scheme 5 shows the reaction pathway for the synthesis of sterically hindered thiols. Step a represents a Swern-oxidation of the starting material which is known in the art (e.g. $(COCl)_2$/DMSO/Et(i-Pr)$_2$N in $CH_2Cl_2$). Step b shows the methylene introduction by a Wittig reaction (e.g. with Kt—BuO/$CH_3PPh_3Br$ in THF at room temperature to 70° C. Step c shows a reduction via a mixed anhydride (e.g. with iBuOCOCl/NMM in THF at −5° C. to room temperature, then the mixture is added to $NaBH_4$ in water at 0° C. and warmed up to room temperature) followed by alkylation of the corresponding alcohol (e.g. with NaH/$R^2$Br in THF at 0° C. to room temperature). Step d represents the formation of an epoxide (e.g. with mCPBA in $CH_2Cl_2$ at room temperature) followed by the formation of a thiirane (e.g. with KSCN in EtOH/$H_2O$ at room temperature or $PO(OMe)_2$ SCl in $CH_2Cl_2$). The resulting diastereomers are separable with methods known in the art. Step e shows the opening of the thiirane (e.g. with $LiHBEt_3$ in THF and LAH) and reduction of the resulting disulfide (e.g. with $P(Bu)_3$/$H_2O$ in trifluoroethanol/$CH_2Cl_2$).

SCHEME 5

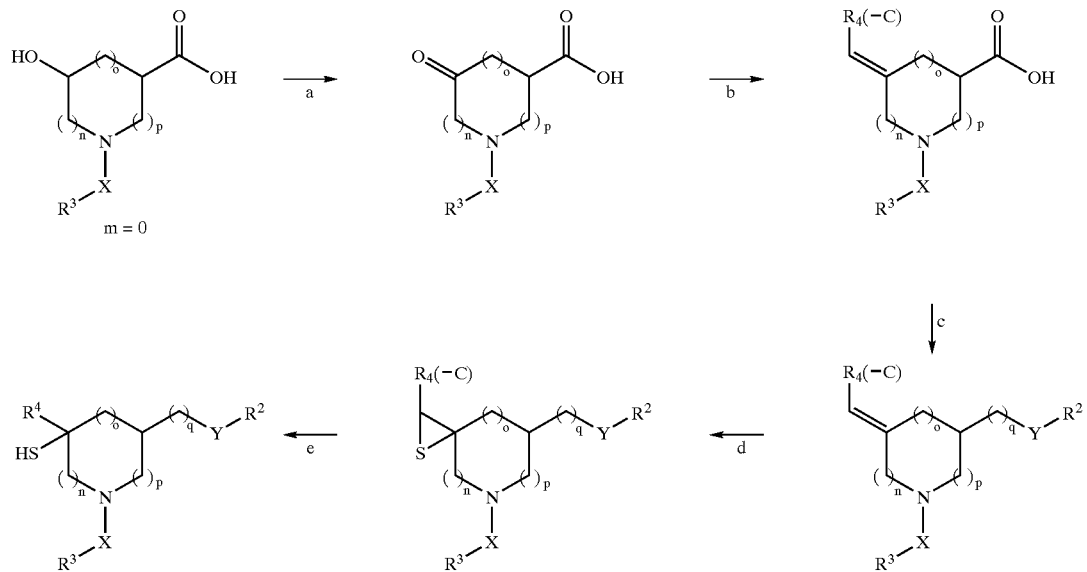

Scheme 6 shows the synthesis of further derivatives: for Y being NH: Step a comprises the N-acylation (protection of NH, e.g. with AcCl, iPr₂NEt, 4-(N-benzyl-N-methylamino) pyridine polymer-supported, CH₂Cl₂) or by N-CBz-Protection (e.g. with BnOCOCl, iPr₂NEt, 4-Benzyl-N-methylamino)pyridine polymer supported, CH₂Cl₂), followed by selective BOC deprotection (e.g. with TFA, CH₂Cl₂ at −20° C. to room temperature) and reaction with a reactive R³ derivative (e.g. R³CO₂Cl, iPr₂NEt, 4-(N-Benzyl-N-methylamino)pyridine polymer-supported, CH₂Cl₂; step c(or conversion to all other R³X described before)) and formation of the thiol (e.g. with iPr₃SiH, TFA, CH₂Cl₂).

For Y being C-, protected-N—, O- or S-substituents step e of scheme 6 shows formation of S-compounds of thiol inhibitors of formula (I) by (a) reaction of the free thiol with for example AcCl in pyridine or PhCOCl in pyridine at 0° C. to room temperature or (b) a S-derivative synthesis (e.g. with BOC-Cys(Npys)-OH=2-(BOC-Cys)disulfanyl-3-nitro-pyridine or Ac-Cys(Npys)-OH=2-(acetyl-Cys)disulfanyl-3-nitro-pyridine) in DMF/0.1 M phosphate buffer (pH 6.2). The reaction for Y being protected N-atoms (Y deprotection) can be performed selective with for example HBr/AcOH in EtOAc. Step f shows the formation of the thiol as described above.

SCHEME 6

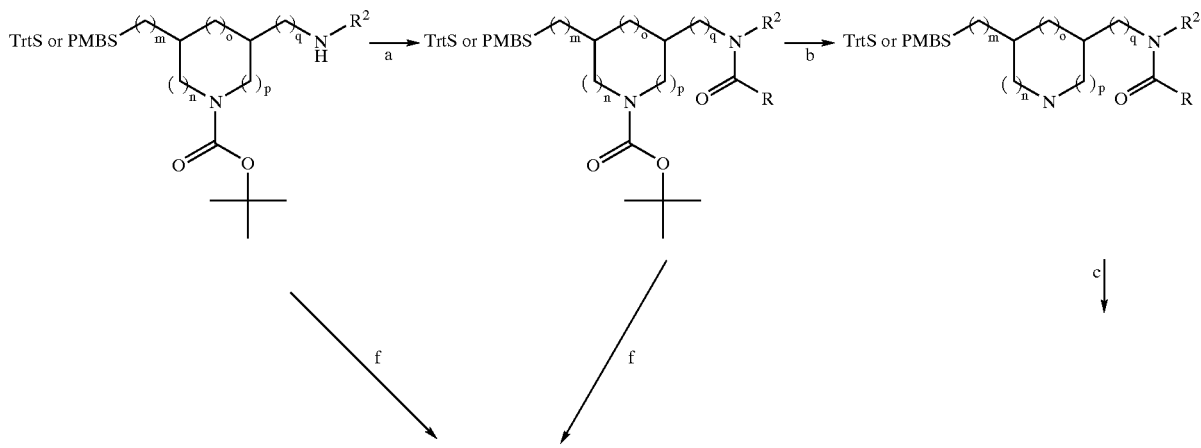

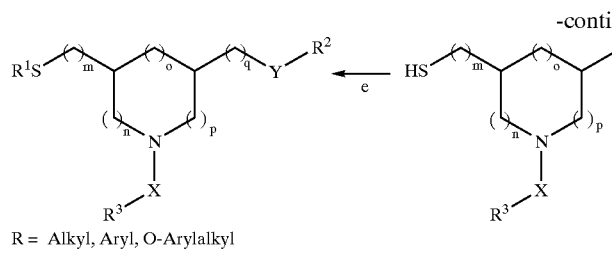
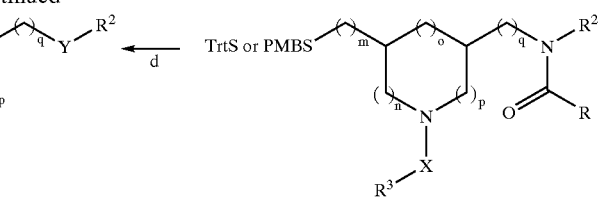

R = Alkyl, Aryl, O-Arylalkyl

The present invention also refers to the above described processes, especially to processes for the preparation of a compound of the present invention comprising reaction of a compound of formula V

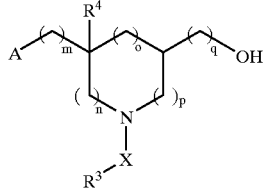

(V)

wherein $R^1$, $R^3$, $R^4$, X, Y, m, n, o, q and p are as defined above and A is a HS-protecting group a) with a $R^2$-halogenide for introduction of a —$OR^2$ group: or
b) mesylation of a compound of formula (V), followed by reaction with H $R^6$N—$R^2$ or $HSR_2$ or HN-heterocycles for introduction of a —$NR^6$—$R^2$ or —$SR^2$ group or —N-heterocycle;
optionally followed by conversion of a $R^3$—X group into a different oneand/or deprotection and/or thiol liberation.

Dimeric forms of a compound of formula I may be prepared by oxidative treatment of the formula I monomers.

On the basis of their capability of inhibiting metalloprotease activity, especially zinc hydrolase activity, the compounds of formula I can be used as medicaments for the treatment and prophylaxis of disorders which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The ability of the compounds of formula (I) to inhibit metalloprotease activity, particularly zinc hydrolase activity, may be demonstrated by a variety of in vitro and in vivo assays known to those of ordinary skill in the art. Pharmaceutically acceptable esters, pharmaceutically acceptable salts and dimeric forms of the compounds of formula I can also be tested by those of ordinary skill in the art for their ability to inhibit metalloprotease activity.

A) Cell Culture

A stable human umbilical vein endothelial cell line (ECV304) was cultured in "cell factories" as described until confluency (Schweizer et al. 1997, Biochem. J. 328: 871–878). At confluency cells were detached with a trypsin/EDTA solution and collected by low speed centrifugation. The cell pellet was washed once with phosphate buffered saline pH 7.0 and stored at −80° C. until use.

B) Solubilization of ECE from ECV304 Cells

All procedures were performed at 0–4° C. if not stated otherwise. The cell pellet of $1 \times 10^9$ cells was suspended in 50 ml of buffer A (20 mM Tris/HCl, pH 7.5 containing 5 mM $MgCl_2$, 100 μM PMSF, 20 μM E64, 20 μM leupeptin) and sonicated. The resulting cell homogenate was centrifuged at 100,000 $g_{av}$ for 60 minutes. The supernatant was discarded and the resulting membrane pellet was homogenized in 50 ml buffer A and centrifugated as described. The washing of the membrane fraction in buffer A was repeated twice. The final membrane preparation was homogenized in 50 ml of buffer B (buffer A+0.5% Tween 20 (v/v), 0.5% CHAPS (w/v), 0.5% Digitonin (w/v)) and stirred at 4° C. for 2 hours. Thereafter the remaining membrane fragments were sedimented as described. The resulting clear supernatant containing the solubilized ECE was stored in 1.0 ml aliquots at −120° C. until use.

C) ECE Assay

The assay measured the production of ET-1 from human big ET-1. To measure high numbers of samples an assay performed in 96 well plates was invented. The enzyme reaction and the radioimmunological detection of the produced ET-1 was performed in the same well, using a specifically developed and optimized coating technique.

D) Coating of Plates

Fluoronunc Maxisorp White (code 437796) 96 well plates were irradiated with 1 joule for 30 minutes in a UV Stratalinker 2400 (Stratagene). The 96 well plates were then fill with 300 μl protein A solution (2 μg/ml in 0.1 M $Na_2CO_3$ pH 9.5) per well and incubated for 48 hours at 4° C. Coated plates can be stored for up to 3 weeks at 4° C. until use.

Before use the protein A solution is discarded and the plates are blocked for 2 hours at 4° C. with 0.5% BSA in 0.1M $Na_2CO_3$, pH 9.5.

Plates were washed with bidestilled water and were ready to perform the ECE assay.

E) Screening Assay

Test compounds are solved and diluted in DMSO. 10 μl of DMSO was placed in the wells, followed by 125 μl of assay buffer (50 mM Tris/HCl, pH 7.0, 1 μM Thiorphan, 0.1% $NaN_3$, 0.1% BSA) containing 200 ng big ET-1. The enzyme reaction was started by the addition of 50 μl of solubilized ECE (diluted in assay buffer 1:30 to 1:60 fold (v/v)). The enzyme reaction was carried out for 30 minutes at 37° C. The enzyme reaction was stopped by addition of 10 μl 150 mM ETDA, pH 7.0.

F) Radioimmunoassay

The ET-1 RIA was performed principally as described earlier (Löffler, B.-M. and Maire, J.-P. 1994, Endothelium 1: 273–286). To plates containing the EDTA stopped enzyme reaction mixture 25 μl of assay buffer containing 20000 cpm (3-($^{125}$I)Tyr)-endothelin-1 and 25 μl of the ET specific antiserum AS-3 (dilution in assay buffer 1:1000) was added. Plates were incubated under mixing at 4° C. over night. Thereafter, the liquid phase was sucked with a plate washer and plates were washed once with bidestilled water. To the washed plates 200 μl scintillation cocktail (Microscint 40 LSC-Cocktail, Packard, code 6013641) was added and plates were counted for 2 minutes per well in a Topcount.

Standard curves were prepared in plates with synthetic ET-1 with final concentrations of 0 to 3000 pg ET-1 per well. In all plates controls for maximal ECE activity (in the presence of 10 μl DMSO) and for background production of ET-1 immunoreactivity (in the presence of 10 mM EDTA or 100 μM phosphoramidon) were performed. Assays were run in triplicate.

G) Kinetic Assay

The described assay format could be used to determine the kinetic characteristics of the used ECE preparation as well as different ECE inhibitors (i.e. Km, Ki) by variation of the substrate concentration used in the assay.

H) Cell Based ECE Assay

Human ECE-1c was stable expressed in MDCK cells as described (Schweizer et al. 1997, Biochem. J. 328: 871–878). Cells were cultured in 24 well plates to confluency in Dulbecco's modified Eagles's medium(DMEM) supplemented with 10% (v/v) fetal bovine serum (FBS), 0.8 mg/ml geneticin, 100 i.u./ml penicillin and 100 μg/ml streptomycin in a humidified air/CO$_2$ (19:1) atmosphere. Before ECE assay the medium was replaced by 0.5 ml DMEM-HBSS 1:1, 10 mM HEPES pH 7.0 supplemented with 0.1% (w/v) BSA. The inhibitors were added in DMSO at a final concentration of 1%. The enzyme reaction was started by the addition of 0.42 μM human big ET-1 and performed for 1.5 hours at 37° C. in an incubator. At the end of incubation, the incubation medium was quickly removed and aliquots were analysed by radioimmunoassay for produced ET-1 as described above.

The ECE screening assay was validated by the measurement of the characteristic inhibitor constants of phosphoramidon (IC$_{50}$ 0.8±0.2 μM) and CGS 314447 (IC$_{50}$ 20±4 nM) [De Lombaert, Stephane; Stamford, Lisa B.; Blanchard, Louis; Tan, Jenny; Hoyer, Denton; Diefenbacher, Clive G.; Wei, Dongchu; Wallace, Eli M.; Moskal, Michael A.; et al. Potent non-peptidic dual inhibitors of endothelin-converting enzyme and neutral endopeptidase 24.11. Bioorg. Med. Chem. Lett. (1997), 7(8), 1059–1064]. All three inhibitors were measured with IC$_{50}$ values not significantly different from those described in the literature but measured with different assay protocols. In the cell based assay phosphoramidon showed an IC$_{50}$ of 4 μM. This assay gave additional information about the inhibitory potency of inhibitors under much more physiologic conditions, as e.g. the ECE was embedded in a normal plasma membrane environment. It is important to state, that the screening assay was performed in the presence of 1 μM Thiorphan to block any potential big ET-1 degradation due to the action of NEP24.11. No NEP activity was present in MDCK-ECE-1c transfected cells in preliminary experiments when ET-1 production was measured in presence or absence of thiorphan. In subsequent experiments no thiorphan was added in the incubation medium.

According to the above methods, the compounds of the present invention show activity values in the radioimmunoassay (E and F) of about 0.5 nM to about 100 μM. The preferred compounds show values of 0.5 nM to 100 nM.

As mentioned earlier, medicaments containing a compound of formula I are also an object of the present invention as is a process for the manufacture of such medicaments, which process comprises bringing one or more compounds of formula I and, if desired, one or more other therapeutically valuable substances into a galenical administration form.

The pharmaceutical compositions may be administered orally, for example in the form of tablets, coated tablets, drages, hard or soft gelatin capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragees or hard gelatin capsules the compounds of the present invention may be admixed with pharmaceutically inert, inorganic or organic excipients. Examples of suitable excipients for tablets, dragees or hard gelatin capsules include lactose, maize starch or derivatives thereof, talc or stearic acid or salts thereof.

Suitable excipients for use with soft gelatin capsules include for example vegetable oils, waxes, fats, semi-solid or liquid polyols etc. According to the nature of the active ingredients, it may, however, be the case that no excipient is needed at all for soft gelatin capsules.

For the preparation of solutions and syrups, excipients which may be used include for example water, polyols, saccharose, invert sugar and glucose. For injectable solutions, excipients which may be used include for example water, alcohols, polyols, glycerin, and vegetable oils. For suppositories, and local or percutaneous application, excipients which may be used include for example natural or hardened oils, waxes, fats and semi-solid or liquid polyols.

The pharmaceutical compositions may also contain preserving agents, antioxidants, solubilising agents, stabilizing agents, wetting agents, emulsifiers, sweeteners, colorants, odorants, salts for the variation of osmotic pressure, buffers, coating agents or antioxidants. They may also contain other therapeutically valuable agents.

The dosages in which the compounds of formula I are administered in effective amounts depend on the nature of the specific active ingredient, the age and the requirements of the patient and the mode of application. In general, dosages of 0.1–100 mg/kg body weight per day come into consideration, although the upper limit quoted can be exceeded when this is shown to be indicated.

The following specific examples are provided as a guide to assist in the practice of the invention, and are not intended as a limitation on the scope of the invention.

EXAMPLES

All reactions are done under argon.

A) Abbreviations

EtOAc ethylacetate, EtOH ethanol, THF tetrahydrofurane, Et$_2$O diethylether, MeOH methanol, CH$_2$Cl$_2$ dichloromethane, EDCI N-(3-Dimethylaminopropyl)-N'-ethylcarbodiimide hydrochloride, HOBT 1-Hydroxybenzotriazole, DBU 1,8-Diazabicyclo[5.4.0]undec-7-ene(1,5-5), LAH Lithium aluminum hydride, LDA lithium diisopropylamide, DEAD Diethyl azodicarboxylate, DIAD Diisopropyl azodicarboxylate, DMAP 4-Dimethylaminopyridine, TBAF tetrabutylammonium fluoride, iPr$_2$NEt N-ethyldiisopropylamine, Ph$_3$P triphenylphosphine, P(Bu)$_3$ tributylphosphine, Red-Al solution Natrium-dihydrido-bis-(2-methoxyethoxy)-aluminat-solution, NMM N-methylmorpholine, Et$_3$N triethylamine, Cl$_3$COCl=diphosgene=trichloromethyl-chloroforamate, PMB p-methoxy-benzyl, Trt trityl=Ph$_3$CSH, DTT 1,4-Dithio-DL-threitol, BOC-Cys(Npys)-OH 2-(BOC-Cys)disulfanyl-3-nitro-pyridine, Ac-Cys(Npys)-OH 2-(acetyl-Cys)disulfanyl-3-nitro-pyridine.

B) General Method for a Selective BOC-deprotection

A solution of 15.1 mmol N-BOC-S-Trityl compound in 30 ml CH$_2$Cl$_2$ was treated at −20° C. with 34 ml TFA and warmed up to room temperature during 5.5 h. The reaction was evaporated and treated with aqueous saturated NaHCO$_3$ solution/EtOAc (3×) to give the free aminotritylsulfanyl.

C) General Method for EDCI-coupling

Weinreb-amide formation: A solution of 13.6 mmol carboxylic acid in 150 ml CH$_2$Cl$_2$ was treated at 0° C. with 95.2 mmol N-methylmorpholine, 0.37 g (2.72 mmol) HOBT, 6.26 g (32.64 mmol) EDCI and 2.92 g (29.92 mmol) N,O-dimethylhydroxyl-amine hydrochloride. The reaction was stirred over night at room temperature and partitioned between aqueous 10% KHSO$_4$/EtOAc (3×). The organic phases were washed with aqueous saturated NaCl and dried over Na$_2$SO$_4$. Purification by flash-chromatography on silica gel (Hexane/EtOAc 1:1) gave of methoxy-methyl-carbamoyl derivative.

D) General Method for Ester Hydrolysis

A solution of 5.38 mmol carboxylic acid methyl ester was dissolved in 150 ml EtOH and treated at RT with 10.8 ml (10.8 mmol) aqueous 1 N NaOH. After 3 h the reaction was evaporated and poured into aqueous 10% KHSO$_4$/EtOAc (3×). The organic phases were washed with aqueous 10% NaCl solution and dried over Na$_2$SO$_4$ to give the carboxylic acid.

E) General Method for S-deprotection

Method 1: TFA/triethylsilane deprotection for labile p-methoxy-benzylsulfanyl compounds: A solution of 0.15 mmol p-methoxy-benzylsulfanyl was dissolved in 2 ml TFA, cooled to 0° C. and treated with 0.24 ml (1.5 mmol) triethylsilane, stirred for 22 h at room temperature (the reaction was followed by TLC, if necessary treated again with 0.24 ml (1.51 mmol) triethylsilane and stirred for 30 h). The evaporated residue was purified by flash silica gel column to give the thiol compound.

Method 2: TFA/triethylsilane deprotection for not labile p-methoxy-benzylsulfanyl compounds: A solution of 0.25 mmol p-methoxy-benzylsulfanyl and 0.4 ml (2.5 mmol) triethylsilane was heated for 1 min −1.5 h at 80° C. (followed by TLC), cooled to RT and evaporated. Crystallization from Et$_2$O/pentane gave the thiol-compound.

Method 3: Trityl deprotection for single compound: A solution of 0.58 mmol tritylsulfanyl in 5.8 ml TFA was treated at 0° C. with 0.92 ml (5.78 mmol) triethylsilane and after 10 min at room temperature evaporated and purified by flash chromatography on silica gel (Hexane/EtOAc 4:1) to give the thiol-compound.

Method 4: Trityl deprotection for parallel synthesis: A solution of 0.32 mmol trityl-protected compound was dissolved in 1.5 ml acetonitril/0.4 ml TFA/0.1 ml triethylsilane and after 1 night at room temperature purified by preparative HPLC (RP18, CH$_3$CN/H$_2$O 80:20 to 95:5) to give the free thiols.

Method 5: Trityl deprotection in the presence of BOC: 1 eq Trityl-protected compound in CH$_2$Cl$_2$ (15–20 ml/mmol) was treated with 10 eq triisopropyl silane and 10 eq TFA at 0° C. or RT until no starting material could be detected. The solution was poured on saturated NaHCO$_3$ solution and the inorganic phase was extracted with CH$_2$Cl$_2$, the organic phases were washed with brine, dried over Na$_2$SO$_4$ and evaporated and purified by flash chromatography to give the free amine.

Example 1

Starting Materials

Example 1.a

Alcohols: 40 g (220 mmol) of L-hydroxyproline methylester hydrochloride (twice suspended in toluene and evaporated under reduced pressure to remove water) was suspended in 600 ml hexamethyldisilazane and refluxed for 2 h. The solution was evaporated under reduced pressure and dissolved in 100 ml THF. 49.9 g (220 mmol) of 2-naphthalene-sulphonyl chloride in 200 ml of THF were added slowly and stirred for 16 h at room temperature. 150 ml H$_2$O were added and after 1 h the solvents were evaporated. The residue was partitioned between water/EtOAc (3×), the organic phases were washed with 10% NaCl and dried over Na$_2$SO$_4$ to give 60.4 g (82%) of (2S,4R)-4-hydroxy-1-(naphthalene-2-sulfonyl)-pyrrolidine-2-carboxylic acid methyl ester, MS: 335 (M$^+$).

The following compounds were prepared in an analogous manner:

L-hydroxyproline benzylester hydrochloride and 1-naphthalenesulfonyl chloride gave (2S,4R)-4-hydroxy-1-(naphthalene-2-sulfonyl)-pyrrolidine-2-carboxylic acid benzyl ester, MS: 411 (MH$^+$);

L-hydroxyproline benzylester hydrochloride and methanesulfonyl chloride gave (2S,4R)-4-hydroxy-1-methanesulfonyl-pyrrolidine-2-carboxylic acid benzyl ester, mp 132–133° C., MS: 300 (MH$^+$);

L-hydroxyproline methylester hydrochloride and methanesulfonyl chloride gave after extraction with CH$_2$Cl$_2$ (2S,4R)-4-hydroxy-1-methanesulfonyl-pyrrolidine-2-carboxylic acid methyl ester, mp 115.5–117° C., MS: 164 (M-COOMe.).

Example 1.b

Via Mesylate: A biphasic solution of 13.9 ml (215 mmol) methanesulfonic acid, 29.8 ml (215 mmol) triethylamine and 58.7 g (224 mmol) triphenylphosphine in 150 ml toluene was added to a suspension of 60 g (179 mmol) (2S,4R)-4-hydroxy-1-(naphthalene-2-sulfonyl)-pyrrolidine-2-carboxylic acid methyl ester in 300 ml toluene which was stirred mechanically. After adding 44.9 ml (233 mmol) of diisopropyl azodicaboxylate (exothermic!) the solution was heated for 2.5 h at 80° C. 300 ml water was added at room temperature and extracted with EtOAc (3×300 ml). The organic phase was washed with aqueous 10% $KHSO_4$ (2×100 ml), 10% NaCl (2×150 ml) dried over $Na_2SO_4$ and evaporated to give 180 g of crude product. Flash chromatography (EtOAc/hexane 1:1) gave 63.7 g (86%) of (4S,2S)-4-methanesulfonyloxy-1-(naphthalene-2-sulfonyl)-pyrrolidine-2-carboxylic acid methylester.

64.2 g (167 mmol) of triphenylmethanthiol was slowly added at room temperature to a solution of 17.9 g (160 mmol) of potassium tert-butylate in 300 ml DMF and stirred mechanically for 30 min. Then 63 g (152 mmol) of (4S,2S)-4-methanesulfonyloxy-1-(naphthalene-2-sulfonyl)-pyrrolidine-2-carboxylic acid methylester in 300 ml DMF were added at 20° C. by cooling at the end with an ice bath. The reaction was heated for 1.3 h at 100° C., cooled, evaporated to 400 ml and extracted with 250 ml aqueous saturated $NH_4Cl$/EtOAc (3×300). The organic phases were washed with aq. 10% NaCl, dried ($Na_2SO_4$) and evaporated. Flash chromatography ($CH_2Cl_2$/MeOH 99:1) gave 58.6 g (65%, (2S,4R)/(2R,4R)-isomer ca 4:1, 1H-NMR) and 9.2 g (10%, (2S,4R)/(2R,4R)-isomer ca 1:1, $^1$H-NMR) of (2S,4R)-1-(naphthalene-2-sulfonyl)-4-tritylsulfanyl-pyrrolidine-2-carboxylic acid methyl ester, MS: 594 (MH$^+$).

The following compounds were prepared:

(2S,4R)-4-hydroxy-1-methanesulfonyl-pyrrolidine-2-carboxylic acid methyl ester gave after 3.75 h at 80° C. (4S,2S)-4-methanesulfonyloxy-1-(methylsulfonyl)-pyrrolidine-2-carboxylic acid methylester which was heated for 45 min at 100° C. with triphenylmethanthiolate to give (2S,4R)-1-methanesulfonyl-4-tritylsulfanyl-pyrrolidine-2-carboxylic acid methyl ester (2S,4R)/(2R,4R)-isomer ca 9:1, $^1$H-NMR), MS: 482 (MH$^+$);

(2S,4R)-4-hydroxy-1-methanesulfonyl-pyrrolidine-2-carboxylic acid benzyl ester gave after 5 h at 80° C. (2S,4S)-1-methanesulfonyl-4-methanesulfonyloxy-pyrrolidine-2-carboxylic acid benzyl ester which was heated for 30 min with 4-methoxybenzylthiol/potassium tert-butylate to give (2S,4S)-1-methanesulfonyl-4-methanesulfonyloxy-pyrrolidine-2-carboxylic acid benzyl ester, mp 91–92° C., MS: 453 (M+NH$_4^+$).

Example 1.c

Via bromid: To a solution of 76.5 g (291.6 mmol, 6 eq) triphenylphosphine in 650 ml THF were added 44.6 ml (286.8 mmol, 5.9 eq) DEAD in 70 ml THF at a temperature between 1.5–4.5° C. over a period of 0.5 h. The solution was stirred for 0.5 h before 42.2 g (486.1 mmol, 10 eq) LiBr were added, and the reaction mixture was recooled to 4° C. for the addition of 20 g (48.6 mmol) (2S,4R)-4-hydroxy-1-(naphthalene-2-sulfonyl)-pyrrolidine-2-carboxylic acid benzyl ester in 75 ml THF. After stirring at room temperature for 3 h, water was added and the suspension concentrated and redissolved in 700 ml EtOAc and water. The layers were separated, the inorganic one was extracted with 100 ml of EtOAc (3×), and the combined organic layers were washed with brine, dried over $MgSO_4$ and evaporated. Triphenylphosphine oxide was removed by crystallization from EtOAc/hexane and the mother liquid was purified by colum chromatography on silica gel with hexane: EtOAc 3:1 yielding 13.4 g (62%) of (2S,4S)-4-bromo-1-(naphthalene-2-sulfonyl)-pyrrolidine-2-carboxylic acid benzyl ester as colorless solid, mp 97–98° C., MS: 473 (MH$^+$).

3.38 g (30.1 mmol, 1.1 eq) potassium tert. butylate in 150 ml DMF were treated with 4.4 ml (31.5 mmol, 1.15 eq) 4-methoxybenzyl mercaptane at 0° C. The solution was stirred for 1 h at RT before 12.99 g (27.4 mmol) (2S,4S)-4-bromo-1-(naphthalene-2-sulfonyl)-pyrrolidine-2-carboxylic acid benzyl ester in 100 ml DMF were added. The reaction was stirred at room temperature overnight, DMF was removed under vacuum, and the residue redissolved in EtOAc and 1M aqueous $KHSO_4$. The layers were separated, and the organic one washed with brine, dried over $Na_2SO_4$ and evaporated. The crude oil was purified by flash chromatography on silica gel with hexane/EtOAc (3:1–2:1) as eluent yielding 7.23 g (48%) (2S,4R)-4-(4-methoxy-benzylsulfanyl)-1-(naphthalene-2-sulfonyl)-pyrrolidine-2-carboxylic acid benzyl ester as light yellow solid, mp 90–91° C., MS: 547 (M$^+$).

The following compounds were prepared:

(2S,4R)-4-hydroxy-pyrrolidine-1,2-dicarboxylic acid 1-tert-butyl ester 2-methyl ester with 4-methoxybenzylthiol potassium tert-butylate gave (2S,4R)-4-(4-methoxy-benzylsulfanyl)-pyrrolidine-1,2-dicarboxylic acid 1-tert-butyl ester 2-methyl ester, MS: 382 (MH$^+$).

Example 1.d

Via chloride: A solution of 374 g (1.48 mol) (2S,4R)-4-hydroxy-pyrrolidine-1,2-dicarboxylic acid 1-tert-butyl ester 2-methyl ester in 1.61 $CH_2Cl_2$ was treated with 680 g (2.6 mol) triphenylphosphine, cooled to 3–5° C. and treated in 10 min with 1.241 (12.8 mol) $CCl_4$, after 2 h at this temperature cooling was stopped, the reaction temperature was raised during 2 h to 35° C. It was cooled down to 20° C. and stirred for further 45 min. After addition of 4 l of n-heptane, the reaction was evaporated to 2.9 l, cooled to 0° C., filtered, the residue was treated twice the same way, the third time by dissolving the residue again in 2 l of $CH_2Cl_2$. The solvents were evaporated and filtered through silica gel with hexane/tert.-butyl-methylether 9:1 as eluent. Evaporation of the solvents gave 347 g (89%) of (2S,4S)-4-chloro-pyrrolidine-1,2-dicarboxylic acid 1-tert-butyl ester 2-methyl ester, MS: 246 (MH$^+$).

A solution of 76 g (0.68 mol) potassium-tert.-butylate in 1.5 l DMF was cooled (−3° C.) and treated slowly (1.5 h) with 202 g (0.73 mol) triphenylmethanethiole in 0.8 l DMF (at max 1° C.). After 2.5 h at 0° C., a solution of 161 g (0.61 mol) of (2S,4S)-4-chloro-pyrrolidine-1,2-dicarboxylic acid 1-tert-butyl ester 2-methyl ester in 0.35 l DMF was added. The reaction was stirred over night at 2° C., evaporated, dissolved in 1.5 l EtOAc, poured into 2.7 l aqueous saturated NH$_4$Cl solution and extracted with EtOAc (2×). The organic phase was washed with aqueous saturated NaHCO$_3$, dried over Na$_2$SO$_4$ and evaporated. Column chromatography on silica gel with hexane/EtOAc (95:5 to 7:3) gave 268 g (87%) (2S,4R)-4-tritylsulfanyl-pyrrolidine-1,2-dicarboxylic acid 1-tert-butyl ester 2-methyl ester, MS: 504 (MH$^+$).

Example 1.e

Ester reduction, Method A: 57 ml (57 mmol, 1M THF solution) of LAH was added during 15 min to a cold solution (−20° C.) of 28.2 g (47.5 mmol, ca. (2S,4R)/(2R,4R)-isomer ca 4:1) (2S,4R)-1-(naphthalene-2-sulfonyl)-4-tritylsulfanyl-pyrrolindine-2-carboxylic acid methyl ester in 460 ml THF. The reaction was stirred for 20 min, cooled to −78° C. and quenched with a suspension of 15 g silica gel/15 g MgSO$_4$ 7H$_2$O in 60 ml aqueous 10% KHSO$_4$. The suspension was stirred for 15 min at room temperature, filtered and washed with THF. After evaporation of the THF, the residue was taken up in CH$_2$Cl$_2$, dried over Na$_2$SO$_4$ and evaporated to give 29.2 g crude product. Flash column chromatography on silica gel with CH$_2$Cl$_2$/EtOAc(2.5%) to CH$_2$Cl$_2$/EtOAc (10%) gave 21.7 g (81%) of (2S,4R)-[1-(naphthalene-2-sulfonyl)-4-tritylsulfanyl-pyrrolidin-2-yl]-methanol and 1.0 g (4%) of [(2R,4R)-4-mercapto-1-(naphthalene-2-sulfonyl)-pyrrolidin-2-yl]-methanol, MS: 566 (MH$^+$).

The following compounds were prepared:

(2S,4R)-1-methanesulfonyl-4-tritylsulfanyl-pyrrolidine-2-carboxylic acid methyl ester [(2S,4R)/(2R,4R)-isomer ca. 9:1] gave isomerically pure (2S,4R)-(1-methanesulfonyl-4-tritylsulfanyl-pyrrolidin-2-yl)-methanol, MS: 471 (M+NH$_4^+$);

(2S,4S)-1-methanesulfonyl-4-methanesulfonyloxy-pyrrolidine-2-carboxylic acid benzyl ester gave (2S,4R)-[1-methanesulfonyl-4-(4-methoxy-benzylsulfanyl)-pyrrolidin-2-yl]-methanol, MS: 331 (M);

(2S,4R)-4-(4-Methoxy-benzylsulfanyl)-1-(naphthalene-2-sulfonyl)-pyrrolidine-2-carboxylic acid benzyl ester gave (2S,4R)-[4-(4-methoxy-benzylsulfanyl)-1-(naphthalene-2-sulfonyl)-pyrrolidin-2-yl]-methanol as colorless solid, mp 114–115° C., MS: 444 (MH$^+$);

(2S,4R)-4-(4-Methoxy-benzylsulfanyl)-pyrrolidine-1,2-dicarboxylic acid 1-tert-butyl ester 2-methyl ester gave (2S,4R)-2-hydroxymethyl-4-(4-methoxy-benzylsulfanyl)-pyrrolidine-1-carboxylic acid tert-butyl ester, MS: 252 (M-COOt-Bu);

(2S,4S)-4-Chloro-pyrrolidine-1,2-dicarboxylic acid 1-tert-butyl ester 2-methyl ester gave (2S,4S)-4-chloro-2-hydroxymethyl-pyrrolidine-1-carboxylic acid tert-butyl ester; MS: 162 (M-t-BuO).

Example 1.f

Ester reduction, Method B: A solution of 35 g (69 mmol) (2S,4R)-4-Tritylsulfanyl-pyrrolidine-1,2-dicarboxylic acid 1-tert-butyl ester 2-methyl ester in 380 ml toluene/60 ml THF was treated at −47° C. to −50° C. with 44 g (152 mmol) of a 70% solution of sodium dihydrido-bis(2-methoxy-ethoxo)aluminate in toluene (3.5 M Red-Al in toluene). After 3 h at −50° C. and 1 h at −30° C. the solution was poured into water (1 l) with 40 g of citric acid and extracted with EtOAc (2×). The organic phase was dried over Na$_2$SO$_4$ and evaporated. Column chromatography on silica gel with hexane/EtOAc (7:3) gave 23.0 g (69%) (2S,4R)-2-hydroxymethyl-4-tritylsulfanyl-pyrrolidine-1-carboxylic acid tert-butyl ester, MS: 476 (MH$^+$).

Example 1.g

Synthesis According to Podlech & Seebach, Liebigs Ann. (1995), 7, 1217–28

A solution of 3.0 g (5.38 mmol) (2S,4R)-1-methanesulfonyl-4-tritylsulfanyl-pyrrolidine-2-carboxylic acid methyl ester was dissolved in 150 ml EtOH and treated at room temperature with 10.8 ml (10.8 mmol) aqueous 1 N NaOH. After 3 h the reaction was evaporated and poured into aqueous 10% KHSO$_4$/EtOAc (3×). The organic phases were washed with aqueous 10% NaCl solution and dried over Na$_2$SO$_4$ to give 2.43 g (97%) of (2S,4R)-1-(naphthalene-2-sulfonyl)-4-tritylsulfanyl-pyrrolidine-2-carboxylic acid, mp 64–69° C., MS: 466 (M−H)$^-$.

A solution of 25 g (93 mmol) (2S,4R)-1-methanesulfonyl-4-tritylsulfanyl-pyrrolidine-2-carboxylic acid in 265 ml CH$_2$Cl$_2$ at 0° C. was treated with 2 drops of DMF followed by 8 ml (99 mmol) oxalylchloride. After 15 min at 0° C. the reaction was stirred 2 h at room temperature, evaporated and dissolved in 260 ml THF/CH$_3$CN 1:1. 58.5 ml (117 mmol) 2M trimethylsilyldiazomethane solution in hexane was then added at 0° C. The reaction was stirred 16 h at room temperature, evaporated and poured in H$_2$O/EtOAc. The organic phase was dried over Na$_2$SO$_4$, evaporated and purified by flash column chromatography on silica gel with hexane/EtOAc (7:3 to 1:1) to give 12.4 g (48%) of (2S,4R)-2-diazo-1-(1-methanesulfonyl-4-tritylsulfanyl-pyrrolidin-2-yl)-ethanone, MS: 509 (M+NH4$^+$).

In analogy to above, (2S,4R)-2-diazo-1-[1-(naphthalene-2-sulfonyl)-4-tritylsulfanyl-pyrrolidin-2-yl]-ethanone was obtained from (2S,4R)-1-(naphthalene-2-sulfonyl)-4-tritylsulfanyl-pyrrolidine-2-carboxylic acid (with 2.3 eq. Trimethylsilyl-diazomethane) in 57% yield, MS: 621 (M+NH4$^+$).

A solution of 12 g (24.4 mmol) (2S,4R)-2-diazo-1-(1-methanesulfonyl-4-tritylsulfanyl-pyrrolidin-2-yl)-ethanone in 96 ml MeOH/67 ml THF was cooled (−25° C.) and treated in the dark with 0.62 g (2.7 mmol) silver benzoate in 13.9 ml (99.7 mmol) triethylamine. The reaction was warmed to room temperature and stirred 1 h at RT, evaporated, extracted with H$_2$O/EtOAc and flash column chromatography on silica gel with hexane/EtOAc (7:3) gave 8.7 g (72%) of (2R,4R)-(1-methanesulfonyl-4-tritylsulfanyl-pyrrolidin-2-yl)-acetic acid methyl ester, MS: 496 (MH$^+$).

In analogy to above, (2R,4R)-[1-(naphthalene-2-sulfonyl)-4-tritylsulfanyl-pyrrolidin-2-yl]-acetic acid methyl ester was obtained from (2S,4R)-2-diazo-1-[1-(naphthalene-2-sulfonyl)-4-tritylsulfanyl-pyrrolidin-2-yl]-ethanone in 72% yield, MS: 625 (M+NH$_4^+$).

Following the procedure of ester reduction, Method A, (2R,4R)-(1-methane-sulfonyl-4-tritylsulfanyl-pyrrolidin-2-yl)-acetic acid methyl ester gave (2R,4R)-2-(1-methanesulfonyl-4-tritylsulfanyl-pyrrolidin-2-yl)-ethanol, MS: 468 (MH$^+$).

Following the procedure of ester reduction, Method A, (2S,4R)-2-diazo-1-[1-(naphthalene-2-sulfonyl)-4-tritylsulfanyl-pyrrolidin-2-yl]-ethanone gave (2R,4R)-2-[1-(naphthalene-2-sulfonyl)-4-tritylsulfanyl-pyrrolidin-2-yl]-ethanol, MS: 580 (MH$^+$).

Example 1.h

Further starting compounds: Hydrolysis (see General Method for hydrolysis of an ester) of (2S,4R)-4-(4-methoxy-benzylsulfanyl)-pyrrolidine-1,2-dicarboxylic acid 1-tert-butyl ester 2-methyl ester gave (2S,4R)-4-(4-Methoxy-benzylsulfanyl)-pyrrolidine-1,2-dicarboxylic acid 1-tert-butyl ester, MS: (M–H)-366.

A solution of 5 g (13.6 mmol) (2S,4R)-4-(4-Methoxy-benzylsulfanyl)-pyrrolidine-1,2-dicarboxylic acid 1-tert-butyl ester 20-5620 in 150 ml $CH_2Cl_2$ was treated with 10.5 ml (95.2 mmol) N-methylmorpholine, 0.37 g (2.72 mmol) 1-hydroxybenzotriazole, 6.26 g (32.64 mmol) EDCI and 2.92 g (29.92 mmol) N,O-dimethylhydroxylamine hydrochloride. The reaction was stirred over night at room temperature and partitioned between aqueous 10% $KHSO_4$/EtOAc (3×). The organic phases were washed with aqueous saturated NaCl and dried over $Na_2SO_4$. Purification by flash-chromatography on silica gel (Hexane/EtOAc 1:1) gave 3.6 g (62%) of (2S,4R)-4-(4-methoxy-benzylsulfanyl)-2-(methoxy-methyl-carbamoyl)-pyrrolidine-1-carboxylic acid tert-butyl ester, MS: 411 ($MH^+$).

A solution of 1.5 g (3.5 mmol) (2S,4R)-4-(4-methoxy-benzylsulfanyl)-2-(methoxy-methyl-carbamoyl)-pyrrolidine-1-carboxylic acid tert-butyl ester dissolved in 15 ml was added to 4.2 ml (4.2 mmol, 1M THF solution) of LAH in 50 ml THF at –78° C. The reaction was was warmed up to –30° C., cooled to –78° C. and quenched with a suspension of 1.2 g silica gel/1.2 g $MgSO_4 \cdot 7H_2O$ in 5 ml aqueous 10% $KHSO_4$. The suspension was stirred for 15 min at room temperature, filtered and washed with THF. After evaporation of the THF, the residue was taken up in $CH_2Cl_2$, dried over $Na_2SO_4$ and evaporated to give 1.2 g (98%) of (2S,4R)-2-formyl-4-(4-methoxy-benzylsulfanyl)-pyrrolidine-1-carboxylic acid tert-butyl ester, MS: 351 ($M^+$).

A solution of 0.91 g (4.08 mmol) triethyl phosphonoacetate in 10 ml THF was first treated with 0.18 g (4.08 mmol) 55% NaH and after cooling (–78° C.) with 1.2 g (3.4 mmol) (2S,4R)-2-formyl-4-(4-methoxy-benzylsulfanyl)-pyrrolidine-1-carboxylic acid tert-butyl ester. The reaction was warmed up to room temperature and stirred over night. The solution was cooled (0° C.) and treated with 1 ml MeOH followed by 10 ml saturated aqueous Na/K-tartrate and after 10 min with aqueous 10% $NaHCO_3$ solution. The aqueous phase was filtered, extracted (EtOAc 2×) and the organic phase was dried ($Na_2SO_4$), evaporated and purified on silica gel column (Hexane/EtOAc 9:1 to 7:3) to give 0.57 g (40%) of (2S,4R)-2-(2-ethoxycarbonyl-vinyl)-4-(4-methoxy-benzylsulfanyl)-pyrrolidine-1-carboxylic acid tert-butyl ester, MS: 422 ($MH^+$).

In analogy to literature [Hudlicky, T.; Sinai-Zingde, G.; Natchus, M. G. Tetrahedron Lett. (1987), 28(44), 5287-90] a solution of 0.35 g (0.84 mmol) (2S,4R)-2-(2-ethoxycarbonyl-vinyl)-4-(4-methoxy-benzylsulfanyl)-pyrrolidine-1-carboxylic acid tert-butyl ester in 20 ml MeOH was treated with 0.122 g (5.04 mmol) magnesium and stirred at room temperature for 5 h. The reaction was evaporated, suspended twice in EtOAc and filtered to give 0.38 g (quantitative) of (2R,4R)-4-(4-methoxy-benzylsulfanyl)-2-(2-methoxycarbonyl-ethyl)-pyrrolidine-1-carboxylic acid tert-butyl ester, MS: 410 ($MH^+$).

Following the procedure of ester reduction, Method A, (2R,4R)-4-(4-methoxy-benzylsulfanyl)-2-(2-methoxycarbonyl-ethyl)-pyrrolidine-1-carboxylic acid tert-butyl ester gave (2R,4R)-2-(3-hydroxy-propyl)-4-(4-methoxy-benzylsulfanyl)-pyrrolidine-1-carboxylic acid tert-butyl ester, MS: 382 ($MH^+$).

Following the procedure for the BOC-deprotection (general method for a selective BOC-deprotection), (2R,4R)-2-(3-hydroxy-propyl)-4-(4-methoxy-benzylsulfanyl)-pyrrolidine-1-carboxylic acid tert-butyl ester gave (2R,4R)-3-[4-(4-methoxy-benzylsulfanyl)-pyrrolidin-2-yl]-propan-1-ol, MS: 282 ($MH^+$).

A solution of 615 mg (2.19 mmol) (2R,4R)-3-[4-(4-methoxy-benzylsulfanyl)-pyrrolidin-2-yl]-propan-1-ol and 0.34 ml (2.40 mmol) triethylamine in 5 ml $CH_2Cl_2$ was cooled to –10° C. and treated slowly with 0.31 ml (2.29 mmol) butylchloroformate. After 20 min at this temperature the reaction was extracted with cold (0° C.) aqueous 10% $KHSO_4/Et_2O$ (3×). The organic phase was washed with aqueous saturated $NaHCO_3$ dried over $Na_2SO_4$ and evaporated. Flash column chromatography on silica gel with hexane/EtOAc (2:1 to 1:1) gave 340 mg (32%) of (2R,4R)-2-(3-butoxycarbonyloxy-propyl)-4-(4-methoxy-benzylsulfanyl)-pyrrolidine-1-carboxylic acid butyl ester and 230 mg (28%) of (2R,4R)-2-(3-hydroxy-propyl)-4-(4-methoxy-benzylsulfanyl)-pyrrolidine-1-carboxylic acid butyl ester, MS: 382 ($MH^+$).

In analogy: (2S,4R)-2-Hydroxymethyl-4-tritylsulfanyl-pyrrolidine-1-carboxylic acid tert-butyl ester gave via (2S,4R)-(4-tritylsulfanyl-pyrrolidin-2-yl)-methanol, (2S,4R)-2-hydroxymethyl-4-tritylsulfanyl-pyrrolidine-1-carboxylic acid butyl ester, MS: 476 ($MH^+$).

Example 2

Amines (via Mesylate)

A solution of 14.14 g (25 mmol) of (2S,4R)-[1-(naphthalene-2-sulfonyl)-4-tritylsulfanyl-pyrrolidin-2-yl]-methanol in 300 ml $CH_2Cl_2$ was treated at 0° C. with 2.14 ml (27.7 mmol) methane sulfonylchloride, 3.02 ml (37.5 mmol) pyridine, 3.05 g (25 mmol) DMAP and stirred at room temperature for 4 h. The reaction mixture was poured into EtOAc/$H_2O$ acidified with 1 N HCl. The organic phase was washed with 10% aqueous NaCl, dried over $Na_2SO_4$ and evaporated to give 15.98 g (99%) of methanesulfonic acid (2S,4R)-1-(naphthalene-2-sulfonyl)-4-tritylsulfanyl-pyrrolidin-2-ylmethyl ester, MS: 644 ($MH^+$).

The following compounds were prepared in an analogous manner:

(2S,4R)-[1-methanesulfonyl-4-(4-methoxy-benzylsulfanyl)-pyrrolidin-2-yl]-methanol gave (2S,4R)-methanesulfonic acid 1-methanesulfonyl-4-(4-methoxy-benzylsulfanyl)-pyrrolidin-2-ylmethyl ester in 82%, MS: 410 ($MH^+$).

(2R,4R)-2-(3-hydroxy-propyl)-4-(4-methoxy-benzylsulfanyl)-pyrrolidine-1-carboxylic acid butyl ester gave (2R,4R)-2-(3-methanesulfonyloxy-propyl)-4-(4-methoxy-benzylsulfanyl)-pyrrolidine-1-carboxylic acid butyl ester, MS: 460 ($MH^+$).

(2R,4R)-2-(1-methanesulfonyl-4-tritylsulfanyl-pyrrolidin-2-yl)-ethanol gave methanesulfonic acid (2R,4R)-2-(1-methanesulfonyl-4-tritylsulfanyl-pyrrolidin-2-yl)-ethyl ester, MS: 563 (MH$^+$).

(2S,4R)-[4-(4-methoxy-benzylsulfanyl)-1-(naphthalene-2-sulfonyl)-pyrrolidin-2-yl]-methanol gave methanesulfonic acid (2S,4R)-4-(4-methoxy-benzylsulfanyl)-1-(naphthalene-2-sulfonyl)-pyrrolidin-2-ylmethyl ester as white solid, mp. 127° C., MS:522(MH$^+$).

(2S,4R)-2-hydroxymethyl-4-tritylsulfanyl-pyrrolidine-1-carboxylic acid tert-butyl ester gave (2S,4R)-2-methanesulfonyloxymethyl-4-tritylsulfanyl-pyrrolidine-1-carboxylic acid tert-butyl ester as white foam, MS: 554 (MH$^+$);

(2R,4R)-2-[1-(naphthalene-2-sulfonyl)-4-tritylsulfanyl-pyrrolidin-2-yl]-ethanol gave (2R,4R)-methanesulfonic acid 2-[1-(naphthalene-2-sulfonyl)-4-tritylsulfanyl-pyrrolidin-2-yl]-ethyl ester as white foam, MS: 658 (MH$^+$).

(2R,4R)-3-[4-(4-methoxy-benzylsulfanyl)-pyrrolidin-2-yl]-propan-1-ol gave with 2.2 equivalent, methansulfonylchloride and 2 equivalent DMAP (2R,4R)-methanesulfonic acid 3-[1-methanesulfonyl-4-(4-methoxy-benzylsulfanyl)-pyrrolidin-2-yl]-propyl ester, MS: 438 (MH$^+$).

Method A: 200 mg (0.31 mmol) Methanesulfonic acid (2S,4R)-1-(naphthalene-2-sulfonyl)-4-tritylsulfanyl-pyrrolidin-2-ylmethyl ester and 47 mg (0.31 mmol, 1.0 eq) sodium iodide were dissolved in 5 ml ethyl isonipecotate, heated to 100° C. for 3 h and the excess of the amine was removed under vacuum. The resulting residue was dissolved in EtOAc and 5% aqueous NaHCO$_3$ solution, the layers were separated, the organic one was extracted with water (3×) and washed with brine, dried over Na$_2$SO$_4$, and evaporated.

The crude material (2S,4R)-1-[1-(Naphthalene-2-sulfonyl)-4-tritylsulfanyl-pyrrolidin-2-ylmethyl]-piperidine-4-carboxylic acid ethyl ester was dissolved in 6.5 ml acetonitrile and 3 ml TFA, 0.5 ml (3.1 mmol) triethylsilane were added, and the reaction was stirred at 40° C. for 3 h. 40 ml aqueous saturated NaHCO$_3$ solution were added carefully, the layers were separated and the inorganic one was extracted with EtOAc. The organic layer was washed with water and brine, dried over Na$_2$SO$_4$ and evaporated. The residue was purified by flash chromatography on silica gel with EtOAc/hexane 1:2 yielding 45 mg (30%, 2steps) of (2S,4R)-1-[4-mercapto-1-(naphthalene-2-sulfonyl)-pyrrolidin-2-ylmethyl]-piperidine-4-carboxylic acid ethyl ester as colorless oil, MS: 463(MH$^+$).

In a similar manner, but replacing ethyl isonipecotate (5 ml, 100° C., 3 h) with piperidine (5 ml, 100° C., 2 h), aniline (4 ml, 100° C., 12 h), benzylamine (4 ml, 100° C., 8 h), 2-fluorobenzylamine (2 ml, 100° C., 8 h), N-benzylmethylamine (4 ml, 100 C. 8 h), diethylamine (4 ml, 100° C., 8 h), 2,4-difluoro benzylamine (3 ml, 100° C., 8 h), 2,5-difluorobenzylamine (3 ml, 100° C., 8 h), N-ethyl-o-fluorobenzylamine (3 ml, 100° C., 12 h), 2,3-difluorobenzylamine (3 ml, 100° C., 12 h), 2,3,5-triflorobenzylamine (2 ml, 100° C., 12 h), 2,3,6-trifluorobenzylamine (2 ml, 100° C., 12 h), N-methyl-2-phenyl-ethylamine (4 ml, 100° C., 2 h), phenethylamine (4 ml, 100° C., 2 h), i) dibenzylamine (4 ml, 100° C., 12 h.

The following compounds were prepared:

(3R,5S)-1-(naphthalene-2-sulfonyl)-5-piperidin-1-ylmethyl-pyrrolidine-3-thiol as white solid, mp 90° C., MS: 391 (MH$^+$);

(3R,5S)-1-(naphthalene-2-sulfonyl)-5-phenylaminomethyl-pyrrolidine-3-thiol as orange oil, MS: 399 (MH$^+$);

(3R,5S)-5-(benzylamino-methyl)-1-(naphthalene-2-sulfonyl)-pyrrolidine-3-thiol as colorless solid, mp 90° C., MS: 413 (MH$^+$);

(3R,5S)-5-[(2-fluoro-benzylamino)-methyl]-1-(naphthalene-2-sulfonyl)-pyrrolidine-3-thiol as colorless oil, MS: 431 (MH$^+$);

(3R,5S)-5-[(benzyl-methyl-amino)-methyl]-1-(naphthalene-2-sulfonyl)-pyrrolidine-3-thiol as colorless oil, MS: 427 (MH$^+$);

(3R,5S)-5-diethylaminomethyl-1-(naphthalene-2-sulfonyl)-pyrrolidine-3-thiol as light yellow oil, MS: 379 (MH$^+$);

(3R,5S)-5-[(2,4-difluoro-benzylamino)-methyl]-1-(naphthalene-2-sulfonyl)-pyrrolidine-3-thiol as orange oil, MS: 449 (MH$^+$);

(3R,5S)-5-[(2,5-difluoro-benzylamino)-methyl]-1-(naphthalene-2-sulfonyl)-pyrrolidine-3-thiol as orange oil, MS: 449 (MH$^+$);

(3R,5S)-5-{[ethyl-(2-fluoro-benzyl)-amino]-methyl}-1-(naphthalene-2-sulfonyl)-pyrrolidine-3-thiol as yellow oil, MS: 459 (MH$^+$);

(3R,5S)-5-[(2,3-difluoro-benzylamino)-methyl]-1-(naphthalene-2-sulfonyl)-pyrrolidine-3-thiol as orange oil, MS: 449 (MH$^+$);

(3R,5S)-1-(naphthalene-2-sulfonyl)-5-[(2,3,5-trifluoro-benzylamino)-methyl]-pyrrolidine-3-thiol as colorless oil, MS: 467 (MH$^+$);

(3R,5S)-1-(naphthalene-2-sulfonyl)-5-[(2,3,6-trifluoro-benzylamino)-methyl]-pyrrolidine-3-thiol as orange oil, MS: 467 (MH$^+$);

(3R,5S)-5-[(methyl-phenethyl-amino)-methyl]-1-(naphthalene-2-sulfonyl)-pyrrolidine-3-thiol as orange oil, MS: 441 (MH$^+$);

(3R,5S)-1-(naphthalene-2-sulfonyl)-5-(phenethylamino-methyl)-pyrrolidine-3-thiol as orange oil, MS: 427 (MH$^+$).

(3R,5S)-5-[(dibenzylamino)-methyl]-1-(naphthalene-2-sulfonyl)-pyrrolidine-3-thiol as white gum, MS: 503 (MH$^+$).

Method B: A slurry of 300 mg (0.73 mmol) (2S,4R)-methanesulfonic acid 1-methanesulfonyl-4-(4-methoxy-benzylsulfanyl)-pyrrolidin-2-ylmethyl ester and 109 mg (0.73 mmol) of NaI in 5 ml benzylamine was heated in the oil bath to 100° C., evaporated in the kugelrohr at 50–70° C./1 Torr and extracted with aqueous saturated NaHCO$_3$ solution/Et$_2$O (3×). The organic phase was dried over Na$_2$SO$_4$, evaporated and the residue was crystallized from Et$_2$O/pentane at −20° C. to give 200 mg (65%) of (2S,4R)-benzyl-[1-methanesulfonyl-4-(4-methoxy-benzylsulfanyl)-pyrrolidin-2-ylmethyl]-amine, mp 63–64° C., MS: 421 (MH$^+$).

(Method 2): 100 mg (0.24 mmol) of (2S,4R)-benzyl-[1-methanesulfonyl-4-(4-methoxy-benzylsulfanyl)-pyrrolidin-2-ylmethyl]-amine was dissolved in 8.5 ml TFA and treated at 0° C. with 0.38 ml (2.38 mmol) triethylsilane. The reaction was warmed up over night, heated 1.5 h at 80° C. and evaporated, partitioned between water (10 ml)/Et$_2$O (2×10 ml). The water was lyophilized to give 90 mg (91%) of (3R,5S)-5-(benzylamino-methyl)-1-methanesulfonyl-pyrrolidine-3-thiol trifluoro-acetate, MS: 301 (MH$^+$).

In analogy: Methanesulfonic acid (2R,4R)-2-(1-methanesulfonyl-4-tritylsulfanyl-pyrrolidin-2-yl)-ethyl ester and aniline gave (3R,5R)-1-methanesulfonyl-5-(2-phenyl-amino-ethyl)-pyrrolidine-3-thiol trifluoro-acetate (1:1), mp 122.5–123° C., MS: 301 (MH$^+$);

(2S,4R)-methanesulfonic acid 1-methanesulfonyl-4-(4-methoxy-benzylsulfanyl)-pyrrolidin-2-ylmethyl ester with N-benzylmethylamine gave (3R,5S)-5-[(benzyl-methyl-amino)-methyl]-1-methanesulfonyl-pyrrolidine-3-thiol trifluoro-acetate, MS: 315 (MH$^+$).

Method C: A solution of 130 mg (0.257 mmol) (2R,4R)-2-(3-methane-sulfonyloxy-propyl)-4-(4-methoxy-benzylsulfanyl)-pyrrolidine-1-carboxylic acid butyl ester, 0.037 ml (0.514 mmol) pyrrole and 38.6 mg (0.257 mmol) NaI in 0.4 ml DMF was treated at 0° C. with 22.4 mg (0.514 mmol) 55% NaH and warmed up over night to room temperature. The reaction was neutralized with cooled aqueous saturated NH$_4$Cl and extracted (EtOAc 3×). The organic phase was washed with aqueous 10% NaCl, dried (Na$_2$SO$_4$) evaporated and purified by flash silica gel column (Hexane/EtOAc 9:1) to give 75 mg (68%) of (2R,4R)-4-(4-methoxy-benzylsulfanyl)-2-(3-pyrrol-1-yl-propyl)-pyrrolidine-1-carboxylic acid butyl ester, MS: 431 (MH$^+$).

(Method 1): A solution of 0.065 g (0.151 mmol) (2R,4R)-4-(4-methoxy-benzylsulfanyl)-2-(3-pyrrol-1-yl-propyl)-pyrrolidine-1-carboxylic acid butyl ester was dissolved in 2 ml TFA, cooled to 0° C. and treated with 0.24 ml (1.51 mmol) triethylsilane, stirred for 22 h at room temperature and treated again with 0.24 ml (1.51 mmol) triethylsilane after further 30 h the evaporated residue was purified by flash silica gel column (CH$_2$Cl$_2$/EtOAc 99:1) to give 10 mg of (2S,4R)-4-mercapto-2-(3-pyrrol-1-yl-propyl)-pyrrolidine-1-carboxylic acid butyl ester, MS: 311 (MH$^+$).

In analogy: (2R,4R)-2-(3-methanesulfonyloxy-propyl)-4-(4-methoxy-benzylsulfanyl)-pyrrolidine-1-carboxylic acid butyl ester with imidazol gave (2S,4R)-2-(3-imidazol-1-yl-propyl)-4-mercapto-pyrrolidine-1-carboxylic acid butyl ester, MS: 312 (MH$^+$);

(2R,4R)-methanesulfonic acid 3-[1-methanesulfonyl-4-(4-methoxy-benzylsulfanyl)-pyrrolidin-2-yl]-propyl ester with pyrrole gave (3R,5R)-1-methanesulfonyl-5-(3-pyrrol-1-yl-propyl)-pyrrolidine-3-thiol, MS: 289 (MH$^+$).

Example 3
Thioether

A slurry of 300 mg (0.73 mmol) (2S,4R)-methanesulfonic acid 1-methanesulfonyl-4-(4-methoxy-benzylsulfanyl)-pyrrolidin-2-ylmethyl ester and 109 mg (0.73 mmol) of NaI in 3 ml DMF at 0° C. was treated with 0.35 ml (2.93 mmol) benzylmercaptane and 96 mg (2.2 mmol) 55% NaH. The reaction was warmed up during 2 h to room temperature: and worked up with aqueous saturated NH$_4$Cl solution/EtOAc (3×). The organic phase was dried over Na$_2$SO$_4$, evaporated and purified by crystallization (Et$_2$O) to give 158 mg (49%) of (2S,4R)-2-benzylsulfanylmethyl-1-methanesulfonyl-4-(4-methoxy-benzylsulfanyl)-pyrrolidine, mp 69–71° C., MS: 438 (MH$^+$).

(TFA/triethylsilane for not labile methoxybenzylsulfanyl, Method 2): 100 mg (0.23 mmol) of (2S,4R)-2-benzylsulfanylmethyl-1-methanesulfonyl-4-(4-methoxy-benzylsulfanyl)-pyrrolidine was dissolved in 8.2 ml TFA and treated at 0° C. with 0.35 ml (2.38 mmol) triethylsilane. The reaction was warmed up over night, heated 2.5 min at 80° C. and evaporated. Flash silica gel column (CH$_2$Cl$_2$/EtOAc 99:1) gave 15 mg (21%) of (3R,5S)-5-benzylsulfanylmethyl-1-methanesulfonyl-pyrrolidine-3-thiol, mp 101.5–103.5° C., MS: 318 (MH$^+$).

Example 4
Amines (via Azide)

To a solution of 10.12 g (19.4 mmol) methanesulfonic acid (2S,4R)-4-(4-methoxy-benzylsulfanyl)-1-(naphthalene-2-sulfonyl)-pyrrolidin-2-ylmethyl in 65 ml DMF were added 1.78 g (27.4 mmol, 1.4 eq) NaN$_3$. The solution was stirred at 80° C. overnight, recooled and water was added. The phases were separated and the inorganic one was extracted with Et$_2$O, the combined organic layers were washed with water and brine, dried over Na$_2$SO$_4$ and evaporated. Trituration with hexane gave 7.8 g (86%) (2S,4R)-2-azidomethyl-4-(4-methoxy-benzylsulfanyl)-1-(naphthalene-2-sulfonyl)-pyrrolidine as white solid, mp 143° C., MS: 469 (MH$^+$).

Analogously the following compounds were prepared:
From methanesulfonic acid (2S,4R)-1-(naphthalene-2-sulfonyl)-4-tritylsulfanyl-pyrrolidin-2-ylmethyl ester: (2S,4R)-2-azidomethyl-1-(naphthalene-2-sulfonyl)-4-tritylsulfanyl-pyrrolidine as white foam, MS: 591 (MH$^+$).

From (2S,4R)-2-methanesulfonyloxymethyl-4-tritylsulfanyl-pyrrolidine-1-carboxylic acid tert-butyl ester: (2S,4R)-2-azidomethyl-4-tritylsulfanyl-pyrrolidine-1-carboxylic acid tert-butyl ester as yellow oil, MS: 501 (MH$^+$).

From (2S,4R)-methanesulfonic acid 1-methanesulfonyl-4-(4-methoxy-benzylsulfanyl)-pyrrolidin-2-ylmethyl ester: (2S,4R)-2-azidomethyl-1-methanesulfonyl-4-(4-methoxy-benzylsulfanyl)-pyrrolidine as white crystalline, MS: 357 (MH$^+$).

From methanesulfonic acid (2R,4R)-2-(1-methanesulfonyl-4-tritylsulfanyl-pyrrolidin-2-yl)-ethyl ester: (2S,4R)-2-(2-azido-ethyl)-1-methanesulfonyl-4-tritylsulfanyl-pyrrolidine as light yellow foam, MS: 493 (MH$^+$).

From (2R,4R)-methanesulfonic acid 2-[i-(naphthalene-2-sulfonyl)-4-tritylsulfanyl-pyrrolidin-2-yl]-ethyl ester: (2R,4R)-2-(2-azido-ethyl)-1-(naphthalene-2-sulfonyl)-4-tritylsulfanyl-pyrrolidine as white foam, MS: 605 (MH$^+$).

Example 4.a
Methylamine-optimization
Staudinger-NH$_2$ Formation 1.7 g (2.9 mmol) (2S,4R)-2-Azidomethyl-1-(naphthalene-2-sulfonyl)-4-tritylsulfanyl-pyrrolidine were treated with 2.3 g (8.8 mmol, 3 eq) of triphenyl phosphine in 12 ml THF and 0.5 ml H$_2$O for 2 days at RT. The solution was diluted with EtOAc, extracted with H$_2$O and aqueous saturated NaHCO$_3$ solution, washed with brine, dried over Na$_2$SO$_4$ and evaporated. The residue was purified by flash chromatography on silica gel with CH$_2$Cl$_2$/MeOH 95:5 yielded 1.6 g (99%) (2S,4R)-C-[1-(naphthalene-2-sulfonyl)-4-tritylsulfanyl-pyrrolidin-2-yl]-methylamine as white foam, MS: 565 (MH$^+$).

Analogously the following compounds were prepared:
From (2S,4R)-2-azidomethyl-4-(4-methoxy-benzylsulfanyl)-1-(naphthalene-2-sulfonyl)-pyrrolidine:

(2S,4R)—C-[4-(4-methoxy-benzylsulfanyl)-1-(naphthalene-2-sulfonyl)-pyrrolidin-2-yl]-methylamine as light yellow solid, mp 88–89° C., MS: 443 (MH$^+$).

From (2R,4R)-2-(2-azido-ethyl)-1-(naphthalene-2-sulfonyl)-4-tritylsulfanyl-pyrrolidine: (2R,4R)-2-[1-(naphthalene-2-sulfonyl)-4-tritylsulfanyl-pyrrolidin-2-yl]-ethylamine as white foam MS: 579 (MH$^+$).

Reductive Amination 250 mg (0.56 mmol) (2S,4R)—C-[1-(naphthalene-2-sulfonyl)-4-tritylsulfanyl-pyrrolidin-2-yl]-methylamine and 58 μl (0.5 mmol) o-tolualdehyde in 1 ml MeOH were treated with a solution of 57 mg (0.3 mmol, 0.6 eq) SnCl$_2$ and 38 mg (0.6 mmol, 1.2 eq) NaBH$_3$CN in 1 ml MeOH at room temperature and subsequent cleavage of the protecting group (Method 3) gave (3R,5S)-5-[(2-methyl-benzylamino)-methyl]-1-(naphthalene-2-sulfonyl)-pyrrolidine-3-thiol as white solid, mp 122° C., MS: 427 (MH$^+$).

Analogously the following compounds were prepared:

From (2S,4R)—C-[1-(naphthalene-2-sulfonyl)-4-tritylsulfanyl-pyrrolidin-2-yl]-methylamine a) and 2,4-dimethoxybenzaldehyde and subsequent cleavage of the protecting group (trityl deprotection, Method 3) (3R,5S)-5-[(2,4-dimethoxy-benzylamino)-methyl]-1-(naphthalene-2-sulfonyl)-pyrrolidine-3-thiol as colorless oil, MS: 473 (MH$^+$).

b) and 4-pyridinecarboxaldehyde and subsequent cleavage of the protecting group (trityl deprotection, Method 3) (3R,5S)-1-(naphthalene-2-sulfonyl)-5-[[(pyridin-4-ylmethyl)-amino]-methyl]-pyrrolidine-3-thiol as yellow oil, MS: 414 (MH$^+$).

c) and 3-pyridinecarboxaldehyde and subsequent cleavage of the protecting (Method 3) (3R,5S)-1-(naphthalene-2-sulfonyl)-5-[[(pyridin-3-ylmethyl)-amino]-methyl]-pyrrolidine-3-thiol as colorless oil, MS: 414 (MH$^+$).

d) and 3-fluoro-p-anisaldehyde and subsequent cleavage of the protecting group (trityl deprotection, Method 3) (3R,5S)-5-[(3-fluoro-4-methoxy-benzylamino)-methyl]-1-(naphthalene-2-sulfonyl)-pyrrolidine-3-thiol as colorless oil, MS: 461 (MH$^+$).

e) and benzyloxyacetaldehyde and subsequent cleavage of the protecting group (trityl deprotection, Method 3) (3R,5S)-5-[(2-benzyloxy-ethylamino)-methyl]-1-(naphthalene-2-sulfonyl)-pyrrolidine-3-thiol as colorless oil, MS: 457 (MH$^+$).

f) and 2-thiophenecarboxaldehyde and subsequent cleavage of the protecting group (trityl deprotection, Method 3) (3R,5S)-1-(naphthalene-2-sulfonyl)-5-{[(thiophen-2-ylmethyl)-amino]-methyl}-pyrrolidine-3-thiol as colorless oil, MS: 419 (MH$^+$).

g) and cyclohexanecarboxaldehyde and subsequent cleavage of the protecting group (trityl deprotection, Method 3) (3R,5S)-5-[(cyclohexylmethyl-amino)-methyl]-1-(naphthalene-2-sulfonyl)-pyrrolidine-3-thiol as colorless oil, MS: 418 (MH$^+$).

From (2S,4R)-C-[4-(4-methoxy-benzylsulfanyl)-1-(naphthalene-2-sulfonyl)-pyrrolidin-2-yl]-methylamine and isobutylaldehyde and subsequent cleavage of the protecting group (Method 2) (3R,5S)-5-(isobutylamino-methyl)-1-(naphthalene-2-sulfonyl)-pyrrolidine-3-thiol as white solid, mp 73° C., MS: 379 (MH$^+$).

From (2R,4R)-2-[1-(naphthalene-2-sulfonyl)-4-tritylsulfanyl-pyrrolidin-2-yl]-ethylamine and 2,5-difluorobenzaldehyde and subsequent cleavage of the protecting group (3R,5R)-5-[2-(2,5-difluoro-benzylamino)-ethyl]-1-(naphthalene-2-sulfonyl)-pyrrolidine-3-thiol as colorless oil, MS: 463 (MH$^+$).

From (2S,4R)-2-azidomethyl-4-tritylsulfanyl-pyrrolidine-1-carboxylic acid tert-butyl ester was prepared via (2S,4R)-2-aminomethyl-4-tritylsulfanyl-pyrrolidine-1-carboxylic acid tert-butyl ester [as light brown foam, MS: 475 (MH$^+$)] and further reaction with 2,5-difluoro benzaldehyde analogously to reductive amination gave (2S,4R)-2-[(2,5-difluoro-benzylamino)-methyl]-4-tritylsulfanyl-pyrrolidine-1-carboxylic acid tert-butyl ester as colorless oil MS: 601 (MH$^+$) which was treated according to trityl cleavage (method 5) to give (2S,4R)-2-[(2,5-difluoro-benzylamino)-methyl]-4-mercapto-pyrrolidine-1-carboxylic acid tert-butyl ester as colorless liquid MS: 359 (MH$^+$).

Example 4.b

N-Pyrrolidine: Carbamates (2S,4R)-2-azidomethyl-4-tritylsulfanyl-pyrrolidine-1-carboxylic acid tert-butyl with TFA in CH$_2$Cl$_2$ (following the general method for a selective BOC-deprotection) gave (2S,4R)-2-azidomethyl-4-tritylsulfanyl-pyrrolidine as light yellow oil, MS: 501 (MH$^+$).

(2S,4R)-2-azidomethyl-4-tritylsulfanyl-pyrrolidine and benzyl chloroformate/N-ethyldiisopropylamine in CH$_2$Cl$_2$ (see cabamate synthesis, Method A)—followed by Staudinger reduction gave (2S,4R)-2-aminomethyl-4-tritylsulfanyl-pyrrolidine-1-carboxylic acid benzyl ester as white foam, MS: 509 (MH$^+$).

(2S,4R)-2-aminomethyl-4-tritylsulfanyl-pyrrolidine-1-carboxylic acid benzyl ester and 2,5-difluorobenzaldehyde and subsequent cleavage of the trityl protecting group analogously to reductive amination and deprotection gave (2S,4R)-2-[(2,5-difluoro-benzylamino)-methyl]-4-mercapto-pyrrolidine-1-carboxylic acid benzyl ester as colorless oil, MS: 393 (MH$^+$).

In a similar manner, the following compounds were prepared from (2S,4R)-2-azidomethyl-4-tritylsulfanyl-pyrrolidine, but replacing benzyl chloroformate with 4-fluorophenyl chloroformate, isopropyl chloroformate, chloroformic acid 2-naphthyl ester, 1,4-benzodioxan-5-yl chloroformate[Eitel & Hammann, I. *Benzodioxan-N-methylcarbamates useful as insecticides or acaricides*. S. African, 14 pp. ZA 6800512 680627.] and in situ prepared chloroformates from 1-naphthalene ethanol and 2-naphthalene ethanol, respectively, (by treatment with trichloromethyl chloroformate, quinoline in CH$_2$Cl$_2$, see Carbamate, Method B).

(2S,4R)-2-[(2,5-difluoro-benzylamino)-methyl]-4-mercapto-pyrrolidine-1-carboxylic acid 4-fluoro-phenyl ester as colorless oil, MS: 397 (MH$^+$).

(2S,4R)-2-[(2,5-difluoro-benzylamino)-methyl]-4-mercapto-pyrrolidine-1-carboxylic acid isopropyl ester as colorless oil, MS: 345 (MH$^+$).

(2S,4R)-2-[(2,5-difluoro-benzylamino)-methyl]-4-mercapto-pyrrolidine-1-carboxylic acid naphthalen-2-yl ester as colorless oil, MS: 429 (MH$^+$).

(2S,4R)-2-[(2,5-difluoro-benzylamino)-methyl]-4-mercapto-pyrrolidine-1-carboxylic acid 2,3-dihydro-benzo[1,4]dioxin-5-yl ester as colorless oil, MS: 437 (MH$^+$).

(2S,4R)-2-[(2,5-difluoro-benzylamino)-methyl]-4-mercapto-pyrrolidine-1-carboxylic acid butyl ester as colorless oil, MS: 359 (MH+).

(2S,4R)-2-[(2,5-Difluoro-benzylamino)-methyl]-4-mercapto-pyrrolidine-1-carboxylic acid 2-naphthalen-1-yl-ethyl ester as colorless oil, MS: 457 (MH+).

(2S,4R)-2-[(2,5-Difluoro-benzylamino)-methyl]-4-mercapto-pyrrolidine-1-carboxylic acid 2-naphthalen-2-yl-ethyl ester ester as colorless oil, MS: 457 (MH+).

Example 4.c
N-Pyrrolidine: Sulfamides

To 4.2 ml (48.65 mmol, 1.2 eq) oxalyl chloride in 100 ml $CH_2Cl_2$ were added 6.5 ml (89.19 mmol, 2.2 eq) DMSO in 20 ml $CH_2Cl_2$ at −65° C., followed after 10 min by 14.33 g (40.54 mmol, 1.0 eq) (2S,4R)-2-hydroxymethyl-4-(4-methoxy-benzylsulfanyl)-pyrrolidine-1-carboxylic acid tert-butyl ester in 60 ml $CH_2Cl_2$ over a period of 20 min. The solution was stirred at −68° C. for 1.5 h before 28 ml (162.16 mmol, 4 eq) iPr$_2$NEt were added, and the reaction mixture was warmed to room temperature. The solution was extracted with 1M $KHSO_4$, the combined inorganic phases were extracted with $CH_2Cl_2$ and the organic phase dried over $Na_2SO_4$ and evaporated, yielding 14.18 g (99%) (2S,4R)-2-formyl-4-(4-methoxy-benzylsulfanyl)-pyrrolidine-1-carboxylic acid tert-butyl ester. The crude product was subjected to the following reaction without further purification.

To 14.18 g (40.54 mmol) (2S,4R)-2-formyl-4-(4-methoxy-benzylsulfanyl)-pyrrolidine-1-carboxylic acid tert-butyl ester in 250 ml $CH_2Cl_2$ were added 4.88 g $MgSO_4$, followed by 4.8 ml (40.9 mmol, 1.0 eq) 2,5-difluoro-benzylamine. The suspension was stirred at RT overnight, filtered and evaporated. The crude yellow oil was purified by flash chromatography with EtOAc/hexane 1:3 yielding 17.31 g (2S,4R)-2-[(2,5-difluoro-benzylimino)-methyl]-4-(4-methoxy-benzylsulfanyl)-pyrrolidine-1-carboxylic acid tert-butyl ester (90%, 2 steps) as yellow oil.

To 17.31 g (36.32 mmol) (2S,4R)-2-[(2,5-difluoro-benzylimino)-methyl]-4-(4-methoxy-benzylsulfanyl)-pyrrolidine-1-carboxylic acid tert-butyl ester in 120 ml MeOH were added 1.64 g (43.58 mmol, 1.2 eq) $NaBH_4$ slowly at 40° C. The solution was stirred at that temperature for additional 90 min, water was added carefully and the solution was concentrated. The residue was redissolved in EtOAc and washed with $NaHCO_3$ and brine, dried over $Na_2SO_4$ and evaporated. Flash chromatography with EtOAc/hexane 1:1 yielded 11.57 g (67%) (2S,4R)-2-[(2,5-difluoro-benzylamino)-methyl]-4-(4-methoxy-benzylsulfanyl)-pyrrolidine-1-carboxylic acid tert-butyl ester as yellow oil, MS: 479 (MH+).

To 3.19 g (6.67 mmol, 1 eq) (2S,4R)-2-[(2,5-difluoro-benzylamino)-methyl]-4-(4-methoxy-benzylsulfanyl)-pyrrolidine-1-carboxylic acid tert-butyl ester in 10 ml $CH_2Cl_2$ were added 1.35 ml (8.0 mmol, 1.2 eq) EtNiPr$_2$, followed by 2.07 g (8.0 mmol, 1.2 eq) 9-fluorenylmethyl chloroformate and a catalytic amount of DMAP at 0° C. The solution was stirred at room temperature overnight, 5% $NaHCO_3$ solution was added (pH 9), the layers were separated and the inorganic one was extracted with $CH_2Cl_2$. The combined organic layers were washed with 1M $KHSO_4$ and brine, dried over $Na_2SO_4$ and evaporated. The crude product was purified by flash chromatography with EtOAc/hexane 1:3 as eluent yielding 3.81 g (82%) (2S,4R)-2-{[(2,5-difluoro-benzyl)-(9H-fluoren-9-ylmethoxy-carbonyl)-amino]-methyl}-4-(4-methoxy-benzylsulfanyl)-pyrrolidine-1-carboxylic acid tert-butyl ester as white foam, which was subjected to the next reaction directly.

To 2.27 g (3.24 mmol) (2S,4R)-2-{[(2,5-Difluoro-benzyl)-(9H-fluoren-9-ylmethoxycarbonyl)-amino]-methyl}-4-(4-methoxy-benzylsulfanyl)-pyrrolidine-1-carboxylic acid tert-butyl ester in 10 ml $CH_2Cl_2$ were added 3.4 ml TFA at 0° C., and the solution was stirred at room temperature for 2 h. The solvent was evaporated and the crude oil redissolved and evaporated successively with toluene, hexane and $Et_2O$ yielding 2.46 g (2S,4R)-(2,5-difluoro-benzyl)-[4-(4-methoxy-benzylsulfanyl)-pyrrolidin-2-ylmethyl]-carbamic acid 9H-fluoren-9-ylmethyl ester as TFA salt as brown oil.

To 300 mg (0.42 mmol) (2S,4R)-2,5-difluoro-benzyl)-[4-(4-methoxy-benzylsulfanyl)-pyrrolidin-2-ylmethyl]-carbamic acid 9H-fluoren-9-ylmethyl ester as TFA salt in 5 ml $CH_2Cl_2$ were added 290 µl (1.68 mmol, 4 eq) EtNiPr$_2$, followed by 121 mg (0.59 mmol, 1.4 eq) benzylsulfamoyl chloride at 0° C. The solution was stirred at room temperature for 48 h, 1M $KHSO_4$ was added, the layers were separated and the inorganic one was extracted with $CH_2Cl_2$. The combined organic layers were washed with 1M $KHSO_4$ and brine, dried over $Na_2SO_4$ and evaporated. The crude product was dissolved in 4.2 ml $Et_2NH$:THF (1:1) at 0° C. and stirred 5 h at room temperature. The solvent was evaporated, the residue redissolved and evaporated twice with hexane and dried in vacuum. The brown oil was dissolved in 4 ml TFA and 0.7 ml (4.2 mmol) $Et_3SiH$ and stirred at 80° C. for 2 h. The solution was concentrated, redissolved in EtOAc and $NaHCO_3$ solution, the layers were separated and the inorganic one was extracted with EtOAc, the combined organic ones were washed with brine, dried over $Na_2SO_4$ and evaporated. The crude product was purified purified by flash chromatography with $CH_2Cl_2$/MeOH 95:5 yielding 16.8 mg (10%, 3 steps) (2S,4R)-2-[(2,5-difluoro-benzylamino)-methyl]-4-mercapto-pyrrolidine-1-sulfonic acid benzylamide as white oil, MS: 427 (MH+).

In a similar manner, but replacing benzylsulfamoyl chloride with cyclopropyl-sulfamoyl chloride and n-butylsulfamoyl chloride the following compounds were prepared:

(2S,4R)-2-[(2,5-difluoro-benzylamino)-methyl]-4-mercapto-pyrrolidine-1-sulfonic acid cyclopropylamide as colorless oil, MS: 377 (MH+).

(2S,4R)-2-[(2,5-difluoro-benzylamino)-methyl]-4-mercapto-pyrrolidine-1-sulfonic acid butylamide as colorless oil, MS: 393 (MH+).

Example 4.c
N-Pyrrolidines: Ureas

From (2S,4R)-2-Azidomethyl-4-tritylsulfanyl-pyrrolidine-1-carboxylic acid tert-butyl ester was prepared (2S,4R)-2-azidomethyl-4-tritylsulfanyl-pyrrolidine according to BOC-cleavage example general method B (variation 0° C., 2 h).

280 mg (0.7 mmol) (2S,4R)-2-azidomethyl-4-tritylsulfanyl-pyrrolidine were treated with 87 µM (0.77 mol, 1.1 eq) butyl isocyanate in 5 ml THF at 0° C., and the solution was stirred at RT for 45 min. The solvent was evaporated, and the residue was purified by flash chromatography yielding 278 mg (80%) (2S,4R)-2-azidomethyl-4-tritylsulfanyl-pyrrolidine-1-carboxylic acid butylamide as white foam.

275 mg (0.55 mmol) (2S,4R)-2-azidomethyl-4-tritylsulfanyl-pyrrolidine-1-carboxylic acid butylamide in 8 ml ethanol was treated with 83 mg (2.2 mmol) $NaBH_4$ at 80° C. for 18 h. Additional 175 mg (4.6 mmol) $NaBH_4$ were added in portions, and the reaction was stirred at 80° C. until no starting material could be detected. The solution was poured into a saturated $NH_4Cl$ solution, and was extracted with EtOAc, the organic phase was washed with brine, dried over $Na_2SO_4$ and evaporated. Column chromatography yielded 213 mg (82%) (2S,4R)-2-aminomethyl-4-tritylsulfanyl-pyrrolidine-1-carboxylic acid butylamide as white foam, which was directly subjected to the following reactions according to reductive amination with 2,5-difluoro-benzaldehyde (example 4a) and subsequent trityl cleavage (method 3) yielding (2S,4R)-2-[(2,5-difluoro-benzylamino)-methyl]-4-mercapto-pyrrolidine-1-carboxylic acid butylamide as colorless oil, MS:358 ($MH^+$).

Analogously, the following compounds were prepared from (2S,4R)-2-azidomethyl-4-tritylsulfanyl-pyrrolidine and 2-fluorophenyl isocyanate or benzylisocyanate and 2,5-difluorobenzaldehyde.

(2S,4R)-2-[(2,5-difluoro-benzylamino)-methyl]-4-mercapto-pyrrolidine-1-carboxylic acid (2-fluoro-phenyl)-amide as white solid, mp 126° C., MS: 396 ($MH^+$).

(2S,4R)-2-[(2,5-difluoro-benzylamino)-methyl]-4-mercapto-pyrrolidine-1-carboxylic acid benzylamide as colorless oil, MS: 392 ($MH^+$).

Example 5
Second Substituent on Methylamine (Y=N)

6.94 g (14.5 mmol) (2S,4R)-2-[(2,5-difluoro-benzylamino)-methyl]-4-(4-methoxy-benzylsulfanyl)-pyrrolidine-1-carboxylic acid tert-butyl ester were dissolved in 170 ml acetonitrile and treated with 3 ml (20.3 mmol, 1.4 eq) t-butyl bromoacetate and 18.6 g (134.9 mmol, 9.3 mmol) $K_2CO_3$ at RT for 2d. The solid was removed by filtration, and the organic phase was washed with water and brine, dried over $Na_2SO_4$ and evaporated, yielding 9.02 g (quant) (2S,4R)-2-[[tert-butoxycarbonylmethyl-(2,5-difluoro-benzyl)-amino]-methyl]-4-(4-methoxy-benzylsulfanyl)-pyrrolidine-1-carboxylic acid tert-butyl ester as orange oil, MS: 593 ($MH^+$).

397 mg (0.67 mmol) (2S,4R)-2-[[tert-butoxycarbonylmethyl-(2,5-difluoro-benzyl)-amino]-methyl]-4-(4-methoxy-benzylsulfanyl)-pyrrolidine-1-carboxylic acid tert-butyl ester were treated with 4.2 ml 1N HCl in EtOAc at RT. The reaction mixture was concentrated and tituration with ether yielded 250 mg (76%) (2S,4R)-[(2, 5-difluoro-benzyl)-[4-(4-methoxy-benzylsulfanyl)-pyrrolidin-2-ylmethyl]-amino]-acetic acid tert-butyl ester as light brown solid, which was transformed to (2S,4R)-2-[[tert-butoxycarbonylmethyl-(2,5-difluoro-benzyl)-amino]-methyl]-4-(4-methoxy-benzylsulfanyl)-pyrrolidine-1-carboxylic acid butyl ester according to example 4b by treatment with butyl chloroformate.

250 mg (0.42 mmol) (2S,4R)-2-[[tert-butoxycarbonylmethyl-(2,5-difluoro-benzyl)-amino]-methyl]-4-(4-methoxy-benzylsulfanyl)-pyrrolidine-1-carboxylic acid butyl ester were treated with 670 μl (4.2 mmol, 10 eq) triethyl silane in 7.5 ml TFA at 80° C. for 1.5 h. The solvent was evaporated and the residue was redissolved in toluene and evaporated. The crude material was purified by flash chromatography yielding 85 mg (49%) (2S,4R)-2-[[carboxymethyl-(2,5-difluoro-benzyl)-amino]-methyl]-4-mercapto-pyrrolidine-1-carboxylic acid butyl ester as light brown oil, MS: 417 ($MH^+$).

Analogously, (2S,4R)-2-[(2,5-difluoro-benzylamino)-methyl]-4-tritylsulfanyl-pyrrolidine-1-carboxylic acid tert-butyl ester was treated with 2,5-difluoro-benzylbromide to give (2S,4R)-2-{[bis-(2,5-difluoro-benzyl)-amino]-methyl}-4-tritylsulfanyl-pyrrolidine-1-carboxylic acid tert-butyl ester which was treated with TFA according to general method B (variation 0° C. to RT) to give (2S,4R)-bis-(2,5-difluoro-benzyl)-(4-tritylsulfanyl-pyrrolidin-2-ylmethyl)-amine yellow oil, MS: 627 ($MH^+$).

Using the procedures described for the reactions in 4a and 4c the following compounds were prepared from (2S,4R)-bis-(2,5-difluoro-benzyl)-(4-tritylsulfanyl-pyrrolidin-2-ylmethyl)-amine and 2-naphthalene sulfonylchloride, N-butyl chloroformate, N-benzyl chloroformate, p-methoxyphenyl chloroformate, isopropyl chloroformate:

(2S,4R)-5-[[Bis-(2,5-difluoro-benzyl)-amino]-methyl]-1-(naphthalene-2-sulfonyl)-pyrrolidine-3-thiol as colorless oil, MS: 575 ($MH^+$).

(2S,4R)2-[[Bis-(2,5-difluoro-benzyl)-amino]-methyl]-4-mercapto-pyrrolidine-1-carboxylic acid butyl ester as colorless oil, MS: 485 ($MH^+$).

(2S,4R)-2-[[Bis-(2,5-difluoro-benzyl)-amino]-methyl]-4-mercapto-pyrrolidine-1-carboxylic acid benzyl ester as colorless oil, MS: 519 ($MH^+$).

(2S,4R)-2-[[Bis-(2,5-difluoro-benzyl)-amino]-methyl]-4-mercapto-pyrrolidine-1-carboxylic acid 4-methoxy-phenyl ester as colorless oil, MS: 535 ($MH^+$).

(2S,4R)-2-[[Bis-(2,5-difluoro-benzyl)-amino]-methyl]-4-mercapto-pyrrolidine-1-carboxylic acid isopropyl ester as colorless oil, MS: 471 ($MH^+$).

(2S,4R)-2-[[benzyloxycarbonyl-(2,5-difluoro-benzyl)-amino]-methyl]-4-tritylsulfanyl-pyrrolidine-1-carboxylic acid tert-butyl ester was treated according to trityl cleavage (method 5) to give (2S,4R)-2-[[benzyldxycarbonyl-(2,5-difluoro-benzyl)-amino]-methyl]-4-mercapto-pyrrolidine-1-carboxylic acid tert-butyl ester as colorless oil, MS: 493 ($MH^+$).

Example 6
Methylamine: Amides and Sulfonamides 11 g (83.9 mmol) L-Hydroxyproline were dissolved in 110 ml hexamethyldisilazane and heated to 120° C. overnight, cooled to room temperature and evaporated. The oily residue was dissolved in 110 ml THF, 16.5 ml (79.7 mmol, 0.95 eq) N-ethyl-morpholine was added, followed by 18.25 g (79.7 mmol, 0.95 eq) 2-naphthalenesulfonyl chloride in 130 ml THF over a period of 60 min. The solution was stirred at RT for 50 h, 15 ml ethanol were added and the solution was stirred for 15 min. At that time 400 ml of $Et_2O$ and 250 ml of aqueous saturated $NaHCO_3$ solution were added and the phases were separated. The aqueous layer was acidified and extracted with EtOAc, the combined organic layers were washed with brine, dried over $MgSO_4$ and concentrated. 17.39 g (65%) (2S,4R)-4-hydroxy-1-(naphthalene-2-sulfonyl)-pyrrolidine-2-carboxylic acid isolated as yellow solid, mp 140° C., MS: 321 (MH+).

38.97 g (121.4 mmol) (2S,4R)-4-hydroxy-1-(naphthalene-2-sulfonyl)-pyrrolidine-2-carboxylic acid were dissolved in 97 ml MeOH and 64.5 ml 1.75 M (112.8 mmol) HCl in MeOH were added and the solution heated to reflux for 3 h and concentrated. Trituration with hexane yielded 41.4 g (quant.) (2S,4R)-4-hydroxy-1-(naphthalene-2-sulfonyl)-pyrrolidine-2-carboxylic acid methyl ester as brown solid, MS: 335 (MH+).

29 ml (194 mmol, 1.6 eq) DBU were added to a suspension of 41.4 g (121.4 mmol) (2S,4R)-4-Hydroxy-1-(naphthalene-2-sulfonyl)-pyrrolidine-2-carboxylic acid methyl ester in 150 ml acetonitrile at 0° C. To the resulting solution 29.25 g (194 mmol, 1.6 eq) TBDMSCl were added in portions and the reaction was stirred at RT overnight. After concentrating the crude oil was purified by column chromatography with EtOAc/hexane 1:2 on silica gel to give 49.2 g (90%) (2S,4R)-4-(tert-butyl-dimethyl-silanyloxy)-1-(naphthalene-2-sulfonyl)-pyrrolidine-2-carboxylic acid methyl ester.

3.4 g (148 mmol, 95%, 2.7 eq) LiBH$_4$ were added in small portions to a solution of 24.5 g (54.6 mmol) (2S,4R)-4-(tert-Butyl-dimethyl-silanyloxy)-1-(naphthalene-2-sulfonyl)-pyrrolidine-2-carboxylic acid methyl ester in 1l THF at 0° C. The solution was stirred overnight, further 1.8 g (78 mmol, 95%, 1.4 eq) LiBH$_4$ were added and stirred for additional 48 h, before 10 ml acetic acid in 30 ml THF were added under cooling. 650 ml 5% NaHCO$_3$ solution were added slowly, the phases were separated, and the inorganic one was extracted with EtOAc. The combined organic ones were washed with brine, dried over Na$_2$SO$_4$ and evaporated yielding 22.3 g of a light yellow oil. An analytical sample was purified on silica gel with EtOAc/hexane 1:2 as solvent, (2S,4R)-[4-(tert-butyl-dimethyl-silanyloxy)-1-(naphthalene-2-sulfonyl)-pyrrolidin-2-yl]-methanol as white powder, MS: 422 (MH+).

24.34 g (57.73 mmol) (2S,4R)-[4-(tert-butyl-dimethyl-silanyloxy)-1-(naphthalene-2-sulfonyl)-pyrrolidin-2-yl]-methanol in 380 ml toluene were treated with 17.57 g (67 mmol, 1.16 eq) triphenylphosphine, 10.02 g (68.12 mmol, 1.18 eq) phthalimide. 13.8 ml (88.9 mmol, 1.5 eq) DEAD in 65 ml toluene were added to the solution over a period of 2.5 h, keeping the temperature below 3° C. The mixture was stirred at room temperature for 48 h, and recooled to 3° C. for further addition of 8.79 g (33.5 mmol, 0.58 eq) triphenylphosphine, 5.01 g (34 mmol, 0.59 eq) phthalimide and 6.9 ml (44.5 mmol, 0.75 eq) DEAD in 35 ml toluene. After stirring at 80° C. for 4 h and at room temperature for 3d, additional 8.79 g (33.5 mmol, 0.58 eq) triphenyl phosphine, 5.01 g (34 mmol, 0.59 eq) phthalimide and 6.9 ml (44.5 mmol, 0.75 eq) DEAD in 35 ml toluene were added, and the reaction heated to 80° C. for 3 h, recooled and diluted with EtOAc, extracted with 2M NaOH, aqueous saturated NaHCO$_3$, brine, dried over Na$_2$SO$_4$ and evaporated. The crude product was purified by column chromatography on silica gel yielding 15.6 g (50%) (2S,4R)-2-[4-(tert-butyl-dimethyl-silanyloxy)-1-(naphthalene-2-sulfonyl)-pyrrolidin-2-ylmethyl]-isoindole-1,3-dione and 6.0 g (25%) recovered starting material.

14.5 g (26.3 mmol) (2S,4R)-2-[4-(tert-butyl-dimethyl-silanyloxy)-1-(naphthalene-2-sulfonyl)-pyrrolidin-2-ylmethyl]-isoindole-1,3-dione in 145 ml THF were treated with 10.3 g (31.7 mmol, 1.2 eq) TBAF 3H$_2$O at RT for 1.5 h, the solvent was evaporated and the crude product purified by column chromatography on silica gel with a gradient EtOAc/hexane 4:1, EtOAc/CH$_2$Cl$_2$ 1:1, CH$_2$Cl$_2$/MeOH,9:1 yielding 5.5 g (45%) (2S,4R)-2-[4-hydroxy-1-(naphthalene-2-sulfonyl)-pyrrolidin-2-ylmethyl]-isoindole-1,3-dione as white crystalline, MS: 437 (MH+).

3.0 ml (21.7 mmol, 1.2 eq) triethylamine and 6.05 g (22.6 mmol, 1.2 eq) triphenylphosphine were added to a solution of 1.42 ml (21.7 mmol, 1.25 eq) methanesulfonic acid in 60 ml toluene, successively followed by a solution of 7.9 g (18.1 mmol) (2S,4R)-2-[4-hydroxy-1-(naphthalene-2-sulfonyl)-pyrrolidin-2-ylmethyl]-isoindole-1,3-dione in 80 ml toluene/THF (5/3) and 5.06 ml (23.6 mmol, 1.3 eq) DIAD. The suspension was heated to 80° C. for 6 h and stirred at room temperature overnight. After diluting the mixture with EtOAc and water, the phases were separated, and the inorganic one was extracted with EtOAc and CH$_2$Cl$_2$, the combined organic phases were washed with 1M KHSO$_4$ and brine, dried over Na$_2$SO$_4$ and evaporated. Column chromatography with a gradient of CH$_2$Cl$_2$: EtOAc 4:1 to 1:1 yielded 8.3 g (90%) of (3R,5S)-methanesulfonic acid 5-(1,3-dioxo-1,3-dihydro-isoindol-2-ylmethyl)-1-(naphthalene-2-sulfonyl)-pyrrolidin-3-yl ester as white crystals.

To 8.3 g (16.1 mmol) (3R,5S)-methanesulfonic acid 5-(1,3-dioxo-1,3-dihydro-isoindol-2-ylmethyl)-1-(naphthalene-2-sulfonyl)-pyrrolidin-3-yl ester in 210 ml DMF were added 2.82 g (24.2 mmol, 1.5 eq) potassium thioacetate and heated to 100° C. for 2.5 h. The mixture was concentrated under vacuum and the residue was redissolved in EtOAc and water, the layers were separated and the inorganic one was extracted with EtOAc (3×). The combined organic phases were extracted with saturated NaHCO$_3$ solution and brine, dried over Na$_2$SO$_4$ and evaporated. Purification with column chromatography on silica gel with EtOAc/hexane 1:1 as eluent yielded 6.8 g (85%) Thioacetic acid (2S,4R)-5-(1,3-dioxo-1,3-dihydro-isoindol-2-ylmethyl)-1-(naphthalene-2-sulfonyl)-pyrrolidin-3-yl as off white crystalline, mp 159° C., MS: 495 (MH+).

6.35 g (12.85 mmol) Thioacetic acid (2S,4R)-5-(1,3-dioxo-1,3-dihydro-isoindol-2-ylmethyl)-1-(naphthalene-2-sulfonyl)-pyrrolidin-3-yl ester treated with 320 ml 33% methylamine in ethanol (8.03 M, 2.57 mol) at room temperature for 2 days. The solvent was evaporated and the residue was purified on silica gel by column chromatography with CH$_2$Cl$_2$/MeOH/NH$_4$OH 90:10:1 yielding 2.26 g (55%) of C-[(2S,4R)-4-[(3R,5S)-5-aminomethyl-1-(naphthalene-2-sulfonyl)-pyrrolidin-3-yldisulfanyl]-1-(naphthalene-2-sulfonyl)-pyrrolidin-2-yl]-methylamine as off white foam, MS: 643 (MH+).

To a suspension of 127 mg (0.68 mmol, 1.05 eq) monomethylterephthalate in 11 ml CH$_2$Cl$_2$ were added 77 µl (0.68 mmol, 1.05 eq) 4-methyl morpholine, 222 mg (0.75 mmol, 1.2 Eq) TPTU and 200 mg (0.31 mmol) C-[(2S,4R)-4-[(3R,5S)-5-aminomethyl-1-(naphthalene-2-sulfonyl)-pyrrolidin-3-yldisulfanyl]-1-(naphthalene-2-sulfonyl)-pyrrolidin-2-yl]-methylamine. The solution was stirred at room temperature overnight, evaporated and the residue was purified on silica gel with a gradient of EtOAc/hexane 2:1 to 4:1 yielding 248 mg (82%) N-[(2S,4R)-4-[(5S,3R)-5-[(4-methoxycarbonyl-benzoylamino)-methyl]-1-(naphthalene-1-sulfonyl)-pyrrolidin-3-yldisulfanyl]-1-(naphthalene-1-sulfonyl)-pyrrolidin-2-ylmethyl]-terephthalamic acid methyl ester as white foam, which was directly subjected to the next reaction.

238 mg (0.25 mmol) of N-[(2S,4R)-4-[(5S,3R)-5-[(4-methoxycarbonyl-benzoylamino)-methyl]-1-(naphthalene-1-sulfonyl)-pyrrolidin-3-yldisulfanyl]-1-(naphthalene-1-sulfonyl)-pyrrolidin-2-ylmethyl]-terephthalamic acid methyl ester were suspended in 7 ml 2,2,2-trifluoro ethanol and 38 µl $H_2O$ and cooled to 0° C. 87 µl (0.3 mmol) tri-n-butylphosphine were added. The mixture was diluted with 1 ml $CH_2Cl_2$ after 1 h at 0° C., and stirring was continued for another 1 h. Evaporation under vacuum and purification on silica gel with EtOAc/hexane 1:1 gave 198 mg (83%) (2S,4R)-N-[4-Mercapto-1-(naphthalene-2-sulfonyl)-pyrrolidin-2-ylmethyl]-terephthalamic acid methyl ester as white solid, MS: 485 ($MH^+$).

In a similar manner, but replacing mono-methylterephthalate with cyclohexane carbonic acid, BOC-glycine, BOC-L-tyrosine, BOC-L-leucine and 4-(2,4-dioxo-1,4-dihydro-2H-quinazolin-3-yl)-butyric acid [Puhl et al. PCT Int. Appl. WO 9856770] and successive cleavage of the disulfide bond (analogously to the example described above) the following compounds were prepared:

(2S,4R)-cyclohexanecarboxylic acid [4-mercapto-1-(naphthalene-2-sulfonyl)-pyrrolidin-2-ylmethyl]-amide as white foam, MS: 433 ($MH^+$);

(2S,4R)-[[[4-mercapto-1-(naphthalene-2-sulfonyl)-pyrrolidin-2-ylmethyl]-carbamoyl]-methyl]-carbamic acid tert-butyl ester as white foam, MS: 480 ($MH^+$);

(S)-[2-(4-hydroxy-phenyl)-1-[[(2S,4R)-4-mercapto-1-(naphthalene-2-sulfonyl)-pyrrolidin-2-ylmethyl]-carbamoyl]-ethyl]-carbamic acid tert-butyl ester as white foam, MS: 586 ($MH^+$);

(S)-[1-[[(2S,4R)-4-mercapto-1-(naphthalene-2-sulfonyl)-pyrrolidin-2-ylmethyl]-carbamoyl]-3-methyl-butyl]-carbamic acid tert-butyl ester as beige foam, MS: 536 ($MH^+$);

(2S,4R)-4-(2,4-dioxo-1,4-dihydro-2H-quinazolin-3-yl)-N-[4-mercapto-1-(naphthalene-2-sulfonyl)-pyrrolidin-2-ylmethyl]-butyramide as white crystalline, MS: 553 ($MH^+$).

A degassed solution of 102 mg (0.21 mmol) (2S,4R)-N-[4-mercapto-1-(naphthalene-2-sulfonyl)-pyrrolidin-2-ylmethyl]-terephthalamic acid methyl ester in 12.6 ml THF was treated with 12.6 ml 0.1 M aqueous LiOH (1.26 mmol, 6 eq) at 0° C. and was stirred at room temperature for 1.5 h. 1 M $KHSO_4$ solution was added (pH 2), the layers were separated and the inorganic one was extracted with EtOAc. The combined organic ones were washed with water and brine, dried over $Na_2SO_4$ and evaporated, yielding (2S,4R)-N-[4-mercapto-1-(naphthalene-2-sulfonyl)-pyrrolidin-2-ylmethyl]-terephthalamic acid as white foam, MS: 471 ($MH^+$).

Reaction with Sulfonyl- or acid-chlorides

To 100 mg (0.16 mmol) C-[(2S,4R)-4-[(3R,5S)-5-aminomethyl-1-(naphthalene-2-sulfonyl)-pyrrolidin-3-yldisulfanyl]1-(naphthalene-2-sulfonyl)-pyrrolidin-2-yl]-methylamine in 8 ml $CH_2Cl_2$ were added 58 mg (0.47 mmol, 2.9 eq) DMAP and 80 mg (0.47 mmol, 2.9 eq) toluene sulfonylchloride. The solution was stirred at room temperature for 2 h and was evaporated. The crude oil was purified on silica gel with $CH_2Cl_2$: EtOAc 9:1 yielding 129 mg (87%) 4-methyl-N-[(2S,4R)-4-[(3R,5S)-5-[(4-methyl-benzenesulfonylamino)-methyl]-1-(naphthalene-2-sulfonyl)-pyrrolidin-3-yldisulfanyl]-1-(naphthalene-2-sulfonyl)-pyrrolidin-2-ylmethyl]-benzenesulfonamide as white crystals.

Cleavage of the disulfide bond analogously to the example described above yielded 120 mg (94%) (2S,4R)-N-[4-mercapto-1-(naphthalene-2-sulfonyl)-pyrrolidin-2-ylmethyl]-4-methyl-benzenesulfonamide as white crystalline, mp 175° C., MS: 477 ($MH^+$).

In a similar manner, but replacing toluene sulfonylchloride with 2-naphthalene sulfonylchloride, methyl sulfonylchloride, acetyl chloride, benzoyl chloride and successive cleavage of the disulfide bond (analogously to example described above) the following compounds were prepared:

Naphthalene-2-sulfonic acid (2S,4R)-[4-mercapto-1-(naphthalene-2-sulfonyl)-pyrrolidin-2-ylmethyl]-amide as white crystalline, mp 156° C., MS: 513 ($MH^+$);

(2S,4R)-N-[4-mercapto-1-(naphthalene-2-sulfonyl)-pyrrolidin-2-ylmethyl]-methanesulfonamide as beige crystalline, mp 136° C., MS: 401 ($MH^+$);

(2S,4R)-N-[4-mercapto-1-(naphthalene-2-sulfonyl)-pyrrolidin-2-ylmethyl]-acetamide as white crystalline, mp 145° C., MS: 365 ($MH^+$);

(2S,4R)-N-[4-mercapto-1-(naphthalene-2-sulfonyl)-pyrrolidin-2-ylmethyl]-benzamide as white crystalline, MS: 427 ($MH^+$).

In analogy Z-L-hydroxyproline benzylester hydrochloride gave (2S,4R)-4-mercapto-2-[(naphthalene-2-sulfonylamino)-methyl]-pyrrolidine-1-carboxylic acid benzyl ester as white solid, MS: 457 ($MH^+$);

Example 7

Heteroaromates (The heteroaromatic compounds were prepared according to Cottrell, Ian F.; Hands, David; Houghton, Peter G.; Humphrey, Guy R., J. Heterocyclic Chem., 28, 301–304 (1991))

To a suspension of 281 mg (2.0 mmol, 4 eq.) potassium carbonate in 2 ml DMSO were added 300 mg (0.51 mmol) (2S,4R)-2-azidomethyl-1-(naphthalene-2-sulfonyl)-4-tritylsulfanyl-pyrrolidine and 72 µl (0.7 mmol, 1.38 eq) acetyl acetone. The reaction mixture was stirred at 40° C. for 3 d, diluted with water and extracted with $Et_2O$, the layers were separated and the inorganic one was extracted with EtOAc, the combined organic layers were washed with brine, dried over $Na_2SO_4$ and evaporated. The residue was purified by column chromatography on silica gel with EtOAc/hexane 1:1 yielding 249 mg (73%) (2S,4R)-1-{5-methyl-1-[1-(naphthalene-2-sulfonyl)-4-tritylsulfanyl-pyrrolidin-2-ylmethyl]-1H-[1,2,3]triazol-4-yl}-ethanone as white foam, MS: 673 ($MH^+$). 150 mg (0.2 mmol) (2S,4R)-1-{5-methyl-1-[1-(naphthalene-2-sulfonyl)-4-tritylsulfanyl-pyrrolidin-2-ylmethyl]-1H-[1,2,3]triazol-4-yl}-ethanone were dissolved in 6.5 ml acetonitrile and 3 ml TFA and were treated with 0.5 ml triethylsilane at 40° C. for 4 h. The reaction mixture was added to a aqueous saturated $NaHCO_3$ solution carefully, extracted, and the organic layer was washed with water and brine, dried over Na$_2$SO$_4$ and evaporated. Purification by column chromatography on silica gel with EtOAc/hexane 1:1 gave 63 mg (66%) (2S,4R)-1-[1-[4-mercapto-1-(naphthalene-2-sulfonyl)-pyrrolidin-2-ylmethyl]-5-methyl-1H-[1,2,3]triazol-4-yl]-ethanone as white solid, mp 145° C., MS: 431 (MH$^+$).

In a similar manner the following compounds were prepared:

From (2S,4R)-2-azidomethyl-4-(4-methoxy-benzylsulfanyl)-1-(naphthalene-2-sulfonyl)-pyrrolidine b) and ethyl acetoacetate (2S,4R)-1-[4-(4-methoxy-benzylsulfanyl)-1-(naphthalene-2-sulfonyl)-pyrrolidin-2-ylmethyl]-5-methyl-1H-[1,2,3]triazole-4-carboxylic acid ethyl ester as white solid, mp 121° C., MS: 581 (MH$^+$);

c) and cyano acetamide (2S,4R)-5-amino-1-[4-(4-methoxy-benzylsulfanyl)-1-(naphthalene-2-sulfonyl)-pyrrolidin-2-ylmethyl]-1H-[1,2,3]triazole-4-carboxylic acid amide as off-white solid, mp 190° C., MS: 553 (MH$^+$);

From (2S,4R)-2-azidomethyl-1-methanesulfonyl-4-(4-methoxy-benzylsulfanyl)-pyrrolidine d) and acetyl acetone (2S,4R)-1{1-[1-methanesulfonyl-4-(4-methoxy-benzylsulfanyl)-pyrrolidin-2-ylmethyl]-5-methyl-1H-[1,2,3]triazol-4-yl}-ethanone as white foam, MS: 439 (MH$^+$);

e) and ethyl acetoacetate (2S,4R)-1-[1-methanesulfonyl-4-(4-methoxy-benzylsulfanyl)-pyrrolidin-2-ylmethyl]-5-methyl-1H-[1,2,3]triazole-4-carboxylic acid ethyl ester as white foam, MS: 469 (MH$^+$);

f) and phenyl acetone (2S,4R)-1-[1-methanesulfonyl-4-(4-methoxy-benzylsulfanyl)-pyrrolidin-2-ylmethyl]-5-methyl-4-phenyl-1H-[1,2,3]triazole as white foam, MS: 473 (MH$^+$).

g) and cyano acetamide (2S,4R)-5-amino-1-[1-methanesulfonyl-4-(4-methoxy-benzylsulfanyl)-pyrrolidin-2-ylmethyl]-1H-[1,2,3]triazole-4-carboxylic acid amide as white foam, MS: 441 (MH$^+$);

h) and benzyl cyanide (2S,4R)-3-[1-methanesulfonyl-4-(4-methoxy-benzylsulfanyl)-pyrrolidin-2-ylmethyl]-5-phenyl-3H-[1,2,3]triazol-4-ylamine as white foam, MS: 473 (MH$^+$);

From (2S,4R)-2-(2-azido-ethyl)-1-methanesulfonyl-4-tritylsulfanyl-pyrrolidine i) and acetyl acetone (2S,4R)-1-[1-[2-(1-methanesulfonyl-4-tritylsulfanyl-pyrrolidin-2-yl)-ethyl]-5-methyl-1H-[1,2,3]triazol-4-yl]-ethanone as white foam, MS: 575 (MH$^+$);

j) and ethyl acetoacetate (2S,4R)-1-[2-(1-methanesulfonyl-4-tritylsulfanyl-pyrrolidin-2-yl)-ethyl]-5-methyl-1H-[1,2,3]triazole-4-carboxylic acid ethyl ester as white foam, MS: 605 (MH$^+$);

k) and phenyl acetone (2S,4R)-1-[2-(1-methanesulfonyl-4-tritylsulfanyl-pyrrolidin-2-yl)-ethyl]-5-methyl-4-phenyl-1H-[1,2,3]triazole as white foam, MS: 609 (MH$^+$);

Cleavage of the protecting group analogously (for Trityl: see example a) above, for methoxy-benzylsulfanyl: Method 2) to yield:

a) (2S,4R)-1-[4-mercapto-1-(naphthalene-2-sulfonyl)-pyrrolidin-2-ylmethyl]-5-methyl-1H-[1,2,3]triazole-4-carboxylic acid ethyl ester as white solid, mp 95° C., MS: 459 (M–H$^+$);

b) (3R,5S)-5-(5-methyl-4-phenyl-[1,2,3]triazol-1-ylmethyl)-1-(naphthalene-2-sulfonyl)-pyrrolidine-3-thiol as light yellow solid, mp 146° C., MS: 465 (MH$^+$);

c) (3R,5S)-5-(5-amino-4-phenyl-[1,2,3]triazol-1-ylmethyl)-1-(naphthalene-2-sulfonyl)-pyrrolidine-3-thiol as white solid, mp 70° C., MS: 466 (MH$^+$);

d) (2S,4R)-1-(4-mercapto-1-methanesulfonyl-pyrrolidin-2-ylmethyl)-5-methyl-1H-[1,2,3]triazole-4-carboxylic acid ethyl ester as white solid, mp 123° C., MS:469(MH$^+$);

e) (3R,5S)-1-methanesulfonyl-5-(5-methyl-4-phenyl-[1,2,3]triazol-1-ylmethyl)-pyrrolidine-3-thiol as white solid, mp 150° C., MS:473(MH$^+$);

f) (2S,4R)-5-amino-1-(4-mercapto-1-methanesulfonyl-pyrrolidin-2-ylmethyl)-1H-[1,2,3]triazole-4-carboxylic acid amide as white solid, mp 189° C., MS: 321(MH$^+$);

g) (3R,5S)-5-(5-amino-4-phenyl-[1,2,3]triazol-1-ylmethyl)-1-methanesulfonyl-pyrrolidine-3-thiol as white foam, MS: 354(MH$^+$);

h) (2S,4R)-1-[1-[2-(4-mercapto-1-methanesulfonyl-pyrrolidin-2-yl)-ethyl]-5-methyl-1H-[1,2,3]triazol-4-yl]-ethanone as colorless oil, MS: 317 (M–CH$_3$$^+$);

i) (2S,4R)-1-[2-(4-mercapto-1-methanesulfonyl-pyrrolidin-2-yl)-ethyl]-5-methyl-1H-[1,2,3]triazole-4-carboxylic acid ethyl ester as colorless oil, MS: 363 (MH$^+$);

j) (3R,5S)-1-methanesulfonyl-5-[2-(5-methyl-4-phenyl-[1,2,3]triazol-1-yl)-ethyl]-pyrrolidine-3-thiol as colorless oil, MS: 366 (MH$^+$);

Saponification of the ethyl ester analogously to (see above: General method for hydrolysis of an ester) yielded:

(2S,4R)-1-[4-mercapto-1-(naphthalene-2-sulfonyl)-pyrrolidin-2-ylmethyl]-5-methyl-1H-[1,2,3]triazole-4-carboxylic acid as white solid, mp 218° C., MS: 431(M–H$^-$).

In a similar manner, but without isolation of intermediates the following compounds were prepared:

(2S,4R)-2-azidomethyl-4-(4-methoxy-benzylsulfanyl)-1-(naphthalene-2-sulfonyl)-pyrrolidine and methyl benzyl ketone and removal of the PMB protecting group (Method 2) (2S,4R)-1-[4-mercapto-1-(naphthalene-2-sulfonyl)-pyrrolidin-2-ylmethyl]-5-methyl-1H-[1,2,3]triazole-4-carboxylic acid as white solid, mp 218° C., MS: 431 (M–H$^-$);

From (2S,4R)-2-azidomethyl-4-(4-methoxy-benzylsulfanyl)-1-(naphthalene-2-sulfonyl)-pyrrolidine and benzyl cyanide and and removal of the PMB protecting group (Method 2) (2S,4R)-5-amino-1-[4-mercapto-1-(naphthalene-2-sulfonyl)-pyrrolidin-2-ylmethyl]-1H-[1,2,3]triazole-4-carboxylic acid amide as white solid, mp 130° C., MS: 433 (MH$^+$);

From (2R,4R)-2-(2-azido-ethyl)-1-(naphthalene-2-sulfonyl)-4-tritylsulfanyl-pyrrolidine and phenyl acetone and removal of the protecting group (3R,5R)-5-[2-(5-methyl-4-phenyl-[1,2,3]triazol-1-yl)-ethyl]-1-(naphthalene-2-sulfonyl)-pyrrolidine-3-thiol as light yellow foam, MS: 479 (MH$^+$).

Example 8

N-Pyrrolidine-optimization, Heteroaromates

In analogy to above Example 7: (2S,4R)-2-azidomethyl-4-tritylsulfanyl-pyrrolidine-1-carboxylic acid tert-butyl ester and phenyl acetone gave (2S,4R)-2-(5-methyl-4-phenyl-[1,2,3]triazol-1-ylmethyl)-4-tritylsulfanyl-pyrrolidine-1-carboxylic acid tert-butyl ester as yellow crystals, MS: 616 (MH$^+$).

(2S,4R)-2-(5-methyl-4-phenyl-[1,2,3]triazol-1-ylmethyl)-4-tritylsulfanyl-pyrrolidine-1-carboxylic acid tert-butyl ester gave by treatment with TFA in methylene chloride (following the general method for a selective BOC-deprotection) (2S,4R)-5-methyl-4-phenyl-1-(4-tritylsulfanyl-pyrrolidin-2-ylmethyl)-1H-[1,2,3]triazole as yellow foam, MS: 517 (MH$^+$);

(2S,4R)-5-methyl-4-phenyl-1 (4-tritylsulfanyl-pyrrolidin-2-ylmethyl)-1H-[1,2,3]triazole and benzyl chloroformate, N-ethyldiisopropylamine in CH$_2$Cl$_2$ (see carbamate synthesis, Method A) followed by the removal of the trityl-protecting group (see Method 3) gave (2S,4R)-4-mercapto-2-(5-methyl-4-phenyl-[1,2,3]triazol-1-ylmethyl)-pyrrolidine-1-carboxylic acid benzyl ester as white foam, MS: 409(MH$^+$).

In a similar manner but replacing benzyl chloroformate with isopropyl chloroformate, phenyl chloroformate, chloroformic acid 2-naphtyl ester, 1,4-benzodioxan-5-yl chloroformate [Eitel, A. & Hammann, I. S. African, ZA 6800512 680627] and butyl chloroformate the following compounds were prepared:

(2S,4R)-4-mercapto-2-(5-methyl-4-phenyl-[1,2,3]triazol-1-ylmethyl)-pyrrolidine-1-carboxylic acid isopropyl ester as colorless oil, MS: 361 (MH$^+$);

(2S,4R)-4-mercapto-2-(5-methyl-4-phenyl-(1,2,3)triazol-1-ylmethyl)-pyrrolidine-1-carboxylic acid phenyl ester as white foam, MS: 395 (MH$^+$);

(2S,4R)-4-mercapto-2-(5-methyl-4-phenyl-[1,2,3]triazol-1-ylmethyl)-pyrrolidine-1-carboxylic acid naphthalen-2-yl ester as colorless oil, MS: 445 (MH$^+$);

(2S,4R)-4-mercapto-2-(5-methyl-4-phenyl-[1,2,3]triazol-1-ylmethyl)-pyrrolidine-1-carboxylic acid 2,3-dihydro-benzo[1,4]dioxin-5-yl ester as colorless oil, MS: 453(MH$^+$);

(2S,4R)-4-mercapto-2-(5-methyl-4-phenyl-[1,2,3]triazol-1-ylmethyl)-pyrrolidine-1-carboxylic acid butyl ester as colorless oil, MS: 375(MH$^+$).

Example 9
Ether, Phenolethers 0.37 ml (2.25 mmol) DEAD was added at −15° C. to 590 mg (2.25 mmol) triphenylphosphine in 3 ml THF. Then a solution of 497 mg (1.5 mmol) (2S,4R)-[1-methanesulfonyl-4-(4-methoxy-benzylsulfanyl)-pyrrolidin-2-yl]-methanol and 146 mg (1.5 mmol) phenol in 2 ml THF was added. The reaction was stirred at 0° C. over night, heated to reflux and evaporated under reduced pressure. Flash silica gel column (hexane/EtOAc 4:1) gave 240 mg (39%) of (2S,4R)-1-methanesulfonyl-4-(4-methoxy-benzylsulfanyl)-2-phenoxymethyl-pyrrolidine, mp 92–94° C., MS: 408 (MH$^+$).

(Method 2): A solution of 102 mg (0.25 mmol) (2S,4R)-1-methanesulfonyl-4-(4-methoxy-benzylsulfanyl)-2-phenoxymethyl-pyrrolidine and 0.4 ml (2.5 mmol) triethylsilane was heated for 1 min at 80° C., cooled to room temperature and evaporated. Crystallization from Et$_2$O/pentane gave 39 mg (54%) of (3R,5S)-1-methanesulfonyl-5-phenoxymethyl-pyrrolidine-3-thiol, mp 78–79° C., MS: 288 (MH$^+$).

In analogy: (2R,4R)-2-(1-methanesulfonyl-4-trityIsulfanyl-pyrrolidin-2-yl)-ethanol gave after TFA/triethylsilane trityl deprotection (Method 3) (3R,5R)-1-methanesulfonyl-5-(2-phenoxy-ethyl)-pyrrolidine-3-thiol, mp 82.5–83.5° C., MS: 302 (MH$^+$).

Example 10
Ether, O-carbamate

A solution of 497 mg (1.5 mmol) (2S,4R)-[1-methanesulfonyl-4-(4-methoxy-benzylsulfanyl)-pyrrolidin-2-yl]-methanol in 9 ml toluene was treated with 0.18 ml (1.65 mmol) phenylisocyanate and 0.18 ml (1.65 mmol) 4-methylmorpholine. The reaction was stirred over night at room temperature and extracted with aqueous 10% KHSO$_4$/EtOAc (3×). The organic phase was washed with aqueous saturated NaHCO$_3$ dried over Na$_2$SO$_4$ and evaporated. Flash column chromatography on silica gel with hexane/EtOAc (4:1 to 2:1) gave 426 mg (63%) of phenyl-carbamic acid (2S,4R)-1-methanesulfonyl-4-(4-methoxy-benyzlsulfanyl)-pyrrolidin-2-ylmethyl ester, mp 141.5–142.5° C., MS: 451 (MH$^+$).

TFA/triethylsilane deprotection (Method 2, 8 min refluxed) gave phenyl-carbamic acid (2S,4R)-4-mercapto-1-methanesulfonyl-pyrrolidin-2-ylmethyl ester in 55% yield, mp 147.5–148.5° C., MS: 331 (MH$^+$).

In analogy: (2R,4R)-2-(1-methanesulfonyl-4-tritylsulfanyl-pyrrolidin-2-yl)-ethanol gave phenyl-carbamic acid (2R,4R)-2-[4-mercapto-1-(naphthalene-2-sulfonyl)-pyrrolidin-2-yl]-ethyl ester, MS: 456 (M).

A solution of 150 mg (0.33 mmol) phenyl-carbamic acid (2S,4R)-1-methane-sulfonyl-4-(4-methoxy-benzylsulfanyl)-pyrrolidin-2-ylmethyl ester in 1.3 ml DMF was treated at 0° C. with 23.2 mg (0.53 mmol) 55% NaH and 30 min later with 0.2 ml (1.33 mmol) tert-butyl bromoacetate. Over night it was warmed up to room temperature, then extracted with aqueous saturated NH$_4$Cl/EtOAc (3×). The organic phases were washed with aqueous 10% NaCl, dried (Na$_2$SO$_4$) and evaporated. Flash chromatography on silica gel (EtOAc/hexane 1/2) gave 179 mg (95%) of (2S,4R)-{[1-methanesulfonyl-4-(4-methoxy-benzylsulfanyl)-pyrrolidin-2-ylmethoxycarbonyl]-phenyl-amino}-acetic acid tert-butyl ester, MS: 565 (MH$^+$).

TFA/triethylsilane-deprotection (Method 2, 1 min refluxed) gave (2S,4R)-[(4-mercapto-1-methanesulfonyl-pyrrolidin-2-ylmethoxycarbonyl)-phenyl-amino]-acetic acid was received in 50% yield, MS: 389 (MH$^+$).

In analogy: (2R,4R)-2-(1-methanesulfonyl-4-tritylsulfanyl-pyrrolidin-2-yl)-ethanol gave via phenyl-carbamic acid (2R,4R)-2-[1-(naphthalene-2-sulfonyl)-4-tritylsulfanyl-pyrrolidin-2-yl]-ethyl ester with methyl bromoacetate (2R,4R)-({2-[4-mercapto-1-(naphthalene-2-sulfonyl)-pyrrolidin-2-yl]-ethoxycarbonyl}-phenyl-amino)-acetic acid methyl ester, MS: 529 (MH$^+$).

Example 11
Ether (Table 1 and Table 2)

Method A: 9.07 g (20 mmol) of (2S,4R)-(1-methanesulfonyl-4-tritylsulfanyl-pyrrolidin-2-yl)-methanol and 9.5 ml (80 mmol) of benzylbromide were dissolved in 660 ml DMF, cooled to 0° C. and treated with 1.4 g (32 mmol) of 55% NaH over 15 min in 4 portions. The reaction was warmed up over night and treated with 4.75 ml (40 mmol) benzylbromide/700 mg (16 mmol) 55% NaH and 6 h later again with the same amount of benzylbromide/NaH. After further 16 h at room temperature the reaction was quenched with saturated NH$_4$Cl solution/EtOAc (3×). The organic phase was washed with aqueous 10% NaCl soution, dried over Na$_2$SO$_4$ and evaporated to give 25 g crude product. Flash-chromatography on silica gel (Hexane/EtOAc 4:1 to 1:4) gave 6.43 g (59%) of (2S,4R)-2-benzyloxymethyl-1-methanesulfonyl-4-tritylsulfanyl-pyrrolidine, MS: 544 (MH+). 6.4 g (11.77 mmol) (2S,4R)-2-benzyloxymethyl-1-methanesulfonyl-4-tritylsulfanyl-pyrrolidine were dissolved in 170 ml TFA and treated at 0° C. with 18.75 ml (117.7 mmol) of triethylsilane. After 18 h at 0° C., the mixture was evaporated and purified by flash-chromatography on silica gel (Hexane/EtOAc 4:1 to 1:4) to give 2.66 g (72%) of (3R,5S)-5-benzyloxymethyl-1-methanesulfonyl-pyrrolidine-3-thiol, MS: 302 (MH+).

In analogy: (2S,4R)-2-hydroxymethyl-4-tritylsulfanyl-pyrrolidine-1-carboxylic acid butyl ester with benzyl bromide gave (2S,4R)-2-benzyloxymethyl-4-mercapto-pyrrolidine-1-carboxylic acid butyl ester, MS: 324 (MH+).

(2S,4R)-(1-methanesulfonyl-4-tritylsulfanyl-pyrrolidin-2-yl)-methanol with 3-bromo-1-phenyl-1-propene, followed by hydrogenation (17 h) and TFA/triethylsilane deprotection (Method 3) gave (3R,5S)-1-methanesulfonyl-5-(3-phenyl-propoxymethyl)-pyrrolidine-3-thiol, MS: 329 (M).

Method B: A solution of 0.41 g (0.91 mmol) in 20 ml (bromomethyl)cyclohexane was mixed with 20 ml aqueous 50% NaOH and a catalytic amount of tetrabutyl-ammonium hydrogen sulfate and stirred vigorously over night. The organic phase was separated, and evaporated on the Kugelrohr. Flash-chromatography on silica gel (hexane/EtOAc 95:5) gave 0.3 g (60%) of (2S,4R)-2-cyclohexylmethoxymethyl-1-methanesulfonyl-4-tritylsulfanyl-pyrrolidine, MS: 550 (MH+).

In analogy to Method 3: (2S,4R)-2-cyclohexylmethoxymethyl-1-methanesulfonyl-4-tritylsulfanyl-pyrrolidine gave (3R,5S)-5-cyclohexylmethoxymethyl-1-methanesulfonyl-pyrrolidine-3-thiol, mp 68–69° C., MS: 308 (MH+).

Following Method A: (2S,4R)-[4-(4-methoxy-benzylsulfanyl)-1-(naphthalene-2-sulfonyl)-pyrrolidin-2-yl]-methanol and iodomethane gave after PMB deprotection (Method 1) (3R,5S)-5-methoxymethyl-1-(naphthalene-2-sulfonyl)-pyrrolidine-3-thiol as colorless solid, 68–69° C., MS: 338 (MH+).

According to an analogous method the following compounds were prepared via reacton of (2S,4R)-(1-methanesulfonyl-4-tritylsulfanyl-pyrrolidin-2-yl)-methanol and the 2. educt. mentioned in the following table 1. With chlorides one equivalent of NaI was added:

TABLE 1

| | Name | 2. Educt | Method | MS | COLOR | MP | PHYSICAL FORM |
|---|---|---|---|---|---|---|---|
| 1 | (3R,5S)-5-Benzyloxymethyl-1-methanesulfonyl-pyrrolidine-3-thiol | BENZYL BROMIDE | A | 302 | M+H+ white | | waxy solid |
| 2 | (2S,4R)-3-(4-Mercapto-1-methanesulfonyl-pyrrolidin-2-ylmethoxymethyl)-benzoic acid methyl ester | 3-CARBOMETHOXY-BENZYL BROMIDE | A | 356 | M+H+ white | | waxy solid |
| 3 | (3R,5S)-1-Methanesulfonyl-5-(pyridin-2-ylmethoxy-methyl)-pyrrolidine-3-thiol trifluoro-acetate (1:1) | 2-PICOLYL CHLORIDE HYDROCHLORID | A | 302 | M+H+ color-less | | oil |
| 4 | (3R,5S)-1-Methanesulfonyl-5-(pyridin-4-ylmethoxymethyl)-pyrrolidine-3-thiol trifluoro-acetate (1:1) | 4-PICOLYL CHLORIDE HYDROCHLORID | A | 302 | M+H+ yellow | | oil |
| 5 | (3R,5S)-1-Methanesulfonyl-5-prop-2-ynyloxymethyl-pyrrolidine-3-thiol | PROPARGYL BROMIDE | A | 248 | M−H− brown | | oil |
| 6 | (3R,5S)-1-Methanesulfonyl-5-(pyridin-3-ylmethoxy-methyl)-pyrrolidine-3-thiol) trifluoro-acetate (1:1) | 3-PICOLYL CHLORIDE HYDROCHLORID | A | 302 | M+H+ colorless | | oil |
| 7 | (3R,5S)-1-Methanesulfonyl-5-(naphthalen-2-ylmethoxymethyl)-pyrrolidine-3-thiol | 2-(BROMOMETHYL)-NAPHTHALENE | A | 352 | M+H+ white | 104–106° C. | powder |
| 8 | (3R,5S)-1-Methanesulfonyl-5-(naphthalen-1-ylmethoxymethyl)-pyrrolidine-3-thiol | 1-(BROMOMETHYL)-NAPHTHALENE | A | 352 | M+H+ white | 93–95° C. | crystalline |
| 9 | (3R,5S)-1-Methanesulfonyl-5-(3-methoxy-benzyloxymethyl)-pyrrolidine-3-thiol | 3-METHOXYBENZYL BROMIDE | A | 332 | M+H+ | | |
| 10 | (3R,5S)-5-(4-tert-Butyl-benzyloxymethyl)-1-methanesulfonyl-pyrrolidine-3-thiol | 4-TERT-BUTYLBENZYL BROMIDE | A | 358 | M+H+ | | |
| 11 | (3R,5S)-1-Methanesulfonyl-5-pentafluorophenylmethoxymethyl-pyrrolidine-3-thiol | PENTAFLUOROBENZYL BROMIDE | A | 392 | M+H+ | | |
| 12 | (3R,5S)-5-(3-Bromo-benzyloxymethyl)-1-methanesulfonyl-pyrrolidine-3-thiol | 3-BROMO BENZYL BROMIDE | A | 380 | M+H+, 1Br | | |
| 13 | (2S,4R)-3-(4-Mercapto-1-methanesulfonyl-pyrrolidin-2-ylmethoxymethyl)-benzonitrile | 3-CYANO BENZYL BROMIDE | A | 327 | M+H+ | | |
| 14 | (3R,5S)-1-Methanesulfonyl-5-(4-methyl-benzyloxymethyl)-pyrrolidine-3-thiol | 4-METHYL BENZYL BROMIDE | A | 316 | M+H+ | | |
| 15 | (3R,5S)-1-Methanesulfonyl-5-(2-methyl-benzyloxymethyl)-pyrrolidine-3-thiol | 2-METHYL BENZYL BROMIDE | A | 316 | M+H+ | | |
| 16 | (3R,5S)-1-Methanesulfonyl-5-(3-methyl-benzyloxymethyl)-pyrrolidine-3-thiol | 3-METHYL BENZYL BROMIDE | A | 316 | M+H+ | | |
| 17 | (3R,5S)-5-(2-Fluoro-benzyloxymethyl)-1-methanesulfonyl-pyrrolidine-3-thiol | 2-FLUORO BENZYL BROMIDE | A | 320 | M+H+ | | |
| 18 | (3R,5S)-5-(3-Fluoro-benzyloxymethyl)-1-methanesulfonyl-pyrrolidine-3-thiol | 3-FLUORO BENZYL BROMIDE | A | 320 | M+H+ | | |

TABLE 1-continued

| Name | 2. Educt | Method | MS | COLOR | MP | PHYSICAL FORM |
|---|---|---|---|---|---|---|
| 19 Mixture of (3R,5S)-1-methanesulfonyl-5-[(R)- and -[(S)-1-phenyl-ethoxymethyl)-pyrrolidi | (1-BROMOETHYL) BENZENE | A | 338 M+Na+ | | | |
| 20 (3R,5S)-5-(2-Chloro-benzyloxymethyl)-1-methanesulfonyl-pyrrolidine-3-thiol | 3-CHLOROO BENZYL BROMIDE | A | 336 M+H+ | | | |
| 21 (3R,5S)-5-(2,4-Difluoro-benzyloxymethyl)-1-methanesulfonyl-pyrrolidine-3-thiol | 2,4-DIFLUORO BENZYL BROMIDE | A | 338 M+H+ | | | |
| 22 (3R,5S)-5-(3-Chloro-benzyloxymethyl)-1-methanesulfonyl-pyrrolidine-3-thiol | 3-CHLORO BENZYL BROMIDE | A | 336 M+H+ | | | |
| 23 (3R,5S)-5-(3,5-Dimethyl-benzyloxymethyl)-1-methanesulfonyl-pyrrolidine-3-thiol | 3,5-DIMETHYLBENZYL BROMIDE | A | 330 M+H+ | | | |
| 24 (3R,5S)-5-(4-Fluoro-benzyloxymethyl)-1-methanesulfonyl-pyrrolidine-3-thiol | 4-FLUORO BENZYL BROMIDE | A | 320 M+H+ | | | |
| 25 (3R,5S)-1-Methanesulfonyl-5-(2,3,6-trifluoro-benzyloxymethyl)-pyrrolidine-3-thiol | 2,3,5-TRIFLUORO BENZYL BROMIDE | A | 356 M+H+ | | | |
| 26 (3R,5S)-5-(3,5-Difluoro-benzyloxymethyl)-1-methanesulfonyl-pyrrolidine-3-thiol | 3,5-DIFLUORO BENZYL BROMIDE | A | 338 M+H+ | | | |
| 27 (3R,5S)-5-(Biphenyl-4-ylmethoxymethyl)-1-methanesulfonyl-pyrrolidine-3-thiol | 4-BIPHENYLMETHYL CHLORIDE | A | 400 M+Na+ | | | |
| 28 (3R,5S)-1-Methanesulfonyl-5-(3-phenoxy-benzyloxymethyl)-pyrrolidine-3-thiol | 3-PHENOXYBENZYL CHLORIDE | A | 416 M+Na+ | | | |
| 29 (3R,5S)-5-(2,5-Difluoro-benzyloxymethyl)-1-methanesulfonyl-pyrrolidine-3-thiol | 2,5-DIFLUORO BENZYL BROMIDE | A | 338 M+H+ | | | |
| 30 (3R,5S)-5-(3,4-Difluoro-benzyloxymethyl)-1-methanesulfonyl-pyrrolidine-3-thiol | 3,4-DIFLUORO BENZYL BROMIDE | A | 338 M+H+ | | | |
| 31 (3R,5S)-5-(Benzo[1,3]dioxol-5-ylmethoxymethyl)-1-methanesulfonyl-pyrrolidine-3-thiol | 3,4-METHYLENE-DIOXYBENZYL CHLORIDE | A | 368 M+Na+ | | | |
| 32 (3R,5S)-1-Methanesulfonyl-5-phenethyloxymethyl-pyrrolidine-3-thiol | 2-PHENYLETHYL BROMIDE | B | 316 M+H+ | brown | | oil |
| 33 (3R,5S)-1-Methanesulfonyl-5-(3-phenyl-propoxymethyl)-pyrrolidine-3-thiol | CINNAMYL BROMIDE | A | 329 M | brown | | oil |
| 34 (3R,5S)-5-(2-Fluoro-3-trifluoromethyl-benzyloxymethyl)-1-methanesulfonyl-pyrrolidine-3-thiol | 2-FLUORO-3-TRIFLUORO-BENZYL BROMIDE | A | 388 M+H+ | | | |
| 35 (3R,5S)-5-(2-Chloro-6-fluoro-benzyloxymethyl)-1-methanesulfonyl-pyrrolidine-3-thiol | 2-CHLORO-6-FLUORO BENZYL BROMIDE | A | 354 M+H+ | | | |
| 36 (3R,5S)-5-(2,3-Difluoro-4-trifluoromethyl-benzyloxymethyl)-1-methanesulfonyl-pyrrolidine-3-thiol | 2,3-DIFLUORO-4-TRIFLUOROMETHYLBENZYL BROMIDE | A | 406 M+H+ | | | |
| 37 (3R,5S)-1-Methanesulfonyl-5-(2-trifluoromethoxy-benzyloxymethyl)-pyrrolidine-3-thiol | 2-(TRIFLUORO-METHOXY)-BENZYL BROMIDE | A | 386 M+H+ | | | |
| 38 (3R,5S)-5-(2-Fluoro-5-trifluoromethyl-benzyloxymethyl)-1-methanesulfonyl-pyrrolidine-3-thiol | 2-FLUORO-5-TRIFLUOROBENZYL BROMIDE | A | 388 M+H+ | | | |
| 39 (3R,5S)-5-(2-Fluoro-4-trifluoromethyl-benzyloxymethyl)-1-methanesulfonyl-pyrrolidine-3-thiol | 2-FLUORO-4-TRIFLUOROBENZYL BROMIDE | A | 388 M+H+ | | | |
| 40 (3R,5S)-5-(2-Fluoro-6-trifluoromethyl-benzyloxymethyl)-1-methanesulfonyl-pyrrolidine-3-thiol | 2-FLUORO-6-TRIFLUOROBENZYL BROMIDE | A | 388 M+H+ | | | |
| 41 (3R,5S)-1-Methanesulfonyl-5-(2,4,5-trifluoro-benzyloxymethyl)-pyrrolidine-3-thiol | 2,4,5-TRIFLUORO BENZYL BROMIDE | A | 356 M+H+ | | | |
| 42 (3R,5S)-5-(2,6-Difluoro-benzyloxymethyl)-1-methanesulfonyl-pyrrolidine-3-thiol | 2,6-DIFLUORO BENZYL BROMIDE | A | 338 M+H+ | | | |
| 43 (3R,5S)-1-Methanesulfonyl-5-(2,3,4-trifluoro-benzyloxymethyl)-pyrrolidine-3-thiol | 2,3,4-TRIFLUORO BENZYL BROMIDE | A | 356 M+H+ | | | |
| 44 (3R,5S)-5-(2,3-Difluoro-benzyloxymethyl)-1-methanesulfonyl-pyrrolidine-3-thiol | 2,3-DIFLUORO BENZYL BROMIDE | A | 338 M+H+ | | | |
| 45 (3R,5S)-1-Methanesulfonyl-5-(2-trifluoromethyl-benzyloxymethyl)-pyrrolidine-3-thiol | 2-TRIFLUOROBENZYL BROMIDE | A | 370 M+H+ | | | |
| 46 (3R,5S)-5-(2-Bromo-benzyloxymethyl)-1-methanesulfonyl-pyrrolidine-3-thiol | 2-BROMO BENZYL BROMIDE | A | 380 M+H+ 1Br | | | |
| 47 (3R,5S)-5-(Biphenyl-2-ylmethoxymethyl)-1-methanesulfonyl-pyrrolidine-3-thiol | 2-PHENYLBENZYL BROMIDE | A | 400 M+Na+ | | | |
| 48 (2S,4R)-2-(4-Mercapto-1-methanesulfonyl-pyrrolidin-2-ylmethoxymethyl)-benzonitrile | 2-CYANO BENZYL BROMIDE | A | 327 M+H+ | | | |

TABLE 1-continued

| Name | 2. Educt | Method | MS | | COLOR | MP | PHYSICAL FORM |
|---|---|---|---|---|---|---|---|
| 49 (3R,5S)-1-Methanesulfonyl-5-(3,4,5-trifluoro-benzyloxymethyl)-pyrrolidine-3-thiol | 3,4,5-TRIFLUORO BENZYL BROMIDE | A | 356 | M+H+ | | | |
| 50 (3R,5S)-1-Methanesulfonyl-5-(2,3,5-trifluoro-benzyloxymethyl)-pyrrolidine-3-thiol | 2,3,5-TRIFLUORO BENZYL BROMIDE | A | 356 | M+H+ | | | |
| 51 (3R,5S)-1-Methanesulfonyl-5-(2,4,6-trifluoro-benzyloxymethyl)-pyrrolidine-3-thiol | 2,4,6-TRIFLUORO BENZYL BROMIDE | A | 356 | M+H+ | | | |
| 52 (3R,5S)-5-Cyclohexylmethoxymethyl-1-methanesulfonyl-pyrrolidine-3-thiol | (BROMOMETHYL) CYCLOHEXANE | B | 308 | M+H+ | white | 68–69° C. | crystalline |
| 53 (3R,5S)-5-(5-Chloro-thiophen-2-ylmethoxymethyl)-1-methanesulfonyl-pyrrolidine-3-thiol | 2-CHLORO-5-(CHLOROMETHYL) THIOPHENE | A | 341.9 | M+H+ | colorless | | oil |
| 54 3R,5S)-1-Methanesulfonyl-5-(5-methyl-isoxazol-3-ylmethoxymethyl)-pyrrolidine-3-thiol | 3-CHLOROMETHYL-5-METHYLISOXAZOLE | A | 307 | M+H+ | white | 74–75° C. | crystalline |
| 55 (3R,5S)-1-Methanesulfonyl-5-(2-methyl-thiazol-4-ylmethoxymethyl)-pyrrolidine-3-thiol trifluoro-acetate (1:1) | 4-CHLOROMETHYL-2-METHYLTHIAZOLE HYDROCHLORIDE | A | 437 | M+H+ | colorless | | oil |

Further compounds were prepared by reaction of (2S,4R)-2-hydroxymethyl-4-tritylsulfanyl-pyrrolidine-1-carboxylic acid butyl ester with the second educt mentioned in table 2:

TABLE 2

| Name | 2. Educt | Method | MS | |
|---|---|---|---|---|
| 1 (2S,4R)-2-Benzyloxymethyl-4-mercapto-pyrrolidine-1-carboxylic acid butyl ester | BENZYL BROMIDE | A | M+H+ | 324 |
| 2 (2S,4R)-2-(3-Chloro-benzyloxymethyl)-4-mercapto-pyrrolidine-1-carboxylic acid butyl ester | 3-CHLORO BENZYL BROMIDE | A | M+H+ | 358 |
| 3 (2S,4R)-2-(3-Cyano-benzyloxymethyl)-4-mercapto-pyrrolidine-1-carboxylic acid butyl ester | 3-CYANO BENZYL BROMIDE | A | M+H+ | 349 |
| 4 (2S,4R)-2-(3-Bromo-benzyloxymethyl)-4-mercapto-pyrrolidine-1-carboxylic acid butyl ester | 3-BROMO BENZYL BROMIDE | A | M+H+, 1Br | 402 |
| 5 (2S,4R)-2-(3-Fluoro-benzyloxymethyl)-4-mercapto-pyrrolidine-1-carboxylic acid butyl ester | 3-FLUORO BENZYL BROMIDE | A | M+H+ | 342 |
| 6 (2S,4R)-2-(2-Fluoro-benzyloxymethyl)-4-mercapto-pyrrolidine-1-carboxylic acid butyl ester | 2-FLUORO BENZYL BROMIDE | A | M+H+ | 342 |
| 7 (2S,4R)-2-(2,4-Difluoro-benzyloxymethyl)-4-mercapto-pyrrolidine-1-carboxylic acid butyl ester | 2,4-DIFLUORO BENZYL BROMIDE | A | M+H+ | 360 |
| 8 (2S,4R)-2-(2-Chloro-benzyloxymethyl)-4-mercapto-pyrrolidine-1-carboxylic acid butyl ester | 2-CHLORO BENZYL BROMIDE | A | M+H+ | 358 |
| 9 (2S,4R)-2-(4-Bromo-2-fluoro-benzyloxymethyl)-4-mercapto-pyrrolidine-1-carboxylic acid butyl ester | 4-BROMO-2-FLUORO BENZYL BROMIDE | A | M+H+, 1Br | 420 |
| 10 (2S,4R)-4-Mercapto-2-(3-methyl-benzyloxymethyl)-pyrrolidine-1-carboxylic acid butyl ester | 3-METHYL BENZYL BROMIDE | A | M+H+ | 338 |
| 11 (2S,4R)-4-Mercapto-2-(2,3,6-trifluoro-benzyloxymethyl)-pyrrolidine-1-carboxylic acid butyl ester | 2,3,6-TRIFLUORO BENZYL BROMIDE | A | M+H+ | 378 |
| 12 (2S,4R)-2-(3,4-Difluoro-benzyloxymethyl)-4-mercapto-pyrrolidine-1-carboxylic acid butyl ester | 3,4-DIFLUORO BENZYL BROMIDE | A | M+H+ | 360 |
| 13 (2S,4R)-2-(4-Fluoro-benzyloxymethyl)-4-mercapto-pyrrolidine-1-carboxylic acid butyl ester | 4-FLUORO BENZYL BROMIDE | A | M+H+ | 342 |
| 14 (2S,4R)-2-(2,5-Difluoro-benzyloxymethyl)-4-mercapto-pyrrolidine-1-carboxylic acid butyl ester | 2,5-DIFLUORO BENZYL BROMIDE | A | M+H+ | 360 |
| 15 (2S,4R)-2-(3-Chloro-2-fluoro-benzyloxymethyl)-4-mercapto-pyrrolidine-1-carboxylic acid butyl ester | 3-CHLORO-2FLUORO BENZYL BROMIDE | A | M+H+ | 376 |

TABLE 2-continued

| Name | 2. Educt | Method | MS | |
|---|---|---|---|---|
| 16 (2S,4R)-2-(2-Cyano-benzyloxymethyl)-4-mercapto-pyrrolidine-1-carboxylic acid butyl ester | 2-CYANO BENZYL BROMIDE | A | M+H+ | 349 |
| 17 (2S,4R)-2-(2-Bromo-benzyloxymethyl)-4-mercapto-pyrrolidine-1-carboxylic acid butyl ester | 2-BROMO BENZYL BROMIDE | A | M+H+, 1Br | 402 |
| 18 (2S,4R)-2-(2,3-Difluoro-benzyloxymethyl)-4-mercapto-pyrrolidine-1-carboxylic acid butyl ester | 2,3-DIFLUORO BENZYL BROMIDE | A | M+H+ | 360 |
| 19 (2S,4R)-2-(2-Fluoro-4-trifluoromethyl-benzyloxymethyl)-4-mercapto-pyrrolidine-1-carboxylic acid butyl ester | 2-FLUORO-4-TRIFLUOROMETHYL BENZYL BROMIDE | A | M+H+ | 410 |
| 20 (2S,4R)-4-Mercapto-2-(2,3,5-trifluoro-benzyloxymethyl)-pyrrolidine-1-carboxylic acid butyl ester | 2,3,5-TRIFLUORO BENZYL BROMIDE | A | M+H+ | 378 |
| 21 (2S,4R)-4-Mercapto-2-(2,3,4-trifluoro-benzyloxymethyl)-pyrrolidine-1-carboxylic acid butyl ester | 2,3,4-TRIFLUORO BENZYL BROMIDE | A | M+H+ | 378 |
| 22 (2S,4R)-4-Mercapto-2-(3,4,5-trifluoro-benzyloxymethyl)-pyrrolidine-1-carboxylic acid butyl ester | 3,4,5-TRIFLUORO BENZYL BROMIDE | A | M+H+ | 378 |

Example 12

Ether, Sugar Replacement

To a solution of (2S,4R)-(4-mercapto-1-methanesulfonyl-pyrrolidin-2-yl)-methanol (0.28 g) in dichloromethane (10 ml) were added pyridine (0.131 g) and acetic anhydride (0.160 g). The reaction mixture was stirred for 4 h at room temperature, treated with ice/water and extracted with EtOAc. The organic phase was washed with a saturated solution of sodium bicarbonate and brine, dried over magnesium sulphate and concentrated. The residue was chromatographed on silica gel using EtOAc/hexane 1:2 as eluent to obtain thioacetic acid (3R,5S)-S-(5-hydroxymethyl-1-methanesulfonyl-pyrrolidin-3-yl) ester (0.080 g) as a viscous oil.

A solution of thioacetic acid (3R,5S)-S-(5-hydroxymethyl-1-methanesulfonyl-pyrrolidin-3-yl) ester (0.070 g) and 1,2,3,4-tetra-O-acetyl-6-deoxy-beta-L-mannopyranose [G. Hodosi and P. Kovàc, Carbohydr. Res., 303, 239–243 (1997)] (0.138 g) in dichloromethane (10.0 ml) was treated with trimethylsilyl trifluoromethanesulphonate (0.075 ml) at 0° C. The reaction mixture was stirred at 0° C. for 1 h, poured into a sodium bicarbonate solution, and extracted with EtOAc. The organic phase was washed with brine, dried over magnesium sulphate and concentrated. The residue was chromatographed on silica gel using EtOAc/hexane 1:1 as eluent to obtain acetic acid (2S,3R,4R,5S,6S)-4,5-diacetoxy-2-[(2S,4R)-4-acetylsulfanyl-1-methanesulfonyl-pyrrolidin-2-ylmethoxy]-6-methyl-tetrahydro-pyran-3-yl ester (0.105 g) as a syrup, MS: 543 (M+NH$_4^+$). Acetic acid (2S,3R,4R,5S,6S)-4,5-diacetoxy-2-[(2S,4R)-4-acetylsulfanyl-1-methanesulfonyl-pyrrolidin-2-ylmethoxy]-6-methyl-tetrahydro-pyran-3-yl ester (0.080 g) was reacted as described for the S-Acetyl deprotection (see below) to obtain (2S,3R,4R,5R,6S)-2-[(2S,4R)-4-mercapto-1-methanesulfonyl-pyrrolidin-2-ylmethoxy]-6-methyl-tetrahydro-pyran-3,4,5-triol (0.035 g) as a colourless foam, MS: 358 (MH$^+$).

Example 13

Ether, O-Nonbenzylether

Following Method A, (2S,4R)-(1-methanesulfonyl-4-tritylsulfanyl-pyrrolidin-2-yl)-methanol and tert-butyl bromoacetate gave (2S,4R)-(1-methanesulfonyl-4-tritylsulfanyl-pyrrolidin-2-ylmethoxy)-acetic acid tert-butyl ester, mp 98° C., slow dec., MS: 568 (MH$^+$).

In analogy: (2S,4R)-(1-methanesulfonyl-4-tritylsulfanyl-pyrrolidin-2-yl)-methanol and methyl (+/−)-2-bromo-4-methylvalerate gave after flash-chromatography on silica gel (Hexane/EtOAc 9:1 to 3:1) (R)- or (S)-2-[(2S,4R)-1-methanesulfonyl-4-tritylsulfanyl-pyrrolidin-2-ylmethoxy]-4-methyl-pentanoic acid methyl ester, MS: 582 (MH$^+$) and (S)- or (R)-2-[(2S,4R)-1-methanesulfonyl-4-tritylsulfanyl-pyrrolidin-2-ylmethoxy]-4-methyl-pentanoic acid methyl ester, MS: 582 (MH$^+$).

BOC-deprotection (See General Method for a Selective BOC-deprotection)

(2S,4R)-(1-methanesulfonyl-4-tritylsulfanyl-pyrrolidin-2-ylmethoxy)-acetic acid tert-butyl ester gave (2S,4R)-(1-methanesulfonyl-4-tritylsulfanyl-pyrrolidin-2-ylmethoxy)-acetic acid, MS: 512 (MH$^+$).

Hydrolysis in EtOH/THF (see General method for hydrolysis of an ester): (R)- or (S)-2-[(2S,4R)-1-methanesulfonyl-4-tritylsulfanyl-pyrrolidin-2-ylmethoxy]-4-methyl-pentanoic acid methyl ester gave (R)- or (S)-2-[(2S,4R)-1-methanesulfonyl-4-tritylsulfanyl-pyrrolidin-2-ylmethoxy]-4-methyl-pentanoic acid, MS: 568 (MH$^+$); and (S)- or (R)-2-[(2S,4R)-1-methanesulfonyl-4-tritylsulfanyl-pyrrolidin-2-ylmethoxy]-4-methyl-pentanoic acid methyl ester gave (R)- or (S)-2-[(2S,4R)-1-Methanesulfonyl-4-tritylsulfanyl-pyrrolidin-2-ylmethoxy]-4-methyl-pentanoic acid, MS: 568 (MH$^+$).

EDCI-coupling (see General method for EDCI-coupling) of (2S,4R)-(1-methanesulfonyl-4-tritylsulfanyl-pyrrolidin-2-ylmethoxy)-acetic acid with N-methylbenzylamine gave (2S,4R)-N-benzyl-2-(1-methanesulfonyl-4-tritylsulfanyl-pyrrolidin-2-ylmethoxy)-N-methyl-acetamide, MS: 615 (MH$^+$).

Following the TFA/triethylsilane trityl deprotection (Method 3), (2S,4R)-(1-methanesulfonyl-4-tritylsulfanyl-pyrrolidin-2-ylmethoxy)-acetic acid tert-butyl ester gave (2S,4R)-(4-mercapto-1-methanesulfonyl-pyrrolidin-2-ylmethoxy)-acetic acid, MS: 268 (M−H)$^-$;

(R)- or (S)-2-[(2S,4R)-1-methanesulfonyl-4-tritylsulfanyl-pyrrolidin-2-ylmethoxy]-4-methyl-pentanoic acid methyl ester gave (R)- or (S)-2-[(2S,4R)-4-mercapto-1-methanesulfonyl-pyrrolidin-2-ylmethoxy]-4methyl-pentanoic acid methyl ester, MS: 340 (MH$^+$);

(S)- or (R)-2-[(2S,4R)-1-methanesulfonyl-4-tritylsulfanyl-pyrrolidin-2-ylmethoxy]-4-methyl-pentanoic acid methyl ester gave (S)- or (R)-2-[(2S,4R)-4-mercapto-1-methanesulfonyl-pyrrolidin-2-ylmethoxy]-4-methyl-pentanoic acid methyl ester, MS: 340 (MH$^+$);

(R)- or (S)-2-[(2S,4R)-1-methanesulfonyl-4-tritylsulfanyl-pyrrolidin-2-ylmethoxy]-4-methyl-pentanoic acid gave (R)- or (S)-2-[(2S,4R)-4-mercapto-1-methanesulfonyl-pyrrolidin-2-ylmethoxy]-4-methyl-pentanoic acid, MS: 324 (M–H)$^-$;

(R)- or (S)-2-[(2S,4R)-1-methanesulfonyl-4-tritylsulfanyl-pyrrolidin-2-ylmethoxy]-4-methyl-pentanoic acid gave (S)- or (R)-2-[(2S,4R)-4-Mercapto-1-methanesulfonyl-pyrrolidin-2-ylmethoxy]-4-methyl-pentanoic acid, MS: 324 (M–H)$^-$;

(2S,4R)-N-benzyl-2-(1-methanesulfonyl-4-tritylsulfanyl-pyrrolidin-2-ylmethoxy)-N-methyl-acetamide gave (2S,4R)-N-Benzyl-2-(4-mercapto-1-methanesulfonyl-pyrrolidin-2-ylmethoxy)-N-methyl-acetamide, MS: 373 (MH$^+$).

In analogy: (2S,4R)-(1-methanesulfonyl-4-tritylsulfanyl-pyrrolidin-2-yl)-methanol and methyl (+/−)-alpha-bromophenylacetate gave after the separation of the diastereomers and deprotection of the trityl group (Method 3) (R)- or (S)-[(2S,4R)-4-mercapto-1-methanesulfonyl-pyrrolidin-2-ylmethoxy]-phenyl-acetic acid methyl ester, MS: 359 (M); and (S)- or (R)-[(2S,4R)-4-mercapto-1-methanesulfonyl-pyrrolidin-2-ylmethoxy]-phenyl-acetic acid methyl ester, MS: 359 (M).

Example 14
N-Pyrrolidin-Derivatisation of the Ethers
Starting Materials

A solution of 15.5 g (32.59 mmol) (2S,4R)-2-hydroxymethyl-4-tritylsulfanyl-pyrrolidine-1-carboxylic acid tert-butyl ester and 24.7 g (109.77 mmol) 2,4,5-trifluorobenzylbromide in 700 ml DMF at 0° C. was treated with 2.28 g (52.14 mmol) of 55% NaH in 4 portions and warmed up to room temperature during 7 h. The reaction was cooled to 0° C. and treated with 500 ml aqueous saturated NH$_4$Cl solution, extracted with EtOAc (3×). The organic phase was washed with 10% NaCl dried over Na$_2$SO$_4$ and evaporated. Flash column chromatography on silica gel with hexane/EtOAc (9:1 to 8.5:1.5) gave 9.37 g (46%) of (2S,4R)-2-(2,4,5-trifluoro-benzyloxymethyl)-4-tritylsulfanyl-pyrrolidine-1-carboxylic acid tert-butyl ester, MS: 620 (MH$^+$).

In analogy: (2S,4S)-4-chloro-2-hydroxymethyl-pyrrolidine-1-carboxylic acid tert-butyl ester gave (2S,4S)-4-chloro-2-(2,4,5-trifluoro-benzyloxymethyl)-pyrrolidine-1-carboxylic acid tert-butyl ester, MS: 379 (M).

A solution of 9.37 g (15.11 mmol) (2S,4R)-2-(2,4,5-trifluoro-benzyloxymethyl)-4-tritylsulfanyl-pyrrolidine-1-carboxylic acid tert-butyl ester in 30 ml CH$_2$Cl$_2$ was treated at −20° C. with 34 ml TFA and warmed up to room temperature during 5.5 h. The reaction was evaporated and treated with aqueous saturated NaHCO$_3$ solution/EtOAc (3×) to give 7.77 g (quantitative) (2S,4R)-2-(2,4,5-trifluoro-benzyloxymethyl)-4-tritylsulfanyl-pyrrolidine, MS: 520 (M).

In analogy: The reaction of (2S,4R)-2-hydroxymethyl-4-tritylsulfanyl-pyrrolidine-1-carboxylic acid tert-butyl ester with benzylbromide gave (2S,4R)-2-benzyloxymethyl-4-tritylsulfanyl-pyrrolidine, MS: 466 (MH$^+$).

Example 14.a
Ether, Carbamates (Table 3 and Table 4)

Carbamate, Method A: A solution of 1.9 g (4.1 mmol) (2S,4R)-2-benzyloxy-methyl-4-tritylsulfanyl-pyrrolidine in 25 ml THF at 0° C. was treated with 0.57 ml (4.5 mmol) phenyl chloroformate and 0.41 ml (5.1 mmol) pyridine. After 2 h at room temperature the reaction was worked up with 1N HCl/EtOAc (3×), the organic phases were washed with H$_2$O, aqueous saturated NaHCO$_3$, dried and evaporated to give 2.6 g (quantitative) (2S,4R)-2-benzyloxymethyl-4-tritylsulfanyl-pyrrolidine-1-carboxylic acid phenyl ester, MS: 586 (MH$^+$).

Trityl deprotection (Method 3) (7 h at 0° C.) gave (2S,4R)-2-benzyloxymethyl-4-mercapto-pyrrolidine-1-carboxylic acid phenyl ester, MS: 343 (M).

Carbamate, Method B: A solution of 0.19 ml (1.58 mmol) trichloromethyl-chloroformate in 20 ml CH$_2$Cl$_2$ was treated at 0° C. with 0.28 ml (3 mmol) 2-fluorophenol and 0.35 ml (3 mmol) quinoline and then stirred for 3 h at room temperature. The reaction was then cooled (0° C.) and a solution of 0.52 g (1 mmol) (2S,4R)-2-(2,4,5-trifluoro-benzyloxymethyl)-4-tritylsulfanyl-pyrrolidine and 0.2 ml (2.5 mmol) pyridine in 3 ml CH$_2$Cl$_2$ was added, followed by 122 mg (1 mmol) DMAP. After 3 h at 0° C. the reaction was evaporated and poured into aqueous 10% KHSO$_4$/Et$_2$O (3×). The organic phases were washed with aqueous 10% NaCl solution, dried over Na$_2$SO$_4$ and evaporated. Flash chromatography on silica gel (hexane/EtOAc 9:1) gave 0.39 g (60%) (2S,4R)-2-(2,4,5-trifluoro-benzyloxymethyl)-4-tritylsulfanyl-pyrrolidine-1-carboxylic acid 2-fluoro-phenyl ester, MS: 658 (MH$^+$).

Trityl deprotection (Method 3) gave (2S,4R)-4-mercapto-2-(2,4,5-trifluoro-benzyloxymethyl)-pyrrolidine-1-carboxylic acid 2-fluoro-phenyl ester, MS: 416 (MH$^+$).

In analogy: a) (2S,4R)-2-(2,4,5-trifluoro-benzyloxymethyl)-4-tritylsulfanyl-pyrrolidine and DL-Leucyc acid isopropyl ester gave after separation on silica gel with hexane/EtOAc 9:1 (2S,4R)-2-(2,4,5-trifluoro-benzyloxymethyl)-4-tritylsulfanyl-pyrrolidine-1-carboxylic acid (S)- or (R)-1-isopropoxycarbonyl-3-methyl-butyl ester, MS: 720 (MH$^+$) and (2S,4R)-2-(2,4,5-trifluoro-benzyloxymethyl)-4-tritylsulfanyl-pyrrolidine-1-carboxylic acid (R)- or (S)-1-isopropoxycarbonyl-3-methyl-butyl ester, MS: 720 (MH$^+$).

(2S,4R)-2-(2,4,5-trifluoro-benzyloxymethyl)-4-tritylsulfanyl-pyrrolidine and ethyl-3-hydroxy-benzoate gave (2S,4R)-2-(2,4,5-trifluoro-benzyloxymethyl)-4-tritylsulfanyl-pyrrolidine-1-carboxylic acid 3-ethoxycarbonyl-phenyl ester, MS: 712 (MH$^+$).

(2S,4R)-2-(2,4,5-trifluoro-benzyloxymethyl)-4-tritylsulfanyl-pyrrolidine and ethylglycolate gave (2S,4R)-2-(2,4,5-Trifluoro-benzyloxymethyl)-4-tritylsulfanyl-pyrrolidine-1-carboxylic acid ethoxycarbonylmethyl ester, MS: 650 (MH$^+$).

Trityl deprotection (Method 3) of (2S,4R)-2-(2,4,5-trifluoro-benzyloxymethyl)-4-tritylsulfanyl-pyrrolidine-1-carboxylic acid (S)- and (R)-1-isopropoxycarbonyl-3-methyl-butyl ester gave (2S,4R)-4-mercapto-2-(2,4,5-trifluoro-benzyloxymethyl)-pyrrolidine-1-carboxylic acid (S)- and (R)-1-isopropoxycarbonyl-3-methyl-butyl ester, MS: 478 (MH$^+$).

In analogy: (2S,4R)-2-(2,4,5-trifluoro-benzyloxymethyl)-4-tritylsulfanyl-pyrrolidine-1-carboxylic acid 3-ethoxycarbonyl-phenyl ester gave (2S,4R)-4-mercapto-2-(2,4,5-trifluoro-benzyloxymethyl)-pyrrolidine-1-carboxylic acid 3-ethoxycarbonyl-phenyl ester, MS: 470 (MH$^+$).

b) Hydrolysis with 1 N NaOH (see General method for hydrolysis of an ester) in dioxane of (2S,4R)-2-(2,4,5-trifluoro-benzyloxymethyl)-4-tritylsulfanyl-pyrrolidine-1-carboxylic acid (S)- or (R)-1-isopropoxycarbonyl-3-methyl-butyl ester gave (2S,4R)-2-(2,4,5-trifluoro-benzyloxymethyl)-4-tritylsulfanyl-pyrrolidine-1-carboxylic acid (S)- or (R)-1-carboxy-3-methyl-butyl ester, MS: 678 (MH$^+$) and (2S,4R)-2-(2,4,5-trifluoro-benzyloxymethyl)-4-tritylsulfanyl-pyrrolidine-1-carboxylic acid (R)- or (S)-1-isopropoxycarbonyl-3-methyl-butyl ester gave (2S,4R)-2-(2,4,5-trifluoro-benzyloxymethyl)-4-tritylsulfanyl-pyrrolidine-1-carboxylic acid (R)- or (S)-1-carboxy-3-methyl-butyl ester, MS: 678 (MH$^+$).

In analogy: (2S,4R)-2-(2,4,5-trifluoro-benzyloxymethyl)-4-tritylsulfanyl-pyrrolidine-1-carboxylic acid 3-ethoxycarbonyl-phenyl ester gave (2S,4R)-2-(2,4,5-trifluoro-benzyloxymethyl)-4-tritylsulfanyl-pyrrolidine-1-carboxylic acid 3-carboxy-phenyl ester, MS: 684 (MH$^+$).

(2S,4R)-2-(2,4,5-Trifluoro-benzyloxymethyl)-4-tritylsulfanyl-pyrrolidine-1-carboxylic acid ethoxycarbonyl-methyl ester gave (2S,4R)-2-(2,4,5-Trifluoro-benzyloxymethyl)-4-tritylsulfanyl-pyrrolidine-1-carboxylic acid carboxymethyl ester, MS: 620 (M–H)$^-$.

Trityl deprotection (Method 3): (2S,4R)-2-(2,4,5-trifluoro-benzyloxymethyl)-4-tritylsulfanyl-pyrrolidine-1-carboxylic acid (S)- or (R)-1-carboxy-3-methyl-butyl ester gave (2S,4R)-4-mercapto-2-(2,4,5-trifluoro-benzyloxymethyl)-pyrrolidine-1-carboxylic acid (S)- or (R)-1-carboxy-3-methyl-butyl ester, MS: 434 (M–H$^-$) and (2S,4R)-2-(2,4,5-trifluoro-benzyloxymethyl)-4-tritylsulfanyl-pyrrolidine-1-carboxylic acid (R)- or (S)-1-carboxy-3-methyl-butyl ester gave (2S,4R)-4-mercapto-2-(2,4,5-trifluoro-benzyloxymethyl)-pyrrolidine-1-carboxylic acid (R)- or (S)-1-carboxy-3-methyl-butyl ester, MS: 434 (M–H$^-$).

(2S,4R)-2-(2,4,5-Trifluoro-benzyloxymethyl)-4-tritylsulfanyl-pyrrolidine-1-carboxylic acid 3-carboxy-phenyl ester gave (2S,4R)-4-mercapto-2-(2,4,5-trifluoro-benzyloxymethyl)-pyrrolidine-1-carboxylic acid (S)- or (R)-1-carboxy-3-methyl-butyl ester, MS: 440 (M–H$^-$).

(2S,4R)-2-(2,4,5-Trifluoro-benzyloxymethyl)-4-tritylsulfanyl-pyrrolidine-1-carboxylic acid carboxymethyl ester gave (2S,4R)-4-Mercapto-2-(2,4,5-trifluoro-benzyloxymethyl)-pyrrolidine-1-carboxylic acid carboxymethyl ester, MS: 380 (MH$^+$).

Carbamate, Method C: A solution of 0.07 ml (0.55 mmol) trichloromethyl-chloroformate in 7 ml CH$_2$Cl$_2$ was treated at 0° C. with 0.13 ml (1.1 mmol) quinoline and after 15 min with 0.52 g (1 mmol) (2S,4R)-2-(2,4,5-trifluoro-benzyloxymethyl)-4-tritylsulfanyl-pyrrolidine in 7 ml CH$_2$Cl$_2$. After 2 h at 0° C. the CH$_2$Cl$_2$ was evaporated. The residue was dissolved in 15 ml THF, treated at 0° C. with 0.27 ml (2.1 mmol) methyl salicylate, 96 mg (2.4 mmol) of 55% NaH and 166 mg (1 mmol) of KI. The reaction was stirred at room temperature over night, cooled (0° C.) and after the addition of 44 mg (1 mmol) of 55% NaH refluxed for 3 h. The reaction was partitioned between aqueous 10% KHSO$_4$/EtOAc (3×300). The organic phases were washed with aqueous 10% NaCl, dried (Na$_2$SO$_4$) and evaporated. Flash chromatography on silica gel (Hexane/EtOAc 9:1) gave 0.48 g (69%) (2S,4R)-2-(2,4,5-trifluoro-benzyloxymethyl)-4-tritylsulfanyl-pyrrolidine-1-carboxylic acid 2-methoxycarbonyl-phenyl ester, MS: 698 (MH$^+$).

(Method 3): A solution of 0.4 g (0.58 mmol) (2S,4R)-2-(2,4,5-trifluoro-benzyloxymethyl)-4-tritylsulfanyl-pyrrolidine-1-carboxylic acid 2-methoxycarbonyl-phenyl ester in 5.8 ml TFA was treated at 0° C. with 0.92 ml (5.78 mmol) triethylsilane and after 10 min at room temperature evaporated and purified by flash chromatography on silica gel (Hexane/EtOAc 4:1) to give 0.22 (82%) (2S,4R)-4-mercapto-2-(2,4,5-trifluoro-benzyloxymethyl)-pyrrolidine-1-carboxylic acid 2-methoxycarbonyl-phenyl ester, MS: 456 (MH$^+$).

(Method 4): A solution of 0.32 mmol trityl-protected compound was dissolved in 1.5 ml acetonitril/0.4 ml TFA/0.1 ml triethylsilane and after 1 night at RT purified by prep HPLC (RP18, CH$_3$CN/H$_2$O 80:20 to 95:5) to give the free thiols.

By the reaction of (2S,4R)-2-Benzyloxymethyl-4-tritylsulfanyl-pyrrolidine with the second educt in table 3 the following compounds were obtained:

TABLE 3

| | Name | 2. Educt | Method | MS | |
|---|---|---|---|---|---|
| 1 | (2S,4R)-2-Benzyloxymethyl-4-mercapto-pyrrolidine-1-carboxylic acid phenyl ester | PHENYL CHLOROFORMATE | A | M | 343 |
| 2 | (2S,4R)-2-Benzyloxymethyl-4-mercapto-pyrrolidine-1-carboxylic acid isopropyl ester | ISOPROPYL CHLOROFORMATE | A | M+H+ | 310 |
| 3 | (2S,4R)-2-Benzyloxymethyl-4-mercapto-pyrrolidine-1-carboxylic acid 2-chloro-ethyl ester | 2-CHLOROETHYL CHLOROFORMATE | A | M+H+ | 330 |
| 4 | (2S,4R)-2-Benzyloxymethyl-4-mercapto-pyrrolidine-1-carboxylic acid benzyl ester | BENZYL CHLOROFORMATE | A | M+H+ | 358 |
| 5 | (2S,4R)-2-Benzyloxymethyl-4-mercapto-pyrrolidine-1-carboxylic acid naphthalen-2-yl ester | CHLOROFORMIC ACID 2-NAPHTHYL ESTER | A | M+H+ | 394 |

TABLE 3-continued

| | Name | 2. Educt | Method | MS | |
|---|---|---|---|---|---|
| 6 | (2S,4R)-2-Benzyloxymethyl-4-mercapto-pyrrolidine-1-carboxylic acid pentyl ester | CHLOROFORMIC ACID N-AMYL ESTER | A | M+H+ | 338 |
| 7 | (2S,4R)-2-Benzyloxymethyl-4-mercapto-pyrrolidine-1-carboxylic acid isobutyl ester | ISOBUTYL CHLOROFORMATE | A | M+H+ | 324 |
| 8 | (2S,4R)-2-Benzyloxymethyl-4-mercapto-pyrrolidine-1-carboxylic acid methyl ester | METHYL CHLOROFORMATE | A | M | 281 |
| 9 | (2S,4R)-2-Benzyloxymethyl-4-mercapto-pyrrolidine-1-carboxylic acid butyl ester | BUTYL CHLOROFORMATE | A | M+H+ | 324 |

By the reaction of (2S,4R)-2-(2,4,5-trifluoro-benzyloxymethyl)-4-tritylsulfanyl-pyrrolidine with the second educt mentioned in table 4 the following compounds were obtained:

TABLE 4

| | Name | 2. Educt | Method | MS | |
|---|---|---|---|---|---|
| 1 | (2S,4R)-4-Mercapto-2-(2,4,5-trifluoro-benzyloxymethyl)-pyrrolidine-1-carboxylic acid isopropyl ester | ISOPROPYL CHLOROFORMATE | A | M+H+ | 364 |
| 2 | (2S,4R)-4-Mercapto-2-(2,4,5-trifluoro-benzyloxymethyl)-pyrrolidine-1-carboxylic acid phenyl ester | PHENYL CHLOROFORMATE | A | M+H+ | 398 |
| 3 | (2S,4R)-4-Mercapto-2-(2,4,5-trifluoro-benzyloxymethyl)-pyrrolidine-1-carboxylic acid 2-chloro-ethyl ester | 2-CHLOROETHYL CHLOROFORMATE | A | M+H+ | 384 |
| 4 | (2S,4R)-4-Mercapto-2-(2,4,5-trifluoro-benzyloxymethyl)-pyrrolidine-1-carboxylic acid benzyl ester | BENZYL CHLOROFORMATE | A | M+H+ | 412 |
| 5 | (2S,4R)-4-Mercapto-2-(2,4,5-trifluoro-benzyloxymethyl)-pyrrolidine-1-carboxylic acid naphthalen-2-yl ester | CHLOROFORMIC ACID 2-NAPHTHYL ESTER | A | M+H+ | 448 |
| 6 | (2S,4R)-4-Mercapto-2-(2,4,5-trifluoro-benzyloxymethyl)-pyrrolidine-1-carboxylic acid pentyl ester | CHLOROFORMIC ACID N-AMYL ESTER | A | M+H+ | 392 |
| 7 | (2S,4R)-4-Mercapto-2-(2,4,5-trifluoro-benzyloxymethyl)-pyrrolidine-1-carboxylic acid isobutyl ester | ISOBUTYL CHLOROFORMATE | A | M+H+ | 378 |
| 8 | (2S,4R)-4-Mercapto-2-(2,4,5-trifluoro-benzyloxymethyl)-pyrrolidine-1-carboxylic acid methyl ester | METHYL CHLOROFORMATE | A | M+H+ | 336 |
| 9 | (2S,4R)-4-Mercapto-2-(2,4,5-trifluoro-benzyloxymethyl)-pyrrolidine-1-carboxylic acid 4-fluoro-phenyl ester | 4-FLUOROPHENYL CHLOROFORMATE | A | M+H+ | 416 |
| 10 | (2S,4R)-4-Mercapto-2-(2,4,5-trifluoro-benzyloxymethyl)-pyrrolidine-1-carboxylic acid 2,3-dihydro-benzo[1,4]dioxin-5-yl ester | Lit [1] | A | M+H+ | 456 |
| 11 | (2S,4R)-4-Mercapto-2-(2,4,5-trifluoro-benzyloxymethyl)-pyrrolidine-1-carboxylic acid 4-methoxycarbonyl-phenyl ester | 4-METHOXYCARBONYL-PHENYL CHLOROFORMATE | A | M+H+ | 456 |
| 12 | (2S,4R)-4-Mercapto-2-(2,4,5-trifluoro-benzyloxymethyl)-pyrrolidine-1-carboxylic acid 4-chloro-phenyl ester | 4-CHLOROPHENYL CHLOROFORMATE | A | M+H+ | 432 |
| 13 | (2S,4R)-4-Mercapto-2-(2,4,5-trifluoro-benzyloxymethyl)-pyrrolidine-1-carboxylic acid p-tolyl ester | P-TOLYL CHLOROFORMATE | A | M+H+ | 412 |
| 14 | (2S,4R)-4-Mercapto-2-(2,4,5-trifluoro-benzyloxymethyl)-pyrrolidine-1-carboxylic acid 4-bromo-phenyl ester | 4-BROMOPHENYL CHLOROFORMATE | A | M+H+, 1Br | 476 |
| 15 | (2S,4R)-4-Mercapto-2-(2,4,5-trifluoro-benzyloxymethyl)-pyrrolidine-1-carboxylic acid prop-2-ynyl ester | PROPARGYL CHLOROFORMATE | A | M+H+ | 36 |
| 16 | (2S,4R)-4-Mercapto-2-(2,4,5-trifluoro-benzyloxymethyl)-pyrrolidine-1-carboxylic acid but-3-enyl ester | 3-BUTENYL CHLOROFORMATE | A | M+H+ | 376 |
| 17 | (2S,4R)-4-Mercapto-2-(2,4,5-trifluoro-benzyloxymethyl)-pyrrolidine-1-carboxylic acid 2-isopropyl-5-methyl-cyclohexyl ester | (−)-MENTHYL CHLOROFORMATE | A | M+H+ | 460 |
| 18 | (2S,4R)-4-Mercapto-2-(2,4,5-trifluoro-benzyloxymethyl)-pyrrolidine-1-carboxylic acid phenethyl ester | PHENETHYLALCOHOL | B | M+H+ | 426 |
| 19 | (2S,4R)-4-Mercapto-2-(2,4,5-trifluoro-benzyloxymethyl)-pyrrolidine-1-carboxylic acid 2,2,2-trifluoro-ethyl ester | 2,2,2-TRIFLUORETHANOL | B | M | 403 |

TABLE 4-continued

| Name | 2. Educt | Method | MS | |
|---|---|---|---|---|
| 20 (2S,4R)-4-Mercapto-2-(2,4,5-trifluoro-benzyloxymethyl)-pyrrolidine-1-carboxylic acid 4-methoxy-phenyl ester | 4-METHOXYPHENYL CHLOROFORMATE | A | M+H+ | 428 |
| 21 (2S,4R)-4-Mercapto-2-(2,4,5-trifluoro-benzyloxymethyl)-pyrrolidine-1-carboxylic acid 2-methoxy-ethyl ester | CHLOROFORMIC ACID 2-METHOXYETHYL ESTER | A | M+H+ | 380 |
| 22 (2S,4R)-4-Mercapto-2-(2,4,5-trifluoro-benzyloxymethyl)-pyrrolidine-1-carboxylic acid butyl ester | BUTYL CHLOROFORMATE | A | M+H+ | 370 |
| 23 (2S,4R)-4-Mercapto-2-(2,4,5-trifluoro-benzyloxymethyl)-pyrrolidine-1-carboxylic acid ethyl ester | ETHYL CHLOROFORMATE | A | M+H+ | 350 |
| 24 (2S,4R)-4-Mercapto-2-(2,4,5-trifluoro-benzyloxymethyl)-pyrrolidine-1-carboxylic acid propyl ester | PROPYL CHLOROFORMATE | A | M+H+ | 364 |
| 25 (2S,4R)-4-Mercapto-2-(2,4,5-trifluoro-benzyloxymethyl)-pyrrolidine-1-carboxylic acid ethoxycarbonylmethyl ester | ETHYLGLYCOLATE | B | M+H+ | 408 |
| 26 (2S,4R)-4-Mercapto-2-(2,4,5-trifluoro-benzyloxymethyl)-pyrrolidine-1-carboxylic acid hexyl ester | CHLOROFORMIC ACID N-HEXYL ESTER | A | M+H+ | 406 |
| 27 (2S,4R)-4-Mercapto-2-(2,4,5-trifluoro-benzyloxymethyl)-pyrrolidine-1-carboxylic acid 2-fluoro-benzyl ester | 2-FLUOROBENZYL ALCOHOL | B | M+H+ | 430 |
| 28 (2S,4R)-4-Mercapto-2-(2,4,5-trifluoro-benzyloxymethyl)-pyrrolidine-1-carboxylic acid 2-fluoro-phenyl ester | 2-FLUOROPHENOL | B, described | M+H+ | 416 |
| 29 (2S,4R)-4-Mercapto-2-(2,4,5-trifluoro-benzyloxymethyl)-pyrrolidine-1-carboxylic acid 2-amino-ethyl ester; compound with trifluoro-acetic acid | BOC-AMINOETHANOL | C | M+H+ | 365 |
| 30 (2S,4R)-4-Mercapto-2-(2,4,5-trifluoro-benzyloxymethyl)-pyrrolidine-1-carboxylic acid pyridin-4-ylmethyl ester; compound with trifluoro-acetic acid | 4-(HYDROXYMETHYL) PYRIDINE | B | M+H+ | 413 |
| 31 (2S,4R)-4-Mercapto-2-(2,4,5-trifluoro-benzyloxymethyl)-pyrrolidine-1-carboxylic acid o-tolyl ester | 2-METHYLPHENOL | B | M+H+ | 412 |
| 32 (2S,4R)-4-Mercapto-2-(2,4,5-trifluoro-benzyloxymethyl)-pyrrolidine-1-carboxylic acid 2-methoxy-phenyl ester | 2-METHOXYPHENOL | B | M+H+ | 428 |
| 33 (2S,4R)-4-Mercapto-2-(2,4,5-trifluoro-benzyloxymethyl)-pyrrolidine-1-carboxylic acid 2-methoxycarbonyl-phenyl ester | METHYL SALICYLATE | C, described | M+H+ | 456 |
| 34 (2S,4R)-4-Mercapto-2-(2,4,5-trifluoro-benzyloxymethyl)-pyrrolidine-1-carboxylic acid 2-dimethylamino-ethyl ester; compound with trifluoro-acetic acid | 2-DIMETHYLAMINOETHANOL | B | M+H+ | 393 |
| 35 (2S,4R)-4-Mercapto-2-(2,4,5-trifluoro-benzyloxymethyl)-pyrrolidine-1-carboxylic acid 2-cyano-phenyl ester | 2-HYDROXYBENZONITRILE | B | M+H+ | 423 |
| 36 (2S,4R)-4-Mercapto-2-(2,4,5-trifluoro-benzyloxymethyl)-pyrrolidine-1-carboxylic acid 3-fluoro-phenyl ester | 3-FLUOROPHENOL | B | M+H+ | 416 |
| 37 (2S,4R)-4-Mercapto-2-(2,4,5-trifluoro-benzyloxymethyl)-pyrrolidine-1-carboxylic acid 2-bromo-phenyl ester | 2-BROMOPHENOL | B | M+H+ | 477 |
| 38 (2S,4R)-4-Mercapto-2-(2,4,5-trifluoro-benzyloxymethyl)-pyrrolidine-1-carboxylic acid naphthalen-1-ylmethyl ester | 1-NAPHTHALENEMETHANOL | B | M+H+ | 462 |
| 39 (2S,4R)-4-Mercapto-2-(2,4,5-trifluoro-benzyloxymethyl)-pyrrolidine-1-carboxylic acid 2-naphthalen-2-yl-ethyl ester | 2-NAPHTHALENEETHANOL | B | M+H+ | 476 |
| 40 (2S,4R)-4-Mercapto-2-(2,4,5-trifluoro-benzyloxymethyl)-pyrrolidine-1-carboxylic acid 2-naphthalen-1-yl-ethyl ester | 1-NAPHTHALENEETHANOL | B | M+H+ | 476 |
| 41 (2S,4R)-4-Mercapto-2-(2,4,5-trifluoro-benzyloxymethyl)-pyrrolidine-1-carboxylic acid 3-phenoxy-phenyl ester | 3-PHENOXYPHENOL | B | M+H+ | 490 |
| 42 (2S,4R)-4-Mercapto-2-(2,4,5-trifluoro-benzyloxymethyl)-pyrrolidine-1-carboxylic acid biphenyl-3-yl ester | 3-PHENYLPHENOL | B | M+H+ | 474 |
| 43 (2S,4R)-4-Mercapto-2-(2,4,5-trifluoro-benzyloxymethyl)-pyrrolidine-1-carboxylic acid 4-cyclohexyl-phenyl ester | 4-CYCLOHEXYLPHENOL | B | M+H+ | 480 |

TABLE 4-continued

| Name | 2. Educt | Method | MS | |
|---|---|---|---|---|
| 44 (2S,4R)-4-Mercapto-2-(2,4,5-trifluoro-benzyloxymethyl)-pyrrolidine-1-carboxylic acid biphenyl-2-yl ester | 2-PHENYLPHENOL | B | M+H+ | 474 |
| 45 (2S,4R)-4-Mercapto-2-(2,4,5-trifluoro-benzyloxymethyl)-pyrrolidine-1-carboxylic acid 5,6,7,8-tetrahydro-naphthalen-1-yl ester | 5,6,7,8-TETRAHYDRO-1-NAPHTHOL | B | M+H+ | 452 |
| 46 (2S,4R)-4-Mercapto-2-(2,4,5-trifluoro-benzyloxymethyl)-pyrrolidine-1-carboxylic acid naphthalen-2-ylmethyl ester | 2-NAPHTHALENEMETHANOL | B | M+H+ | 462 |
| 47 (2S,4R)-4-Mercapto-2-(2,4,5-trifluoro-benzyloxymethyl)-pyrrolidine-1-carboxylic acid biphenyl-4-yl ester | 4-PHENYLPHENOL | B | M+H+ | 474 |
| 48 (2S,4R)-4-Mercapto-2-(2,4,5-trifluoro-benzyloxymethyl)-pyrrolidine-1-carboxylic acid 2-chloro-phenyl ester | 2CHLOROPHENOL | B | M+H+ | 432 |
| 49 (2S,4R)-4-Mercapto-2-(2,4,5-trifluoro-benzyloxymethyl)-pyrrolidine-1-carboxylic acid isoquinolin-5-yl ester; compound with trifluoro-acetic acid | 5-HYDROXYISOQUINOLINE | B | M+H+ | 563 |
| 50 (2S,4R)-4-Mercapto-2-(2,4,5-trifluoro-benzyloxymethyl)-pyrrolidine-1-carboxylic acid quinolin-4-yl ester trifluoroacetate (1:1) | 4-HYDROXYQUINOLINE | B | M+H+ | 563 |
| 51 (2S,4R)-4-Mercapto-2-(2,4,5-trifluoro-benzyloxymethyl)-pyrrolidine-1-carboxylic acid quinolin-8-yl ester trifluoroacetate (1:1) | 8-HYDROXYQUINOLINE | B | M+H+ | 563 |
| 52 (2S,4R)-4-Mercapto-2-(2,4,5-trifluoro-benzyloxymethyl)-pyrrolidine-1-carboxylic acid quinolin-5-yl ester trifluoroacetate (1:1) | 5-HYDROXYQUINOLINE | B | M+H+ | 563 |
| 53 (2S,4R)-4-Mercapto-2-(2,4,5-trifluoro-benzyloxymethyl)-pyrrolidine-1-carboxylic acid isoquinolin-1-yl ester trifluoroacetate (1:1) | ISOCARBOSTYRIL | B | M+H+ | 563 |
| 54 (2S,4R)-4-Mercapto-2-(2,4,5-trifluoro-benzyloxymethyl)-pyrrolidine-1-carboxylic acid benzo[1,3]dioxol-4-yl ester | Lit [2] | B | M+H+ | 442 |
| 55 (2S,4R)-4-Mercapto-2-(2,4,5-trifluoro-benzyloxymethyl)-pyrrolidine-1-carboxylic acid naphthalen-1-yl ester | 1-NAPHTOL | B | M+H+ | 448 |
| 56 (2S,4R)-4-Mercapto-2-(2,4,5-trifluoro-benzyloxymethyl)-pyrrolidine-1-carboxylic acid pyridin-3-yl ester trifluoroacetate (1:1) | 3-HYDROXYPYRIDINE | B | M+H+ | 513 |
| 57 (2S,4R)-4-Mercapto-2-(2,4,5-trifluoro-benzyloxymethyl)-pyrrolidine-1-carboxylic acid pyridin-2-yl ester trifluoroacetate (1:1) | 2-HYDROXYPYRIDINE | B | M+H+ | 513 |
| 58 (2S,4R)-4-Mercapto-2-(2,4,5-trifluoro-benzyloxymethyl)-pyrrolidine-1-carboxylic acid quinolin-6-yl ester trifluoroacetate (1:1) | 6-HYDROXYQUINOLINE | B | M+H+ | 563 |
| 59 (2S,4R)-4-Mercapto-2-(2,4,5-trifluoro-benzyloxymethyl)-pyrrolidine-1-carboxylic acid 2-(4-methyl-thiazol-5-yl)-ethyl ester trifluoroacetate (1:1) | 5-(2-HYDROXYETHYL)-4-METHYLTHIAZOLE | B | M+H+ | 561 |
| 60 (2S,4R)-4-Mercapto-2-(2,4,5-trifluoro-benzyloxymethyl)-pyrrolidine-1-carboxylic acid 3-pyridin-4-yl-propyl ester trifluoroacetate (1:1) | 4-PYRIDINEPROPANOL | B | M+H+ | 555 |
| 61 (2S,4R)-4-Mercapto-2-(2,4,5-trifluoro-benzyloxymethyl)-pyrrolidine-1-carboxylic acid pyridin-2-ylmethyl ester | PYRIDINE-2-METHANOL | B | M+H+ | 527 |
| 62 (2S,4R)-4-Mercapto-2-(2,4,5-trifluoro-benzyloxymethyl)-pyrrolidine-1-carboxylic acid 3-chloro-phenyl ester | 2-CHLOROOPHENOL | B | M+H+ | 432 |
| 63 (2S,4R,3R)-4-Mercapto-2-(2,4,5-trifluoro-benzyloxymethyl)-pyrrolidine-1-carboxylic acid (R)-1-benzyloxycarbonyl-3-methyl-butyl ester | Lit [3] | B | M+H+ | 526 |
| 64 (2S,4R)-4-Mercapto-2-(2,4,5-trifluoro-benzyloxymethyl)-pyrrolidine-1-carboxylic acid 5,7-dichloro-quinolin-8-yl ester; compound with trifluoro-acetic acid | 5,7-DICHLORO-8-HYDROXYQUINOLINE | B | M+H+ | 632 |
| 65 (2S,4R)-4-Mercapto-2-(2,4,5-trifluoro-benzyloxymethyl)-pyrrolidine-1-carboxylic acid cyclohexyl ester | CYCLOHEXYL CHLOROFORMATE | A | M+H+ | 404 |
| 66 (2S,4R)-4-Mercapto-2-(2,4,5-trifluoro-benzyloxymethyl)-pyrrolidine-1-carboxylic acid 3-methoxy-phenyl ester | 3-Methoxy-phenol | B | M+H+ | 428 |
| 67 (2S,4R)-4-Mercapto-2-(2,4,5-trifluoro-benzyloxymethyl)-pyrrolidine-1-carboxylic acid 3,4-dimethoxy-phenyl ester | 3,4-Dimethoxy-phenol | C | M+H+ | 458 |

TABLE 4-continued

| Name | 2. Educt | Method | MS |
| --- | --- | --- | --- |
| 68 (2S,4R)-4-Mercapto-2-(2,4,5-trifluoro-benzyloxymethyl)-pyrrolidine-1-carboxylic acid 2-carboxy-phenyl ester | | C | M–H– 440 |

[1] 5-(1,4-benzodioxan)-chloroformate: Eitel, Alfred; Hammann, Ingeborg. Benzodioxan-N-methylcarbamates useful as insecticides or acaricides. S. African, 14 pp. CODEN: SFXXAB. ZA 6800512 680627. CAN 70:57861 CAPLUS

[2] Benzo[1,3]dioxol-4-ol: Dallacker, Franz; Holschbach, Markus; Holschbach, Ute; Konings, A. W. T. 1,3-Benzodioxole derivatives as radioprotectants. 5. Preparation of 4- and 5-hydroxy-1,3-benzodioxole derivatives. Chem.-Ztg. (1990), 114(7–8), 225–8.

[3] (2R)-2-Hydroxy-4-methyl-pentanoic acid benzyl ester: Brown, Frank K.; Brown, Peter J.; Bickett, D. Mark; Chambers, C. Lynn; Davies, H. Geoff; Deaton, David N.; Drewry, David; Foley, Michael; McElroy, Andrew B.; et al. Matrix Metalloproteinase Inhibit

[4] 2-Hydroxy-benzoic acid tert-butyl ester: Widmer, Ulrich. A convenient preparation of tert-butyl esters. Synthesis (1983), Issue 2, 135–6.

Example 14.b
Ether, Carbamate via Thioacetate

A solution of 0.873 mg (2 mmol) (2S,4S)-4-chloro-2-(2,4,5-trifluoro-benzyloxymethyl)-pyrrolidine-1-carboxylic acid tert-butyl ester was dissolved in 20 ml DMF and after the addition of 0.343 mg (3 mmol) potassium thioacetate heated for 2.5 h at 100° C. Evaporation and flash-chromatography on silica gel (toluene/$CH_3CN$ 95:5) gave 0.745 g (89%) of (2R,4S)-4-acetylsulfanyl-2-(2,4,5-trifluoro-benzyloxymethyl)-pyrrolidine-1-carboxylic acid tert-butyl ester, MS: 420 ($MH^+$).

Example 14.c
Deprotection of Thioacetate

A solution of 0.126 g (0.3 mmol) (2R,4S)-4-acetylsulfanyl-2-(2,4,5-trifluoro-benzyloxymethyl)-pyrrolidine-1-carboxylic acid tert-butyl ester in 12 ml EtOH (degased with Ar) was treated at 0° C. with 0.9 ml 1N LiOH, warmed up to room temperature and stirred for 4.5 h. The reaction was recooled to 0° C. and quenched with aqueous 10% $KHSO_4$. The reaction was extracted with aqueous 10% $KHSO_4$/EtOAc (3×) and the organic phase was washed with aqueous 10% NaCl, dried over $Na_2SO_4$ and evaporated to give 0.11 g (97%) (2S,4R)-4-mercapto-2-(2,4,5-trifluoro-benzyloxymethyl)-pyrrolidine-1-carboxylic acid tert-butyl ester, MS: 378 ($MH^+$).

Example 14.d
Ether, Sulfonamides (See Table 5 and Table 6)

General procedure for the synthesis of sulfonamides: A solution of 0.32 mmol (2S,4R)-2-benzyloxymethyl-4-tritylsulfanyl-pyrrolidine or (2S,4R)-2-(2,4,5-trifluoro-benzyloxymethyl)-4-tritylsulfanyl-pyrrolidine, 65 µl (0.38 mmol) diisopropylethylamine and a catalytic amount of DMAP in 2 ml dichloroethane was added to 1.2 eq sulfonylchloride. After a night, the reaction was evaporated, redissolved in DMF and purified by preparative HPLC.

Trityl deprotection following Method 4 gave the free thiol.

In analogy: (2S,4R)-2-benzyloxymethyl-4-tritylsulfanyl-pyrrolidine and 2,4-dioxo-1,4-dihydro-2H-benzo[d][1,3]oxazine-6-sulfonyl chloride [Ferrini et al. Eur. Pat. Appl. No. 800220] gave (2S,4R)-6-(2-benzyloxymethyl-4-tritylsulfanyl-pyrrolidine-1-sulfonyl)-1H-benzo[d][1,3]oxazine-2,4-dione, MS: 689(M–H−), which was deprotected (following Method 3) to give (2S,4R)-6-(2-benzyloxymethyl-4-mercapto-pyrrolidine-1-sulfonyl)-1H-benzo[d][1,3]oxazine-2,4-dione, MS: 447 (M–H−).

A solution of 0.72 g (1.05 mmol) (2S,4R)-6-(2-benzyloxymethyl-4-tritylsulfanyl-pyrrolidine-1-sulfonyl)-1H-benzo[d][1,3]oxazine-2,4-dione in 40 ml $CH_2Cl_2$ was treated at room temperature with 0.42 ml (10.5 mmol) MeOH and 0.31 ml (2.09 mmol) DBU and stirred for 6 h. Flash chromatography on silica gel (Hexane/EtOAc 9:1) gave (2S,4R)-2-amino-5-[2-benzyloxymethyl-4-tritylsulfanyl-pyrrolidine-1-sulfonyl]-benzoic acid methyl ester which was deprotected (following Method 3) to give (2S,4R)-2-amino-5-[2-benzyloxymethyl-4-mercapto-pyrrolidine-1-sulfonyl]-benzoic acid methyl ester, MS: 437 ($M+H^+$).

A solution of 0.70 g (1.05 mmol) (2S,4R)-6-(2-benzyloxymethyl-4-tritylsulfanyl-pyrrolidine-1-sulfonyl)-1H-benzo[d][1,3]oxazine-2,4-dione in 30 ml dioxane was treated at 8° C. with 2.1 ml (2.09 mmol) aqueous LiOH and stirred for 16 h at room temperature. The reaction was evaporated, extracted with aqueous 10% $KHSO_4$/EtOAc (3×) and the organic phase was dried over $Na_2SO_4$ to give after evaporation and trityl deprotection (following Method 3) 96 mg mg (21%) of (2S,4R)-2-Amino-5-[2-benzyloxymethyl-4-mercapto-pyrrolidine-1-sulfonyl]-benzoic acid, MS: 423 ($M+H^+$).

In analogy to the general procedure: (2S,4R)-2-Benzyloxymethyl-4-tritylsulfanyl-pyrrolidine and alpha-bromophenylacetic acid gave a 1:1 mixture of (R)- and (S)-[(2S,4R)-1-methanesulfonyl-4-tritylsulfanyl-pyrrolidin-2-yl which was esterified with MeOH (see general method for EDCI-coupling taking DMAP instead of HOBT) to give after flash chromatography on silica gel (hexane/EtOAc) (R)- or (S)-[(2S,4R)-1-methanesulfonyl-4-tritylsulfanyl-pyrrolidin-2-ylmethoxy]-phenyl-acetic acid methyl ester, MS: 602 ($MH^+$) and (S)- or (R)-[(2S,4R)-1-methanesulfonyl-4-tritylsulfanyl-pyrrolidin-2-ylmethoxy]-phenyl-acetic acid methyl ester, MS: 602 ($MH^+$).

Trityl deprotection (following Method 3) gave: (R)- or (S)-[(2S,4R)-4-mercapto-1-methanesulfonyl-pyrrolidin-2-ylmethoxy]-phenyl-acetic acid methyl ester, MS: 359 (M) and (S)- or (R)-[(2S,4R)-4-mercapto-1-methanesulfonyl-pyrrolidin-2-ylmethoxyl]-phenyl-acetic acid methyl ester, MS: 359 (M).

By the reaction of (2S,4R)-2-benzyloxymethyl-4-tritylsulfanyl-pyrrolidine with the second educt mentioned in table 5 the following compounds were obtained:

TABLE 5

| | Name | 2. Educt | | MS |
|---|---|---|---|---|
| 1 | (2S,4R)-N-[4-(2-Benzyloxymethyl-4-mercapto-pyrrolidine-1-sulfonyl)-phenyl]-acetamide | 4-ACETAMIDOBENZENESULFONYL CHLORIDE | M+H+ | 421 |
| 2 | (3R,5S)-5-Benzyloxymethyl-1-(3-nitro-benzenesulfonyl)-pyrrolidine-3-thiol | 3-NITROBENZENESULFONYL CHLORIDE | M+Na+ | 431 |
| 3 | (3F,5S)-5-Benzyloxymethyl-1-(2-nitro-benzenesulfonyl)-pyrrolidine-3-thiol | 2-NITROBENZENESULFONYL CHLORIDE | M+H+ | 409 |
| 4 | (3R,5S)-5-Benzyloxymethyl-1-(4-methanesulfonyl-benzenesulfonyl)-pyrrolidine-3-thiol | 4-METHYLSULPHONYL-BENZENESULPHONYL CHLORIDE | M+Na+ | 464 |
| 5 | (3R,5S)-5-Benzyloxymethyl-1-(biphenyl-4-sulfonyl)-pyrrolidine-3-thiol | 4-BIPHENYLSULFONYL CHLORIDE | M+H+ | 440 |
| 6 | (3R,5S)-5-Benzyloxymethyl-1-(2-naphthalen-1-yl-ethanesulfonyl)-pyrrolidine-3-thiol | 2-(1-NAPHTHYL)ETHANESULFONYL CHLORIDE | 442 | M+H+ |
| 7 | (3R,5S)-5-Benzyloxymethyl-1-(3,5-dimethyl-isoxazole-4-sulfonyl)-pyrrolidine-3-thiol | 3,5-DIMETHYLISOXAZOLE-4-SULFONYL CHLORIDE | 383 | M+H+ |
| 8 | (3R,5S)-5-Benzyloxymethyl-1-(thiophene-2-sulfonyl)-pyrrolidine-3-thiol | THIOPHENE-2-SULFONYL CHLORIDE | 370 | M+H+ |
| 9 | (3R,5S)-1-Benzenesulfonyl-5-benzyloxymethyl-pyrrolidine-3-thiol | BENZENESULFONYL CHLORIDE | 364 | M+H+ |
| 10 | (3R,5S)-5-Benzyloxymethyl-1-(3-chloro-benzenesulfonyl)-pyrrolidine-3-thiol | 2-CHLOROBENZENESULFONYL CHLORIDE | 398 | M+H+ |
| 11 | (3R,5S)-5-Benzyloxymethyl-1-(2-phenyl-ethenesulfonyl)-pyrrolidine-3-thiol | TRANS-BETA-STYRENESULFONYL CHLORIDE | 390 | M+H+ |
| 12 | (3R,5S)-5-Benzyloxymethyl-1-(propane-2-sulfonyl)-pyrrolidine-3-thiol | ISOPROPYLSULFONYL CHLORIDE | 352 | M+Na+ |
| 13 | (3R,5S)-5-Benzyloxymethyl-1-(4-fluoro-benzenesulfonyl)-pyrrolidine-3-thiol | 4-FLUOROBENZENESULFONYL CHLORIDE | 382 | M+H+ |
| 14 | (3R,5S)-5-Benzyloxymethyl-1-(quinoline-8-sulfonyl)-pyrrolidine-3-thiol | 8-QUINOLINESULFONYL CHLORIDE | 415 | M+H+ |
| 15 | Mixture of (3R,5S)-1-methanesulfonyl-5-[(R)- and -[(S)-1-phenyl-ethoxymethyl)-pyrrolidi | (1-BROMOETHYL)BENZENE | 338 | M+Na+ |
| 16 | (2S,4R)-6-(2-Benzyloxymethyl-4-mercapto-pyrrolidine-1-sulfonyl)-1H-benzo[d][1,3]oxazine-2,4-dione | Lit [1] described | 447 | M−H− |

[1] 2,4-Dioxo-1,4-dihydro-2H-benzo[d][1,3]oxazine-6-sulfonyl chloride: Ferrini, Pier Giorgio; Rossi, Alberto; Haas, Georges. Substituted anthranilic acid amides. Eur. Pat. Appl., 40 pp. CODEN: EPXXDW. EP 8072 800220. CAN 93:71808 CAPLUS.

By the reaction of (2S,4R)-2-(2,4,5-Trifluoro-benzyloxymethyl)-4-tritylsulfanyl-pyrrolidine 66–7030 with the second educt mentioned in table 6 the following comounds were obtained:

TABLE 6

| | Name | 2. Educt | MS | |
|---|---|---|---|---|
| 1 | (3R,5S)-1-(Thiophene-2-sulfonyl)-5-(2,4,5-trifluoro-benzyloxymethyl)-pyrrolidine-3-thio | THIOPHENE-2-SULFONYL CHLORIDE | M+H+ | 424 |
| 2 | (3R,5S)-1-(2-Naphthalen-1-yl-ethanesulfonyl)-5-(2,4,5-trifluoro-benzyloxymethyl)-pyrrolidine-3-thiol | 2-(1-NAPHTHYL)ETHANESULFONYL CHLORIDE | M+H+ | 496 |
| 3 | (3R,5S)-1-(2-Phenyl-ethenesulfonyl)-5-(2,4,5-trifluoro-benzyloxymethyl)-pyrrolidine-3-t | TRANS-BETA-STYRENESULFONYL CHLORIDE | M+H+ | 444 |
| 4 | (3R,5S)-1-(Naphthalene-1-sulfonyl)-5-(2,4,5-trifluoro-benzyloxymethyl)-pyrrolidine-3-thiol | 1-NAPHTHALENESULFONYL CHLORIDE | M+H+ | 468 |
| 5 | (3R,5S)-1-(2-Phenyl-ethanesulfonyl)-5-(2,4,5-trifluoro-benzyloxymethyl)-pyrrolidine-3-t | Lit [1] | M+H+ | 446 |
| 6 | (3R,5S)-1-(3-Phenyl-propane-1-sulfonyl)-5-(2,4,5-trifluoro-benzyloxymethyl)-pyrrolidine | 3-PHENYL-PROPANE-1-SULFONYL CHLORIDE | M+H+ | 460 |
| 7 | (3R,5S)-1-Ethanesulfonyl-5-(2,4,5-trifluoro-benzyloxymethyl)-pyrrolidine-3-thiol | ETHANESULFONYL CHLORIDE | M+H+ | 370 |
| 8 | (3R,5S)-1-(Propane-1-sulfonyl)-5-(2,4,5-trifluoro-benzyloxymethyl)-pyrrolidine-3-thiol | 1-PROPANESULFONYL CHLORIDE | M+H+ | 384 |

TABLE 6-continued

| Name | 2. Educt | MS | |
|---|---|---|---|
| 9 (3R,5S)-1-(Butane-1-sulfonyl)-5-(2,4,5-trifluoro-benzyloxymethyl)-pyrrolidine-3-thiol | 1-BUTANESULFONYL CHLORIDE | M+H+ | 398 |
| 10 (3R,5S)-1-(Quinoline-8-sulfonyl)-5-(2,4,5-trifluoro-benzyloxymethyl)-pyrrolidine-3-thio | 8-QUINOLINESULFONYL CHLORIDE | M+H+ | 469 |
| 11 (2S,4R)-N-{4-[4-Mercapto-2-(2,4,5-trifluoro-benzyloxymethyl)-pyrrolidine-1-sulfonyl]-phenyl}-acetamide | 4-ACETAMIDOBENZENESULFONYL CHLORIDE | M+H+ | 475 |
| 12 (2S,4R)-2-Ethoxy-5-[4-mercapto-2-(2,4,5-trifluoro-benzyloxymethyl)-pyrrolidine-1-sulfonyl]-benzoic acid | Lit [2] | M+H+ | 506 |

[1] 2-Phenyl-ethanesulfonyl chloride: Zhong, Ziyang; Bibbs, Jeffrey A.; Yuan, Wei; Wong, Chi Huey. Active-site-directed modification of subtilisin. J. Am. Chem. Soc. (1991), 113(6), 2259-63. CODEN: JACSAT; ISSN: 0002-7863. CAN 114:123036 CAPLUS.

[2] 5-Chlorosulfonyl-2-ethoxy-benzoic acid: Dunn, Peter James; Wood, Albert Shaw. Process for preparation of Sildenafil by cyclization. Eur. Pat. Appl., 18 pp. CODEN: EPXXDW. EP 812845 A1 971217. CAN 128:75412 CAPLUS.

Example 14.e
Ether: Ureas (Table 7 and Table 8)

A solution of 50 mg (0.11 mmol) amine in 0.5 ml EtOH was treated with 0.21 mmol of the appropriate isocyanate, the reaction was kept 30 min at room temperature and purified by preparative HPLC (RP18, $CH_3CN/H_2O$ 80:20 to 95:5). Trityl deprotection following Method 4 gave the free thiol.

A solution of 0.02 ml (0.18 mmol) trichloromethylchloroformate in 3 ml $CH_2Cl_2$ was treated at 0° C. with 0.04 ml (0.37 mmol) quinoline and after 15 min with 0.17 g (0.33 mmol) (2S,4R)-2-(2,4,5-trifluoro-benzyloxymethyl)-4-tritylsulfanyl-pyrrolidine in 2 ml $CH_2Cl_2$. After 2 h, the reaction was evaporated and redissolved in 15 ml $CH_2Cl_2$ and treated at 0° C. with 0.14 ml (1.65 mmol) pyrrolidine and stirred for 30 min. The reaction was extracted with aqueous 10% $KHSO_4/Et_2O$ (3x) and the organic phase was dried over $Na_2SO_4$. Evaporation and precipitation from $Et_2O$/pentane gave 121 mg (59%) (2S,4R)-Pyrrolidin-1-yl-[2-(2,4,5-trifluoro-benzyloxymethyl)-4-tritylsulfanyl-pyrrolidin-1-yl]-methanone, MS: 617 (M+H+).

Trityl deprotection (following Method 3) gave (2S,4R)-[4-mercapto-2-(2,4,5-trifluoro-benzyloxymethyl)-pyrrolidin-1-yl]-pyrrolidin-1-yl-methanone, MS: 374 (M).

By the reaction of (2S,4R)-2-benzyloxymethyl-4-tritylsulfanyl-pyrrolidine with the second educt of table 7 the following compound have been obtained:

TABLE 7

| Name | 2. Educt | MS | |
|---|---|---|---|
| 1 (2S,4R)-[(2-Benzyloxymethyl-4-mercapto-pyrrolidine-1-carbonyl)-amino]-acetic acid ethyl ester | ETHYL ISOCYANATOACETATE | M+H+ | 353 |
| 2 (2S,4R)-2-Benzyloxymethyl-4-mercapto-pyrrolidine-1-carboxylic acid phenylamide | 'PHENYL ISOCYANATE | M+H+ | 343 |
| 3 (2S,4R)-2-Benzyloxymethyl-4-mercapto-pyrrolidine-1-carboxylic acid (2-fluoro-phenyl)-amide | 2-FLUOROPHENYL ISOCYANATE | M+H+ | 361 |
| 4 (2S,4R)-2-Benzyloxymethyl-4-mercapto-pyrrolidine-1-carboxylic acid (2,4-difluoro-phenyl)-amide | 2,4-DIFLUOROPHENYL ISOCYANATE | M+H+ | 379 |
| 5 (2S,4R)-(2-Benzyloxymethyl-4-mercapto-pyrrolidine-1-carbonyl)-carbamic acid ethyl ester | 'ETHOXYCARBONYL ISOCYANAT | M+Na+ | 361 |
| 6 (2S,4R)-2-Benzyloxymethyl-4-mercapto-pyrrolidine-1-carboxylic acid (3-cyano-phenyl)-amide | 3-CYANOROPHENYL ISOCYANATE | M+H+ | 368 |
| 7 (2S,4R)-2-Benzyloxymethyl-4-mercapto-pyrrolidine-1-carboxylic acid (4-acetyl-phenyl)-amide | '4-ACETYLPHENYL ISOCYANATE | M+H+ | 385 |
| 8 1:1 Mixture of (R)- and (S)-2-[[(2S,4R)-2-benzyloxymethyl-4-mercapto-pyrrolidine-1-carbonyl)-amino]-3-phenyl-propionic acid ethyl ester | ETHYL 2-ISOCYANATO-3-PHENYLPROPIONATE | M+Na+ | 465 |
| 9 (2S,4R)-2-Benzyloxymethyl-4-mercapto-pyrrolidine-1-carboxylic acid benzylamide | 'BENZYL ISOCYANATE | M+H+ | 357 |
| 10 (2S,4R)-2-Benzyloxymethyl-4-mercapto-pyrrolidine-1-carboxylic acid (3-trifluoromethyl-phenyl)-amide | 3-TRIFLUOROPHENYL ISOCYANATE | M+H+ | 411 |
| 11 (2S,4R)-2-Benzyloxymethyl-4-mercapto-pyrrolidine-1-carboxylic acid phenethyl-amide | 'PHENETHYL ISOCYANATE | M+H+ | 371 |
| 12 (2S,4R)-2-Benzyloxymethyl-4-mercapto-pyrrolidine-1-carboxylic acid naphthalen-2-ylamide | '2-NAPHTHYL ISOCYANATE | M+H+ | 393 |

TABLE 7-continued

| Name | 2. Educt | MS | |
|---|---|---|---|
| 13 (2S,4R)-2-Benzyloxymethyl-4-mercapto-pyrrolidine-1-carboxylic acid naphthalen-1-ylamide | 1-NAPHTHYL ISOCYANATE | M+H+ | 393 |

By the reaction of (2S,4R)-2-(2,4,5-trifluoro-benzyloxymethyl)-4-tritylsulfanyl-pyrrolidine with the second educt mentioned in table 8 the following compound were obtained:

(3×) and the organic phase was dried over $Na_2SO_4$. Crystallization ($CH_2Cl_2$/MeOH/$Et_2O$) gave 205 mg (47%) (2S,4R)-2-benzyloxymethyl-4-tritylsulfanyl-pyrrolidine-1-carboxylic acid amide, MS: 509 (MH$^+$).

TABLE 8

| Name | 2. Educt | MS | |
|---|---|---|---|
| 1 (2S,4R)-4-Mercapto-2-(2,4,5-trifluoro-benzyloxymethyl)-pyrrolidine-1-carboxylic acid (2-fluoro-phenyl)-amide | 2-FLUOROPHENYL ISOCYANATE | M+H+ | 415 |
| 2 (2S,4R)-4-Mercapto-2-(2,4,5-trifluoro-benzyloxymethyl)-pyrrolidine-1-carboxylic acid naphthalen-2-ylamide | '2-NAPHTHYL ISOCYANATE | M+H+ | 447 |
| 3 (2S,4R)-4-Mercapto-2-(2,4,5-trifluoro-benzyloxymethyl)-pyrrolidine-1-carboxylic acid naphthalen-1-ylamide | 1-NAPHTHYL ISOCYANATE | M+H+ | 447 |
| 4 (2S,4R)-4-Mercapto-2-(2,4,5-trifluoro-benzyloxymethyl)-pyrrolidine-1-carboxylic acid phenethyl-amide | 'PHENETHYL ISOCYANATE | M+H+ | 425 |
| 5 (2S,4R)-[4-Mercapto-2-(2,4,5-trifluoro-benzyloxymethyl)-pyrrolidine-1-carbonyl]-carbamic acid ethyl ester | 'ETHOXYCARBONYL ISOCYANAT | M+H+ | 393 |
| 7 (2S,4R)-4-Mercapto-2-(2,4,5-trifluoro-benzyloxymethyl)-pyrrolidine-1-carboxylic acid phenylamide | 'PHENYL ISOCYANATE | M+H+ | 397 |
| 8 (2S,4R)-4-Mercapto-2-(2,4,5-trifluoro-benzyloxymethyl)-pyrrolidine-1-carboxylic acid butylamide | N-BUTYL ISOCYANATE | M+H+ | 377 |
| 6 (2S,4R)-4-Mercapto-2-(2,4,5-trifluoro-benzyloxymethyl)-pyrrolidine-1-carboxylic acid benzylamide | 'BENZYL ISOCYANATE | M+H+ | 411 |

Example 14.f

Alkylation of Ureas

A solution of the urea in DMF (20 ml/mmol) was placed in an ice bath. KOtBu (1.2 eq.) was added and stirred for 15 min. MeI (1.1 eq.) was added and stirred overnight at room temperature. If required, a further 1 eq. of KOtBu and MeI was added and stirred overnight at room temperature. Water was added and the mixture was extracted with dichloromethane. The organic phase was dried ($Na_2SO_4$), filtered and evaporated. The product was purified by chromatography ($SiO_2$, EtOAc/hexane 9:1=>hexane/EtOAc 1:1).

Benzyl-methyl: (2S,4R)-2-(2,4,5-Trifluoro-benzyloxymethyl)-4-tritylsulfanyl-pyrrolidine-1-carboxylic acid benzyl-methyl-amide; yield: 53%;

Butyl-methyl: (2S,4R)-2-(2,4,5-Trifluoro-benzyloxymethyl)-4-tritylsulfanyl-pyrrolidine-1-carboxylic acid butyl-methyl-amide; yield: 52%.

Trityl deprotection (Method 3)

Butyl-methyl: (2S,4R)-4-Mercapto-2-(2,4,5-trifluoro-benzyloxymethyl)-pyrrolidine-1-carboxylic acid butyl-methyl-amide; colorless oil; yield: 76%, MS: 391 (MH$^+$);

Benzyl-methyl: (2S,4R)-4-Mercapto-2-(2,4,5-trifluoro-benzyloxymethyl)-pyrrolidine-1-carboxylic acid benzyl-methyl-amide; colorless oil; yield: 87%, MS: 425 (MH$^+$).

A solution of 400 mg (0.86 mmol) (2S,4R)-2-benzyloxymethyl-4-tritylsulfanyl-pyrrolidine in 15 ml $CH_2Cl_2$ with 0.3 ml (2.2 mmol) trimethylsilylisocyanate and a catalytic amount of DMAP was stirred over night. The reaction was extracted with aqueous 10% $KHSO_4$/EtOAc Trityl deprotection (Method 3) (2S,4R)-2-benzyloxymethyl-4-mercapto-pyrrolidine-1-carboxylic acid amide, MS: 267 (MH$^+$).

Example 14.g

Ether, Amides (Table 9 and Table 10)

General procedure Method A: 2 equivalents of an acid (0.996 mmol) in 1.7 ml THF at –10° C. were treated with 75 µl (0.48 mmol) diisopropyl carbodiimide and a catalytic amount of DMAP and warmed up to room temperature over night. 150 mg (0.32 mmol) (2S,4R)-2-benzyloxymethyl-4-tritylsulfanyl-pyrrolidine were then added and after 5 h filtered and purified by prep HPLC (RP18, $CH_3CN/H_2O$ 80:20 to 95:5).

General procedure Method B: A solution of 0.25 mmol (2S,4R)-2-(2,4,5-trifluoro-benzyloxymethyl)-4-tritylsulfanyl-pyrrolidine and 0.375 mmol acid in 1 ml dioxane was treated with 0.375 mmol EDCI in 1 ml $CH_2Cl_2$ and a catalytic amount of DMAP and stirred at room temperature over night. After evaporation and purification by prep HPLC (RP18, $CH_3CN/H_2O$ 80:20 to 95:5) the amide was received.

Trityl deprotection following Method 4 gave the free thiol.

By the reaction of (2S,4R)-2-benzyloxymethyl-4-tritylsulfanyl-pyrrolidine with the second educt metioned in table 9 the compounds mentioned in table 9 were obtained.

By the reaction of (2S,4R)-2-(2,4,5-trifluoro-benzyloxymethyl)-4-tritylsulfanylpyrrolidine with the second educt metioned in table 10 the compounds mentioned in table 10 were obtained.

TABLE 9

| | Name | 2. Educt | | MS |
|---|---|---|---|---|
| 1 | (2S,4R)-1-(2-Benzyloxymethyl-4-mercapto-pyrrolidin-1-yl)-2-methyl-propan-1-one | ISOBUTYRIC ACID | M+H+ | 294 |
| 2 | (2S,4R)-1-(2-Benzyloxymethyl-4-mercapto-pyrrolidin-1-yl)-ethanone | ACETIC ACID | M+H+ | 266 |
| 3 | ((2S,4R)-2-Benzyloxymethyl-4-mercapto-pyrrolidin-1-yl)-phenyl-methanone | BENZOIC ACID | M+H+ | 328 |
| 4 | ((2S,4R)-2-Benzyloxymethyl-4-mercapto-pyrrolidin-1-yl)-(4-methoxy-phenyl)-methanone | P-ANISIC ACID | M+H+ | 358 |
| 5 | ((2S,4R)-2-Benzyloxymethyl-4-mercapto-pyrrolidin-1-yl)-(3-bromo-phenyl)-methanone | 3-BROMOBENZOIC ACID | M+H+, 1Br | 406 |
| 6 | (2S,4R)-(2-Benzyloxymethyl-4-mercapto-pyrrolidin-1-yl)-(2,4-difluoro-phenyl)-methanone | 2,4-DIFLUOROBENZOIC ACID | M+H+ | 364 |
| 7 | (2S,4R)-(2-Benzyloxymethyl-4-mercapto-pyrrolidin-1-yl)-biphenyl-4-yl-methanone | 4-BIPHENYLCARBOXYLIC ACID | M+H+ | 404 |
| 8 | (2S,4R)-(2-Benzyloxymethyl-4-mercapto-pyrrolidin-1-yl)-(4-bromo-phenyl)-methanone | 4-BROMOBENZOIC ACID | M+H+, 1Br | 406 |
| 9 | (2S,4R)-(2-Benzyloxymethyl-4-mercapto-pyrrolidin-1-yl)-(2,4-dimethoxy-phenyl)-methanone | 2,4-DIMETHOXYBENZOIC ACID | M+H+ | 388 |
| 10 | (2S,4R)-1-(2-Benzyloxymethyl-4-mercapto-pyrrolidin-1-yl)-2-biphenyl-4-yl-ethanone | 4-BIPHENYLACETIC ACID | M+H+ | 418 |

TABLE 10

| | Name | 2. Educt | Method | MS | |
|---|---|---|---|---|---|
| 1. | (2S,4R)-[4-Mercapto-2-(2,4,5-trifluoro-benzyloxymethyl)-pyrrolidin-1-yl]-phenyl-methanone | BENZOIC ACID | B | M+H+ | 382 |
| 2. | (2S,4R)-1-[4-Mercapto-2-(2,4,5-trifluoro-benzyloxymethyl)-pyrrolidin-1-yl]-2-phenyl-ethanone | PHENYLACETIC ACID | B | M+H+ | 396 |
| 3. | (2S,4R)-Biphenyl-4-yl-[4-mercapto-2-(2,4,5-trifluoro-benzyloxymethyl)-pyrrolidin-1-yl]-methanone | 4-BIPHENYL-CARBOXYLIC ACID | B | M+H+ | 458 |
| 4. | (2S,4R)-2-Biphenyl-4-yl-1-[4-mercapto-2-(2,4,5-trifluoro-benzyloxymethyl)-pyrrolidin-1- | 4-BIPHENYLACETIC ACID | B | M+H+ | 472 |
| 5. | (2S,4R)-2-(1H-Indol-3-yl)-1-[4-mercapto-2-(2,4,5-trifluoro-benzyloxymethyl)-pyrrolidin-1-yl]-ethanone | INDOLE-3-ACETIC ACID | B | M+H+ | 435 |
| 6. | (2S,4R)-(1H-Indol-2-yl)-[4-mercapto-2-(2,4,5-trifluoro-benzyloxymethyl)-pyrrolidin-1-yl]-methanone | INDOLE-2-CARBOXYLIC ACID | B | M+H+ | 421 |
| 7. | (2S,4R)-(1H-Indol-3-yl)-[4-mercapto-2-(2,4,5-trifluoro-benzyloxymethyl)-pyrrolidin-1-yl]-methanone | INDOLE-3-CARBOXYLIC ACID | B | M+H+ | 421 |
| 8. | (2S,4R)-(1H-Indol-5-yl)-[4-mercapto-2-(2,4,5-trifluoro-benzyloxymethyl)-pyrrolidin-1-yl]-methanone | INDOLE-5-CARBOXYLIC ACID | B | M+H+ | 421 |
| 9. | (2S,4R)-(1H-Indol-6-yl)-[4-mercapto-2-(2,4,5-trifluoro-benzyloxymethyl)-pyrrolidin-1-yl]-methanone | INDOLE-6-CARBOXYLIC ACID | B | M+H+ | 421 |
| 10. | (2S,4R)-(1H-Indol-7-yl)-[4-mercapto-2-(2,4,5-trifluoro-benzyloxymethyl)-pyrrolidin-1-yl]-methanone | INDOLE-7-CARBOXYLIC ACID | B | M+H+ | 421 |
| 11. | Mixture of (R)- and (S)-N-[1-(1H-Indol-3-ylmethyl)-2-[(2S,4R)-4-mercapto-2-(2,4,5-trifl | N-ACETYL-DL-TRYPHOPHAN | B | M+H+ | 506 |
| 12. | (2S,4R)-3-(1H-Indol-3-yl)-1-[4-mercapto-2-(2,4,5-trifluoro-benzyloxymethyl)-pyrrolidin-1-yl]-propan-1-one | 3-INDOLEPROPIONIC ACID | B | M+H+ | 449 |
| 13. | (2S,4R)-4-(1H-Indol-3-yl)-1-[4-mercapto-2-(2,4,5-trifluoro-benzyloxymethyl)-pyrrolidin-1-yl]-buthan-1-one | 3-INDOLEBUTYRIC ACID | B | M+H+ | 463 |
| 14. | (2S,4R)-3-Indol-1-yl-1-[4-mercapto-2-(2,4,5-trifluoro-benzyloxymethyl)-pyrrolidin-1-yl]-propan-1-one | BETA-N-INDOLEPROPIONIC ACID | B | M+H+ | 449 |
| 15. | (1S)-N-[1-[(2S,4R)-4-Mercapto-2-(2,4,5-trifluoro-benzyloxymethyl)-pyrrolidine-1-carbonyl]-3-methyl-butyl]-acetamide | N-ACETYL-L-LEUCINE | B | M+H+ | 433 |
| 16. | (2S,4R)-1-[4-Mercapto-2-(2,4,5-trifluoro-benzyloxymethyl)-pyrrolidin-1-yl]-3-methyl-butan-1-one | 3-methyl-1-butanoic acid | B | M+H+ | 362 |
| 17. | (2S,4R)-1-[4-Mercapto-2-(2,4,5-trifluoro-benzyloxymethyl)-pyrrolidin-1-yl]-4-methyl-pentan-1-one | 4-methyl-1-pentanoic acid | B | M+H+ | 376 |

TABLE 10-continued

| Name | 2. Educt | Method | MS | |
|---|---|---|---|---|
| 18. (2S,4R)-1-[4-Mercapto-2-(2,4,5-trifluoro-benzyloxymethyl)-pyrrolidin-1-yl]-butan-1-one | 1-butanoic acid | B | M+H+ | 348 |
| 19. (2S,4R)-1-[4-Mercapto-2-(2,4,5-trifluoro-benzyloxymethyl)-pyrrolidin-1-yl]-5-methyl-hexan-1-one | 5-methyl-1-hexanoic acid | B | M+H+ | 390 |
| 20. (2S,4R)-1-[4-Mercapto-2-(2,4,5-trifluoro-benzyloxymethyl)-pyrrolidin-1-yl]-hexan-1-one | 1-hexanoic acid | B | M+H+ | 376 |
| 21. (2-Hydroxy-phenyl)-[(2S,4R)-4-mercapto-2-(2,4,5-trifluoro-benzyloxymethyl)-pyrrolidin-1-yl]-methanone | SALICYLIC ACID | B | M+H+ | 398 |
| 22. 1-[(2S,4R)-4-Mercapto-2-(2,4,5-trifluoro-benzyloxymethyl)-pyrrolidin-1-yl]-ethanone | ACETIC ACID | B | M+H+ | 320 |

Example 14.h
Ether, Sulfamides

Sulfamides, Method A: $SO_2NH_2$: A solution of 567 mg (1.09 mmol) (2S,4R)-2-(2,4,5-trifluoro-benzyloxymethyl)-4-tritylsulfanyl-pyrrolidine, 302 mg (1.09 mmol) sulfamic acid 2,4,6-trichloro-phenyl ester [Hedayatullah, M. & Hugueny, J. Phosphorus, Sulfur Silicon Relat. Elem. (1991), 61(1–2), 19–25.] and 0.15 ml triethylamine in 2 ml $CH_2Cl_2$ was heated for 1 h at reflux, evaporated and purified by flash column chromatography on silica gel with hexane/EtOAc (9:1 to 1:1) to give 286 mg (44%) (2S,4R)-2-(2,4,5-Trifluoro-benzyloxymethyl)-4-tritylsulfanyl-pyrrolidine-1-sulfonic acid amide. [Hedayatullah, M. & Hugueny, J. Phosphorus Sulfur (1985), 25(1), 33-8.] MS: 621 (M+Na$^+$).

Trityl deprotection (Method 3) (2S,4R)-4-mercapto-2-(2,4,5-trifluoro-benzyloxymethyl)-pyrrolidine-1-sulfonic acid amide, MS: 355 (M–H)$^-$.

In analogy: (2S,4R)-2-Benzyloxymethyl-4-tritylsulfanyl-pyrrolidine, gave (2S,4R)-2-benzyloxymethyl-4-mercapto-pyrrolidine-1-sulfonic acid amide, MS: 303 (M+H).

Sulfamide, Method B: $SO_2NHR$ (via $NSO_2Cl$) Following a procedure described in U.S. Pat. No. 4,868,308: 2.12 ml (21.5 mmol) Alpha-picoline and 0.19 ml (2.8 mmol) chloro sulfonic acid were added at –10° C. to 30 ml 1,2-dimethoxyethane, warmed up to 10° C. and treated with 431 mg (0.93 mmol) of (2S,4R)-2-benzyloxymethyl-4-tritylsulfanyl-pyrrolidine. The reaction was stirred at room temperature over night, treated with 0.32 ml (3.5 mmol) $POCl_3$ and after 4 h at room temperature with 5 ml 8.03 M $MeNH_2$ in EtOH. The reaction was stirred over night and extracted with aqueous 10% $KHSO_4$/EtOAc (3×), the organic phases were washed with 10% NaCl. The crude product was crystallized from $CH_2Cl_2$/$Et_2O$ at –20° C. to give 147 mg (28%) of (2S,4R)-2-benzyloxymethyl-4-tritylsulfanyl-pyrrolidine-1-sulfonic acid methylamide, mp 140–142° C., MS: 581 (M+Na$^+$).

Trityl deprotection (Method 3) gave (2S,4R)-2-benzyloxymethyl-4-mercapto-pyrrolidine-1-sulfonic acid methylamide, MS: 315 (M–H)$^-$.

Sulfamide, Method C
Preparation of Sulfamoyl Chlorides
Method C1

The amine (3 eq.) was dissolved in $CH_2Cl_2$ (1 ml/mmol) and placed in an ice bath. A solution of chlorosulfonic acid (1 eq.) in $CH_2Cl_2$ (0.5 ml/mmol) was added slowly (30 min). The reaction mixture was stirred at 0° C. for a further 30 min. Afterward, the ice bath was removed and the stirring was continued for 1 h at room temperature. The precipitate was collected by filtration and dried under high vacuum. This salt was suspended in toluene (1 ml/mmol amine) and $PCd_5$ (1 eq) was added. The mixture was stirred at 75° C. for 2 h, cooled to room temperature and filtered. The solid residue was washed with toluene. The filtrate was evaporated and dried under high vacuum. The crude sulfamoyl chloride was used in the next step without further purification.

Benzylsulfamoyl chloride (75%)
Phenylsulfamoyl chloride (72%)
Butylsulfamoyl chloride (45%)
Phenethylsulfamoyl chloride (52%)
2-Phenoxyethylsulfamoyl chloride (20%)
Cyclohexylmethylsulfamoyl chloride (74%)
Cyclopropylmethylsulfamoyl chloride (100%)
Cyclopropylsulfamoyl chloride (82%)
2,2,2-Trifluoroethylsulfamoyl chloride (74%)
4-Fluoro-benzylsulfamoyl chloride (39%)

Method C2

The amine hydrochloride (1 eq.) was dissolved in $CH_3CN$ and placed in an ice bath. Sulfuryl chloride (3 eq.) was added slowly (20 min). The reaction mixture was stirred at room temperature for 15 min and at 65° C. for 20 h. The solvent was evaporated and the residue was dried under high vacuum. The crude sulfamoyl chloride was used in the next step without further purification.

3-Chlorosulfonylamino-propionic acid ethyl ester
4-(Chlorosulfonylamino-methyl)-benzoic acid methyl ester Preparation of sulfamides: (2S,4R)-2-(2,4,5-Trifluoro-benzyloxymethyl)-4-tritylsulfanyl-pyrrolidine (1 eq) was dissolved in $CH_2Cl_2$ (2 ml/mmol) and placed in an ice bath. Diisopropylethyl amine (1.4 eq) was added and stirred for 5 min. A solution of the crude sulfamoyl chloride (1.4 eq) in $CH_2Cl_2$ (1 ml/mmol) was added. The ice bath was removed and the stirring was continued at RTovernight. A aqueous saturated solution of $KHSO_4$ was added and extracted with EtOAc. The organic phase was washed with water, dried over $Na_2SO_4$ and evaporated. The product was purified by chromatography ($SiO_2$, hexane=>hexane/EtOAc 70:30).

Benzyl: (2S,4R)-2-(2,4,5-Trifluoro-benzyloxymethyl)-4-tritylsulfanyl-pyrrolidine-1-sulfonic acid benzylamide; yield: 75%, MS: 687 (M–H)$^-$;

Phenyl: (2S,4R)-2-(2,4,5-Trifluoro-benzyloxymethyl)-4-tritylsulfanyl-pyrrolidine-1-sulfonic acid phenylamide; yield: 72%;

Butyl: (2S,4R)-2-(2,4,5-Trifluoro-benzyloxymethyl)-4-tritylsulfanyl-pyrrolidine-1-sulfonic acid butylamide; yield: 45%, MS: 653 (M–H)⁻;

Phenethyl: (2S,4R)-2-(2,4,5-Trifluoro-benzyloxymethyl)-4-tritylsulfanyl-pyrrolidine-1-sulfonic acid phenethylamide; yield: 52%;

Phenoxyethyl: (2S,4R)-2-(2,4,5-Trifluoro-benzyloxymethyl)-4-tritylsulfanyl-pyrrolidine-1-sulfonic acid (2-phenoxy-ethyl)-amide; yield: 20%, MS: 717 (M–H)⁻;

Cyclohexylmethyl: (2S,4R)-2-(2,4,5-Trifluoro-benzyloxymethyl)-4-tritylsulfanyl-pyrrolidine-1-sulfonic acid cyclohexylmethyl-amide; yield: 74%, MS: 694 (M–H)⁻;

Cyclopropylmethyl: (2S,4R)-2-(2,4,5-Trifluoro-benzyloxymethyl)-4-tritylsulfanyl-pyrrolidine-1-sulfonic acid cyclopropylmethyl-amide; yield: quant., MS: 651 (M–H)⁻;

Cyclopropyl: (2S,4R)-2-(2,4,5-Trifluoro-benzyloxymethyl)-4-tritylsulfanyl-pyrrolidine-1-sulfonic acid cyclopropyl-amide; yield: 82%, MS: 637 (M–H)⁻;

2,2,2-Trifluoro-ethyl: (2S,4R)-2-(2,4,5-Trifluoro-benzyloxymethyl)-4-tritylsulfanyl-pyrrolidine-1-sulfonic acid (2,2,2-trifluoro-ethyl)-amide; yield: 78%, MS: 679 (M–H)⁻;

4-Fluoro-benzyl: (2S,4R)-2-(2,4,5-Trifluoro-benzyloxymethyl)-4-tritylsulfanyl-pyrrolidine-1-sulfonic acid 4-fluoro-benzylamide; yield: 39%, MS: 705 (M–H)⁻;

Acetic acid ethyl ester: (2S,4R)-[2-(2,4,5-Trifluoro-benzyloxymethyl)-4-tritylsulfanyl-pyrrolidine-1-sulfonylamino]-acetic acid ethyl ester; yield: 85%, MS: 682 (M–H)⁻;

4-Methoxycarbonyl-benzyl: (2S,4R)-[4-{[2-(2,4,5-Trifluoro-benzyloxymethyl)-4-tritylsulfanyl-pyrrolidine-1-sulfonylamino]-methyl}-benzoic acid methyl ester; yield: 63%;

Dimethyl: (2S,4R)-2-Benzyloxymethyl-4-tritylsulfanyl-pyrrolidine and dimethylsulphamoyl chloride gave (2S,4R)-2-Benzyloxymethyl-4-tritylsulfanyl-pyrrolidine-1-sulfonic acid dimethylamide, MS: 573 (MH⁺).

Example 14.i
Ether, Alkylation of Sulfamides

A solution of the sulfamide in DMF (20 ml/mmol) was placed in an ice bath. NaH (55% in mineral oil, 1.2 eq.) was added and stirred for 30 min. The alkylating agent (MeI or t-butylbromoacetate, 1.2 eq.) was added and stirred overnight at room temperature. A aqueous saturated solution of NH₄Cl was added and the mixture was extracted with dichloromethane. The organic phase was dried (Na₂SO₄), filtered and evaporated. The product was purified by chromatography (SiO₂, EtOAc/hexane 95:5=>hexane/EtOAc 70:30.

Benzyl-methyl: (2S,4R)-2-(2,4,5-Trifluoro-benzyloxymethyl)-4-tritylsulfanyl-pyrrolidine-1-sulfonic acid benzyl-methyl-amide; yield: 36%, MS: 703 (M+H)⁺;

Methyl-phenyl: (2S,4R)-2-(2,4,5-Trifluoro-benzyloxymethyl)-4-tritylsulfanyl-pyrrolidine-1-sulfonic acid methyl-phenyl-amide; yield: 84%;

Benzyl-acetic acid t-butyl ester: {Benzyl-[2-(2,4,5-trifluoro-benzyloxymethyl)-4-tritylsulfahyl-pyrrolidine-1-sulfonyl]-amino}-acetic acid-tert-butyl ester; yield: 77%;

Deprotection (Method 3): Triethylsilane (10 eq.) was added to a solution of the trityl-protected thiol (1 eq.) in trifluoroacetic acid (200 eq.) at 0° C. The reaction mixture was stirred for 30 min at 0° C. The solvent was evaporated under vacuum at 0° C. The product was purified by chromatography (SiO₂, CH₂Cl₂=>CH₂Cl₂/MeOH 9:1).

Benzyl: (2S,4R)-4-Mercapto-2-(2,4,5-trifluoro-benzyloxymethyl)-pyrrolidine-1-sulfonic acid benzylamide; colorless oil; yield: 85%, MS: 445 (M–H)⁻;

Phenyl: (2S,4R)-4-Mercapto-2-(2,4,5-trifluoro-benzyloxymethyl)-pyrrolidine-1-sulfonic acid phenylamide; yellowish oil; yield: quant., MS: 431 (M–H)⁻;

Butyl: (2S,4R)-4-Mercapto-2-(2,4,5-trifluoro-benzyloxymethyl)-pyrrolidine-1-sulfonic acid butylamide; colorless solid; yield: 69%, MS: 411 (M–H)⁻;

Phenethyl: (2S,4R)-4-Mercapto-2-(2,4,5-trifluoro-benzyloxymethyl)-pyrrolidine-1-sulfonic acid phenethylamide; colorless oil; yield: 53%, MS: 459 (M–H)⁻;

Phenoxyethyl: (2S,4R)-4-Mercapto-2-(2,4,5-trifluoro-benzyloxymethyl)-pyrrolidine-1-sulfonic acid (2-phenoxy-ethyl)-amide; colorless oil; yield: quant., MS: 475 (M–H)⁻;

Cyclohexylmethyl: (2S,4R)-4-Mercapto-2-(2,4,5-trifluoro-benzyloxymethyl)-pyrrolidine-1-sulfonic acid cyclohexylmethyl-amide; colorless solid; yield: 87%, MS: 451 (M–H)⁻;

Cyclopropylmethyl: (2S,4R)-4-Mercapto-2-(2,4,5-trifluoro-benzyloxymethyl)-pyrrolidine-1-sulfonic acid cyclopropylmethyl-amide; colorless solid; yield: 94%, MS: 409 (M–H)⁻;

Cyclopropyl: (2S,4R)-4-Mercapto-2-(2,4,5-trifluoro-benzyloxymethyl)-pyrrolidine-1-sulfonic acid cyclopropyl-amide; colorless oil; yield: 75%, MS: 395 (M—H)⁻;

2,2,2-Trifluoro-ethyl: (2S,4R)-4-Mercapto-2-(2,4,5-trifluoro-benzyloxymethyl)-pyrrolidine-1-sulfonic acid (2,2,2-trifluoro-ethyl)-amide; colorless oil; yield: 88%, MS: 437 (M–H)⁻;

4-Fluoro-benzyl: (2S,4R)-4-Mercapto-2-(2,4,5-trifluoro-benzyloxymethyl)-pyrrolidine-1-sulfonic acid 4-fluoro-benzylamide; colorless oil; yield: 86%, MS: 463 (M–H)⁻;

Benzyl-methyl: (2S,4R)-4-Mercapto-2-(2,4,5-trifluoro-benzyloxymethyl)-pyrrolidine-1-sulfonic acid benzyl-methyl-amide; colorless oil; yield: 87%, MS: 425 (M+H)⁺;

Methyl-phenyl: (2S,4R)-4-Mercapto-2-(2,4,5-trifluoro-benzyloxymethyl)-pyrrolidine-1-sulfonic acid methyl-phenyl-amide; light green oil; yield: 86%, MS: 447 (M+H)⁺;

Benzyl-acetic acid: {Benzyl-[4-mercapto-2-(2,4,5-trifluoro-benzyloxymethyl)-pyrrolidine-1-sulfonyl]-amino}-acetic acid; colorless oil; yield: 88%, MS: 503 (M–H)⁻;

Acetic acid ethyl ester: (2S,4R)-[4-Mercapto-2-(2,4,5-trifluoro-benzyloxymethyl)-pyrrolidine-1-sulfonylamino]-acetic acid ethyl ester; colorless oil; yield: 96%, MS: 443 (M+H)⁺;

4-Methoxycarbonyl-benzyl: (2S,4R)-4-{[4-Mercapto-2-(2,4,5-trifluoro-benzyloxymethyl)-pyrrolid-1-sulfonylamino]-methyl}-benzoic acid methyl ester; colorless oil; yield: 70%, MS: 503 (M–H)⁻;

Dimethyl: (2S,4R)-2-Benzyloxymethyl-4-tritylsulfanyl-pyrrolidine-1-sulfonic acid dimethylamide gave, MS: 331 (MH⁺);

(2S,4R)-2-(2,4,5-Trifluoro-benzyloxymethyl)-4-tritylsulfanyl-pyrrolidine gave over two steps (2S,4R)-4-

Mercapto-2-(2,4,5-trifluoro-benzyloxymethyl)-pyrrolidine-1-sulfonic acid dimethylamide, MS: 385 (MH$^+$).

Example 14.k
Ether, Sulfonic Acid

A solution of 2-benzyloxymethyl-4-tritylsulfanyl-pyrrolidine (0.435 g) in dichloromethane (30.0 ml) was treated with 2-picoline (2.11 ml) and chlorosulphonic acid (0.186 ml). The reaction mixture was stirred for 5 h at room temperature and evaporated to dryness. The residue was quenched with ice/water and extracted with EtOAc. The aqueous layer was saturated with sodium chloride and acidified with 1 molar HCl to pH 3.4 and extracted again with EtOAc. The organic phase was washed with brine, dried over magnesium sulphate and concentrated to obtain (2S,4R)-2-benzyloxymethyl-4-tritylsulfanyl-pyrrolidine-1-sulfonic acid (0.26 g) as an oil, MS: 544 (M–H)$^-$.

To a solution of (2S,4R)-2-benzyloxymethyl-4-tritylsulfanyl-pyrrolidine-1-sulfonic acid (0.24 g) in dichloromethane (2.0 ml) was added triethylsilane (0.51 g) and trifluoroacetic acid (8.0 ml) at –10° C. The reaction mixture was stirred at –5° C. for 0.5 h and concentrated without heating. The residue was treated with water, acidified to pH 3–4 with HCl, and extracted with EtOAc. The organic phase was washed with brine, dried over magnesium sulphate and evaporated to dryness without heating. The residue was dissolved in a solution of water (3 ml) and sodium acetate (0.165 g) and chromatographed on MCI using water/methanol 1:1 as eluent to obtain 2-benzyloxymethyl-4-mercapto-pyrrolidine-1-sulfonic acid sodium salt (0.105 g) as a colourless powder after lyophillisation, MS: 302 (M–H)$^-$.

Example 15
Synthesis of C-Analogues (2R,4R)-4-(4-Methoxy-benzylsulfanyl)-2-(2-methoxycarbonyl-ethyl)-pyrrolidine-1-carboxylic acid tert-butyl ester gave after hydrolysis (General method for hydrolysis of an ester) and Weinreb-amide formation (General method for EDCI-coupling) (2R,4R)-4-(4-methoxy-benzylsulfanyl)-2-[2-(methoxy-methyl-carbamoyl)-ethyl]-pyrrolidine-1-carboxylic acid tert-butyl ester, MS: 439 (MH$^+$).

A solution of 200 mg (0.456 mmol) (2R,4R)-4-(4-Methoxy-benzylsulfanyl)-2-[2-(methoxy-methyl-carbamoyl)-ethyl]-pyrrolidine-1-carboxylic acid tert-butyl ester in 3 ml THF was treated at 0° C. with 1.14 ml (1.14 mmol, 1M THF solution) of a 4-fluorophenyl-magnesium bromide solution and after 10 min warmed up to room temperature. The reaction was partitioned between aqueous aqueous 10% KHSO$_4$/t-butyl methyl ether (3×). The organic phases were washed with aqueous 10% NaHCO$_3$ and saturated NaCl solution, dried over MgSO$_4$ and evaporated to give 144 mg (68%) of (2R,4R)-2-[3-(4-fluoro-phenyl)-3-oxo-propyl]-4-(4-methoxy-benzylsulfanyl)-pyrrolidine-1-carboxylic acid tert-butyl ester, MS: 474 (MH$^+$).

A solution of 0.539 g (1.14 mmol) (2R,4R)-2-[3-(4-Fluoro-phenyl)-3-oxo-propyl]4-(4-methoxy-benzylsulfanyl)-pyrrolidine-1-carboxylic acid tert-butyl ester in 10 ml CH$_2$Cl$_2$ was treated at 0° C. with 0.43 ml TFA. After 30 min the reaction was warmed up to room temperature (2 h) and evaporated to give (2R,4R)-1-(4-fluoro-phenyl)-3-[4-(4-methoxy-benzylsulfanyl)-pyrrolidin-2-yl]-propan-1-one; compound with trifluoro-acetic acid, MS: 374 (MH$^+$).

The crude mixture was dissolved in 20 ml CH$_2$Cl$_2$ and treated with 0.68 ml (6.2 mmol) N-methylmorpholine and 0.24 ml (1.86 mmol) n-butyl chloroformate. The reaction was stirred over night and partitioned between aqueous aqueous 10% KHSO$_4$/CH$_2$Cl$_2$ (3×). The organic phases were washed with aqueous 10% NaHCO$_3$ and saturated NaCl solution, dried over MgSO$_4$ and evaporated to give 72 mg (12%) (2R,4R)-2-[3-(4-fluoro-phenyl)-3-oxo-propyl]-4-(4-methoxy-benzylsulfanyl)-pyrrolidine-1-carboxylic acid butyl ester, MS: 474 (MH$^+$) and 36 mg (6%) (2R,4R)-1-(4-fluoro-phenyl)-3-[4-(4-methoxy-benzylsulfanyl)-1-trifluoroacetyl-pyrrolidin-2-yl]-propan-1-one, MS: 470 (MH$^+$).

In analogy: (2R,4R)-4-(4-Methoxy-benzylsulfanyl)-2-[2-(methoxy-methyl-carbamoyl)-ethyl]-pyrrolidine-1-carboxylic acid tert-butyl ester was:

1. TFA deprotected (see above) to give (2R,4R)-N-methoxy-3-[4-(4-methoxy-benzylsulfanyl)-pyrrolidin-2-yl]-N-methyl-propionamide; compound with trifluoro-acetic acid, MS: 339 (MH$^+$);

2. Sulfonylated (see above) with methanesulfonyl chloride to give (2R,4R)-3-[1-methanesulfonyl-4-(4-methoxy-benzylsulfanyl)-pyrrolidin-2-yl]-N-methoxy-N-methyl-propionamide, MS: 417 (MH$^+$) and with 2-naphthylsulfonyl chloride (2R,4R)-N-methoxy-3-[4-(4-methoxy-benzylsulfanyl)-1-(naphthalene-2-sulfonyl)-pyrrolidin-2-yl]-N-methyl-propionamide, MS: 529 (MH$^+$);

3. Reacted with a 1M THF solution of 4-fluorophenylmagnesium bromide (see above) to give (2R,4R)-1-(4-fluoro-phenyl)-3-[1-methanesulfonyl-4-(4-methoxy-benzylsulfanyl)-pyrrolidin-2-yl]-propan-1-one, MS: 452 (MH$^+$) and (2R,4R)-1-(4-fluoro-phenyl)-3-[4-(4-methoxy-benzylsulfanyl)-1-(naphthalene-2-sulfonyl)-pyrrolidin-2-yl]-propan-1-one, MS: 564 (MH$^+$).

A solution of 72 mg (0.152 mmol) (2R,4R)-2-[3-(4-fluoro-phenyl)-3-oxo-propyl]-4-(4-methoxy-benzylsulfanyl)-pyrrolidine-1-carboxylic acid butyl ester and 0.12 (1.4 mmol) triethylsilane in 2.7 ml TFA was heated for 18 h at 80° C. Evaporation followed by flash chromatography on silica gel (EtOAc/hexane 7:3) gave 8 mg (15%) (2R,4R)-2-[3-(4-fluoro-phenyl)-propyl]-4-mercapto-pyrrolidine-1-carboxylic acid butyl ester, MS: 340 (MH$^+$).

In analogy: (2R,4R)-1-(4-fluoro-phenyl)-3-[4-(4-methoxy-benzylsulfanyl)-1-trifluoroacetyl-pyrrolidin-2-yl]-propan-1-one gave (2R,4R)-2,2,2-trifluoro-1-{2-[3-(4-fluoro-phenyl)-propyl]-4-mercapto-pyrrolidin-1-yl}-ethanone, MS: 336 (MH$^+$).

(2R,4R)-1-(4-Fluoro-phenyl)-3-[1-methanesulfonyl-4-(4-methoxy-benzylsulfanyl)-pyrrolidin-2-yl]-propan-1-one gave (2R,4R)-5-[3-(4-fluoro-phenyl)-propyl]-1-methanesulfonyl-pyrrolidine-3-thiol, MS: 318 (MH$^+$).

(2R,4R)-1-(4-fluoro-phenyl)-3-[4-(4-methoxy-benzylsulfanyl)-1-(naphthalene-2-sulfonyl)-pyrrolidin-2-yl]-propan-1-one gave (2R,4R)-5-[3-(4-fluoro-phenyl)-propyl]-1-(naphthalene-2-sulfonyl)-pyrrolidine-3-thiol, MS: 336 (MH$^+$).

Example 16
5-Ring Ether Synthesis with the Final Introduction of Thiol Cis-Compound Tert-Butyletherification: To a solution of (2S,4R)-4-hydroxy-1-(naphthalene-2-sulfonyl)-pyrrolidine-2-carboxylic acid benzyl ester (14.8 g) in dichloromethane (140 ml) were added boron trifluoride ethyl etherate (3 ml) and isobutylene (cooled and liquefied at −30° C., 170 ml) at −30° C. The turbid reaction mixture was stirred at −20° C. for 2 h, poured onto a saturated sodium bicarbonate solution, and extracted with dichloromethane. The organic phases were washed with water, dried over magnesium sulphate and concentrated. The residue was chromatographed on silica gel using EtOAc/hexane 1:4 and 1:2 as eluents to obtain (2S,4R)-4-tert-butoxy-1-(naphthalene-2-sulfonyl)-pyrrolidine-2-carboxylic acid benzyl ester (16.4 g) as a glassy syrup, MS: 467 (M).

In analogy (6-ring): (2RS,5RS)-5-Hydroxymethyl-1-methanesulfonyl-piperidine-2-carboxylic acid methyl ester (3.85 g) gave (2RS,5RS)-5-tert-butoxymethyl-1-methanesulfonyl-piperidine-2-carboxylic acid methyl ester (4.40 g) as a syrup, MS: 250 (M-57).

LAH reduction: To a slurry of lithium aluminium hydride (0.72 g) in Et$_2$O (120 ml) was added a solution of (2S,4R)-4-tert-butoxy-1-(naphthalene-2-sulfonyl)-pyrrolidine-2-carboxylic acid benzyl ester (9.0 g) in Et$_2$O (80 ml) dropwise at −15° C. within 0.5 h. The suspension was stirred for 2 h at the same temperature, then a saturated solution of potassium-sodium tartrate (10 ml) was added dropwise. The slurry was filtered through a pad of filter aid and was washed with Et$_2$O. The combined filtrates were washed with brine, dried over magnesium sulphate and concentrated. The residue was crystallized from acetone/Et$_2$O/hexane to obtain (2S,4R)-[4-tert-butoxy-1-(naphthalene-2-sulfonyl)-pyrrolidin-2-yl]-methanol (6.1 g) as a colorless solid, mp 124–125° C.; MS 363 (M).

In analogy (6-ring): (2RS,5RS)-5-tert-Butoxymethyl-1-methanesulfonyl-piperidine-2-carboxylic acid methyl ester (4.20 g) gave (2RS,5RS)-(5-tert-butoxymethyl-1-methanesulfonyl-piperidin-2-yl)-methanol (3.67 g) as a colourless solid: mp 100–102° C., MS: 280 (MH$^+$).

R$^2$-ether formation: To a slurry of sodium hydride (60% in mineral oil, 2.75 g) in DMSO (100 ml) were added (2S,4R)-[4-tert-butoxy-1-(naphthalene-2-sulfonyl)-pyrrolidin-2-yl]-methanol (11.2 g) in portions within 0.5 h and benzyl bromide (7.2 ml) dropwise within 0.5 h at 20° C. The reaction mixture was stirred at room temperature for 1.5 h, poured onto ice/water and extracted with EtOAc. The organic phases were washed with water and brine, dried over magnesium sulphate and concentrated. The residue was crystallized from acetone/Et$_2$O/hexane to obtain (2S,4R)-2-benzyloxymethyl-4-tert-butoxy-1-(naphthalene-2-sulfonyl)-pyrrolidine (10.05 g) as a colorless solid, mp 101–103° C., MS: 454 (MH$^+$).

In analogy: (2S,4R)-[4-tert-Butoxy-1-(naphthalene-2-sulfonyl)-pyrrolidin-2-yl]-methanol (2.18 g) and 3-bromomethylbenzoic acid methyl ester gave (3S,5R)-3-[4-tert-butoxy-1-(naphthalene-2-sulfonyl)-pyrrolidin-2-ylmethoxymethyl]-benzoic acid methyl ester (2.08 g) as a colourless solid: mp 126–127° C.; MS: 480 (M-OCH$_3$).

(2S,4R)-[4-tert-Butoxy-1-(naphthalene-2-sulfonyl)-pyrrolidin-2-yl]-methanol (7.26 g) and cinnamyl bromide gave after chromatography on silica gel using EtOAc/hexane 1:3 as eluent (E)-(2S,4R)-4-tert-butoxy-1-(naphthalene-2-sulfonyl)-2-(3-phenyl-allyloxymethyl)-pyrrolidine (7.2 g) as a solid, MS: 480 (MH$^+$).

Hydrogenation: A solution of (E)-(2S,4R)-4-tert-butoxy-1-(naphthalene-2-sulfonyl)-2-(3-phenyl-allyloxymethyl)-pyrrolidine (2.3 g) in ethanol/dioxane 1:2 (75 ml) was hydrogenated in the presence of 10% palladium on charcoal (0.50 g) at 1.1 bar and room temperature for 4 h. The reaction mixture was filtered over a pad of celite and washed with ethanol. The filtrate was concentrated, and the residue was chromatographed on silica gel using EtOAc/hexane 1:4 as eluent to obtain (2S,4R)-4-tert-butoxy-1-(naphthalene-2-sulfonyl)-2-(3-phenyl-propoxymethyl)-pyrrolidine (2.16 g) as a gum, MS: 482 (MH$^+$).

Mitsunobu reaction: To a solution of (2S,4R)-[4-tert-butoxy-1-(naphthalene-2-sulfonyl)-pyrrolidin-2-yl]-methanol (1.81 g) in THF (15 ml) were added phenol (0.495 g) and triphenylphosphine (1.38 g) in one portion at room temperature and diisopropyl azodicarboxylate (1.0 ml) dropwise in 2 minutes. The reaction mixture was stirred over night at room temperature and concentrated. The residue was treated with water and extracted with EtOAc. The organic phase was washed with 1N sodium hydroxide, saturated sodium bicarbonate solution and brine, dried over magnesium sulphate and concentrated. The residue was chromatographed on silica gel using EtOAc/hexane 1:3 as eluent to obtain (3S,5R)-4-tert-butoxy-1-(naphthalene-2-sulfonyl)-2-phenoxymethyl-pyrrolidine as a colourless powder, MS: 439 (M).

(6-ring): To a solution of (2RS,5RS)-(5-tert-butoxymethyl-1-methanesulfonyl-piperidin-2-yl)-methanol (2.80 g) in dichloromethane (20 ml) and cyclohexane (30 ml) was added benzyl 2,2,2-trichloroacetimidate (3.03 g) and trifluoromethanesulphonic acid (0.2 ml). The reaction mixture was stirred 1 h at room temperature, poured onto a saturated sodium bicarbonate solution and extracted with EtOAc. The organic phase was washed with brine, dried over magnesium sulphate and concentrated. The residue was chromatographed on silica gel using EtOAc/hexane 1:3 and 1:2 as eluents to obtain (2RS,5RS)-2-benzyloxymethyl-5-tert-butoxymethyl-1-methanesulfonyl-piperidine (3,6 g) as a syrup, MS: 369 (M$^+$).

Trifluoroacetic acid (100 ml) was cooled to 0° C., then (2S,4R)-2-benzyloxymethyl-4-tert-butoxy-1-(naphthalene-2-sulfonyl)-pyrrolidine (7.0 g) was added in one portion. The reaction mixture was stirred for 3 h at the same temperature and then concentrated without heating under vacuum. The residue crystallized from Et2O/hexane to obtain (3R,5S)-5-benzyloxymethyl-1-(naphthalene-2-sulfonyl)-pyrrolidin-3-ol (5.07 g) as a colorless solid, mp 124–126° C., MS: 398 (MH$^+$).

In analogy: (3S,5R)-3-[4-tert-Butoxy-1-(naphthalene-2-sulfonyl)-pyrrolidin-2-ylmethoxymethyl]-benzoic acid methyl ester (2.00 g) gave (3S,5R)-3-[4-hydroxy-1-(naphthalene-2-sulfonyl)-pyrrolidin-2-ylmethoxymethyl]-benzoic acid methyl ester (0.98 g) as a colourless powder: MS: 456 (MH$^+$).

(2S,4R)-4-tert-Butoxy-1-(naphthalene-2-sulfonyl)-2-(3-phenyl-propoxymethyl)-pyrrolidine gave (3R,5S)-1-(naphthalene-2-sulfonyl)-5-(3-phenyl-propoxymethyl)-pyrrolidin-3-ol (1.36 g) as a foam: MS: 426 (MH$^+$).

(3S,5R)-4-tert-Butoxy-1-(naphthalene-2-sulfonyl)-2-phenoxymethyl-pyrrolidine (1.5 g) gave (3S,5R)-1-(naphthalene-2-sulfonyl)-5-phenoxymethyl-pyrrolidin-3-ol (0.82 g) as a white powder: MS: 384 (MH$^+$).

(6-ring) (2RS,5RS)-2-Benzyloxymethyl-5-tert-butoxymethyl-1-methanesulfonyl-piperidine (3.4 g) gave (3RS,6RS)-(6-benzyloxymethyl-1-methanesulfonyl-piperidin-3-yl)-methanol (1.75 g) as a colourless syrup, MS: 313 (M$^+$).

To a solution of triphenylphosphine (2.92 g) in tetrahydrofuran (30 ml) was added diisopropylazodicarboxylate (2.20 ml) within 5 minutes at 0° C. The solution was stirred for 0.5 h at 0° C., then a solution of (3R,5S)-5-benzyloxymethyl-1-(naphthalene-2-sulfonyl)-pyrrolidin-3-ol (2.2 g) and thioacetic acid (0.81 ml) in tetrahydrofurane (10 ml) were added to the suspension within 0.5 h at 0° C. Stirring was continued for 1 h at 0° C. and 1 h at room temperature. The reaction mixture was concentrated, and the residue was chromatographed on silica gel using EtOAc/hexane 1:4 and 1:3 as eluents to obtain (3S,5S)-thioacetic acid S-[5-benzyloxymethyl-1-(naphthalene-2-sulfonyl)-pyrrolidin-3-yl] ester (2.1 g) as a syrup, MS: 456 (MH$^+$).

In analogy: (3S,5R)-3-[4-Hydroxy-1-(naphthalene-2-sulfonyl)-pyrrolidin-2-ylmethoxymethyl]-benzoic acid methyl ester (0.78 g) was reacted as described above to obtain (2S,4S)-3-[4-acetylsulfanyl-1-(naphthalene-2-sulfonyl)-pyrrolidin-2-ylmethoxymethyl]-benzoic acid methyl ester (0.34 g) as a thick syrup, MS: 514 (MH$^+$).

(3R,5S)-1-(Naphthalene-2-sulfonyl)-5-(3-phenyl-propoxymethyl)-pyrrolidin-3-ol (0.48 g) gave thioacetic acid (3S,5S)-S-[1-(naphthalene-2-sulfonyl)-5-(3-phenyl-propoxymethyl)-pyrrolin-3-yl]ester (0.41 g) as a syrup, MS: 484 (MH$^+$). (3S,5R)-1-(naphthalene-2-sulfonyl)-5-phenoxymethyl-pyrrolidin-3-ol (0.54 g) gave (3S,5S)-thioacetic acid S-[1-(naphthalene-2-sulfonyl)-5-phenoxymethyl-pyrrolidin-3-yl]ester (0.54 g) as a glassy syrup, MS: 442 (MH$^+$).

(6-ring) (3RS,6RS)-(6-Benzyloxymethyl-1-methanesulfonyl-piperidin-3-yl)-methanol (0.94 g) gave thioacetic acid (3RS,6RS)—S-(6-benzyloxymethyl-1-methanesulfonyl-piperidin-3-ylmethyl) ester as a colorless syrup, MS: 371 (M$^+$).

S-Acetyl deprotection: To a solution of (3S,5S)-thioacetic acid S-[5-benzyloxymethyl-1-(naphthalene-2-sulfonyl)-pyrrolidin-3-yl] ester (1.2 g) in methanol (17 ml) was added sodium methanolate (28%-solution in methanol, 0.55 ml) at 0° C. The reaction mixture was stirred at 0° C. for 1.5 h, and acetic acid (0.17 ml) was added. The reaction mixture was concentrated, and the residue was extracted with EtOAc. The organic phases were washed with water, dried over magnesium sulphate and concentrated. The residue was chromatographed on silica gel using EtOAc/hexane 1:3 and 1:2 as eluents to obtain (3S,5S)-5-benzyloxymethyl-1-(naphthalene-2-sulfonyl)-pyrrolidine-3-thiol (0.59 g) as a slightly coloured syrup, MS: 414 (MH$^+$).

In analogy: (2S,4S)-3-[4-Acetylsulfanyl-1-(naphthalene-2-sulfonyl)-pyrrolidin-2-ylmethoxymethyl]-benzoic acid methyl ester (0.30 g) gave (2S,4S)-3-[4-mercapto-1-(naphthalene-2-sulfonyl)-pyrrolidin-2-ylmethoxymethyl]-benzoic acid methyl ester (0.21 g) as a colourless amorphous powder, MS: 440 (M-OCH3).

Thioacetic acid (3S,5S)—S-[1-(naphthalene-2-sulfonyl)-5-(3-phenyl-propoxymethyl)-pyrrolidin-3-yl] ester (0.33 g) gave (3S,5S)-1-(naphthalene-2-sulfonyl)-5-(3-phenyl-propoxymethyl)-pyrrolidine-3-thiol (0.23 g) as a syrup, MS: 407 (M-H$_2$S). (3S,5S)-Thioacetic acid S-[1-(naphthalene-2-sulfonyl)-5-phenoxymethyl-pyrrolidin-3-yl] ester (0.5 g) gave (3S,5S)-1-(naphthalene-2-sulfonyl)-5-phenoxymethyl-pyrrolidine-3-thiol (0.27 g) as a colourless powder, MS: 399 (M).

6-ring: Thioacetic acid (3RS,6RS)—S-(6-benzyloxymethyl-1-methanesulfonyl-piperidin-3-ylmethyl) ester (0.78 g) gave (3RS,6RS)-(6-benzyloxymethyl-1-methanesulfonyl-piperidin-3-yl)-methanethiol (0.52 g) as a syrup, MS: 329 (M$^+$).

To solution of (2S,4S)-3-[4-mercapto-1-(naphthalene-2-sulfonyl)-pyrrolidin-2-ylmethoxymethyl]-benzoic acid methyl ester (0.48 g) in methanol (14 ml) was added a 0.1 molar sodium carbonate solution (25 ml). The reaction mixture was refluxed for 5 h and concentrated. The residue was treated with 1 eq 1N HCl, water and extracted with EtOAc.

The organic phase was washed with brine, dried over magnesium sulphate and concentrated. The residue was chromatographed on silica gel using EtOAc/methanol/water 93:5:2 as eluent to obtain (2S,4S)-3-[4-mercapto-1-(naphthalene-2-sulfonyl)-pyrrolidin-2-ylmethoxymethyl]-benzoic acid (0.34 g) as a colourless thick syrup, MS: 458 (MH$^+$).

Example 17
5-Ring Ether Synthesis with the Final Introduction of Thiol Trans Compound To a suspension of methanesulphonic acid (0.96 g) in toluene (30 ml) was added triethylamine (1.40 ml) and triphenylphosphine (2.72 g) at 0–5° C. The suspension was stirred for 5 minutes, and (3R,5S)-5-benzyloxymethyl-1-(naphthalene-2-sulfonyl)-pyrrolidin-3-ol (3.46 g) dissolved in toluene (20 ml) was added dropwise in 5 minutes, followed by diisipropyl azodicarboxylate (2.0 ml). The reaction mixture was stirred for 3 h at 85° C., poured onto ice/water and extracted with ethy acetate. The organic phase was washed with 10% KHSO$_4$— and NaCl solutions, dried over magnesium sulphate and concentrated. The residue was chromatographed on silica gel using EtOAc/hexane 1:2 and 1:1 as eluents to obtain (3S,5S)-methanesulfonic acid 5-benzyloxymethyl-1-(naphthalene-2-sulfonyl)-pyrrolidin-3-yl ester (3.35 g) as a slightly yellow syrup, MS: 476 (MH$^+$).

In analogy: (3S,5R)-3-[4-Hydroxy-1-(naphthalene-2-sulfonyl)-pyrrolidin-2-ylmethoxymethyl]-benzoic acid methyl ester (1.10 g) gave (2S,4S)-3-[4-methanesulfonyloxy-1-(naphthalene-2-sulfonyl)-pyrrolidin-2-ylmethoxymethyl]-benzoic acid methyl ester (0.32 g) as a colourless solid, MS: 534 (MH$^+$).

(3R,5S)-1-(Naphthalene-2-sulfonyl)-5-(3-phenyl-propoxymethyl)-pyrrolidin-3-ol (0.88 g) gave methanesulfonic acid (3S,5S)-1-(naphthalene-2-sulfonyl)-5-(3-phenyl-propoxymethyl)-pyrrolidin-3-yl ester (0.68 g) as a foam. The compound was used in the next step without purification.

(3S,5R)-1-(Naphthalene-2-sulfonyl)-5-phenoxymethyl-pyrrolidin-3-ol (0.75 g) gave (3S,5S)-methanesulfonic acid 1-(naphthalene-2-sulfonyl)-5-phenoxymethyl-pyrrolidin-3-yl ester (0.65 g) as a syrup, MS: 462 (MH$^+$).

To a solution of (3S,5S)-methanesulfonic acid 5-benzyloxymethyl-1-(naphthalene-2-sulfonyl)-pyrrolidin-3-yl ester (3.0 g) in abs DMF (60 ml) was added potassium thioacetate (1.08 g). The reaction mixture was stirred for 1 h at 100° C. and concentrated under oil pump vacuum. The residue was treated with ice/water and extracted with EtOAc. The organic phase was washed with water and brine, dried over magnesium sulphate and concentrated. The residue was chromatographed on silica gel using EtOAc/hexane 1:3 as eluent to obtain (3S,5R)-thioacetic acid S-[5-benzyloxymethyl-1-(naphthalene-2-sulfonyl)-pyrrolidin-3-yl]ester (2.16 g) as a slightly yellow powder, MS: 334 (M−121).

In analogy: (2S,4S)-3-[4-Methanesulfonyloxy-1-(naphthalene-2-sulfonyl)-pyrrolidin-2-ylmethoxymethyl]-benzoic acid methyl ester (0.30 g) was reacted as described above to obtain (2S,4R)-3-[4-acetylsulfanyl-1-(naphthalene-2-sulfonyl)-pyrrolidin-2-ylmethoxymethyl]-benzoic acid methyl ester (0.23 g) as a thick syrup, MS: 514 (MH$^+$).

Crude methanesulfonic acid (3S,5S)-1-(naphthalene-2-sulfonyl)-5-(3-phenyl-propoxymethyl)-pyrrolidin-3-yl este (0.64 g) gave thioacetic acid (3R,5S) —S-[1-(naphthalene-2-sulfonyl)-5-(3-phenyl-propoxymethyl)-pyrrolidin-3-yl] ester (0.26 g) as a syrup, MS: 484 (MH$^+$).

(3S,5S)-Methanesulfonic acid 1-(naphthalene-2-sulfonyl)-5-phenoxymethyl-pyrrolidin-3-yl ester (0.62 gave (3R,5S)-thioacetic acid S-[1-(naphthalene-2-sulfonyl)-5-phenoxymethyl-pyrrolidin-3-yl] ester (0.52 g) as a slightly coloured powder, MS: 442 (MH$^+$).

(3S,5R)-Thioacetic acid S-[5-benzyloxymethyl-1-(naphthalene-2-sulfonyl)-pyrrolidin-3-yl] ester (1.91 g) was reacted as described above in S-Acetyl deprotection to obtain (3S,5R)-5-benzyloxymethyl-1-(naphthalene-2-sulfonyl)-pyrrolidine-3-thiol (1.15 g) as an off-white solid, mp 79–80° C., MS: 413 (M).

In analogy: (2S,4R)-3-[4-Acetylsulfanyl-1-(naphthalene-2-sulfonyl)-pyrrolidin-2-ylmethoxymethyl]-benzoic acid methyl ester (0.53 g) was reacted as described above in S-Acetyl deprotection to obtain (2S,4R)-3-[4-mercapto-1-(naphthalene-2-sulfonyl)-pyrrolidin-2-ylmethoxymethyl]-benzoic acid methyl ester (0.23 g) as a thick syrup, MS: 471 (M).

Thioacetic acid (3R,5S)—S-[i-(naphthalene-2-sulfonyl)-5-(3-phenyl-propoxymethyl)-pyrrolidin-3-yl] ester (0.20 g) was reacted as described above in S-Acetyl deprotection to obtain (3R,5S)-1-(naphthalene-2-sulfonyl)-5-(3-phenyl-propoxymethyl)-pyrrolidine-3-thiol (0.17 g) as a syrup, MS: 442 (MH$^+$).

(3R,5S)-Thioacetic acid S-[1-(naphthalene-2-sulfonyl)-5-phenoxymethyl-pyrrolidin-3-yl] ester (0.35 g) was reacted as described above in S-Acetyl deprotection to obtain (3R,5S)-1-(naphthalene-2-sulfonyl)-5-phenoxymethyl-pyrrolidine-3-thiol (0.21 g) as a thick syrup, MS: 399 (M).

6-ring: To rac-cis-Piperidine-2,5-dicarboxylic acid dimethyl ester [Frank J., J. Heterocyclic Chem. 32, 857–861 (1995)] (36.2 g) dissolved in dichloromethane (720 ml) were added 4-dimethylaminopyridine (33.0 g) and, dropwise, methanesulphonyl chloride (28.6 g) within 10 minutes and room temperature. The temperature rose to 35° C. The reaction mixture was stirred 1 h at room temperature, washed with 2 molar HCJ, sodium carbonate-solution and brine, dried over magnesium sulphate and concentrated to dryness to obtain (2RS,5RS)-1-methanesulfonyl-piperidine-2,5-dicarboxylic acid dimethyl ester (46.8 g) as a syrup, MS: 220 (M$^+$-59).

In analogy: rac-cis-Piperidine-2,5-dicarboxylic acid dimethyl ester with naphthalene-2-sulphonyl chloride gave (2RS,5RS)-1-(naphthalene-2-sulfonyl)-piperidine-2,5-dicarboxylic acid dimethyl ester (36.3 g) as a colourless solid, mp 94–96° C., MS: 392 (MH$^+$).

To a solution of a 16:9 mixture of meso- and (3RS,5RS)-piperidine-3,5-dicarboxylic acid dimethyl ester [Stetter, H. & Henning, H., Chem. Ber. 88, 789–795 (1955)] (23.0 g) in dichloromethane (460 ml) and triethylamine (30 ml) was added naphthalene-2-sulphonyl chloride (24.5 g) in dichloromethane (50 ml) in 15 minutes at room temperature. The reaction mixture was boiled under reflux for 4 h, cooled down and washed with water and sodium bicarbonate solution, dried over magnesium sulphate and concentrated. The residue was chromatographed on silica gel using EtOAc/hexane 1:3, 1:2 and 1:1 as eluents to obtain a racemic mixture of meso-1-(naphthalene-2-sulfonyl)-piperidine-3,5-dicarboxylic acid dimethyl ester (22.6 g) as a colourless solid, mp 123–125° C., MS: 360 (M$^+$-31).

To a solution of (2RS,5RS)-1-methanesulfonyl-piperidine-2,5-dicarboxylic acid dimethyl ester (46.5 g) in methanol (850 ml) and water (85 ml) was added 1 molar sodium hydroxide (166 ml) within 20 minutes at reflux temperature. The reaction mixture was stirred for 45 minutes at reflux, cooled and concentrated. The residue was taken up in water (300 ml) and washed with Et$_2$O. The aqueous phase was acidified with 1 molar HCl (166 ml) and extracted with EtOAc. The organic phase was washed with brine, dried over magnesium sulphate and concentrated. The residue was crystallized from acetone/Et$_2$O to obtain (2RS,5RS)-1-methanesulfonyl-piperidine-2,5-dicarboxylic acid 2-methyl ester (16.8 g) as a colourless solid, mp 130–133° C., MS: 206 (M$^+$-59).

In analogy: (2RS,5RS)-1-(Naphthalene-2-sulfonyl)-piperidine-2,5-dicarboxylic acid dimethyl ester (16.0 g) gave (2RS,5RS)-1-(naphthalene-2-sulfonyl)-piperidine-2,5-dicarboxylic acid 2-methyl ester (6.25 g) as a colourless solid, MS: 377 (M$^+$).

Meso-1-(naphthalene-2-sulfonyl)-piperidine-3,5-dicarboxylic acid dimethyl ester (3.0 g) gave (3RS,5SR)-1-(naphthalene-2-sulfonyl)-piperidine-3,5-dicarboxylic acid monomethyl ester (1.58 g) as a colourless amorphous powder, MS: 378 (MH$^+$).

To a solution of (2RS,5RS)-1-methanesulfonyl-piperidine-2,5-dicarboxylic acid 2-methyl ester (10.7 g) in tetrahydrofuran was added a 1 M borane solution in tetrahydrofuran (215 ml) within 0.5 h at 0° C. The reaction mixture was stirred for 4 h at 0° C., poured onto ice/saturated sodium bicarbonate solution and concentrated. The aqueous residue was extracted with EtOAc. The organic phase was washed with brine, dried over magnesium sulphate and concentrated. The residue was chromatographed on silica gel using EtOAc/hexane 1:1 and 3:2 as eluents to obtain (2RS,5RS)-5-hydroxymethyl-1-methanesulfonyl-piperidine-2-carboxylic acid methyl ester (8.1 g) as a colourless solid, MS: 206 (100%, M$^+$-59).

In analogy: (2RS,5RS)-1-(Naphthalene-2-sulfonyl)-piperidine-2,5-dicarboxylic acid 2-methyl ester (1.80 g) gave (2RS,5RS)-5-hydroxymethyl-1-(naphthalene-2-sulfonyl)-piperidine-2-carboxylic acid methyl ester (1.45 g) as a colourless foam, MS: 364 (MH$^+$).

(3RS,5SR)-1-(Naphthalene-2-sulfonyl)-piperidine-3,5-dicarboxylic acid monomethyl ester (1.50 g) gave (3SR,5RS)-5-hydroxymethyl-1-(naphthalene-2-sulfonyl)-piperidine-3-carboxylic acid methyl ester (0.86 g) as a syrup, MS: 364 (MH$^+$).

(3SR,5RS)-5-Hydroxymethyl-1-(naphthalene-2-sulfonyl)-piperidine-3-carboxylic acid methyl ester (4.8 g) was reacted as described in Example 16 (R$^2$-ether formation) to obtain (3SR,5RS)-5-benzyloxymethyl-1-(naphthalene-2-sulfonyl)-piperidine-3-carboxylic acid methyl ester (5.4 g) as a colourless gum, MS: 454 (MH$^+$).

In analogy: (2RS,5RS)-5-Hydroxymethyl-1-(naphthalene-2-sulfonyl)-piperidine-2-carboxylic acid methyl ester (1.82 g) gave (2RS,5RS)-5-benzyloxymethyl-1-(naphthalene-2-sulfonyl)-piperidine-2-carboxylic acid methyl ester (1.60 g) as a light yellow gum, MS: 454 (MH$^+$).

(2RS,5RS)-5-Hydroxymethyl-1-methanesulfonyl-piperidine-2-carboxylic acid methyl ester (3.01 g) gave (2RS,5RS)-5-benzyloxymethyl-1-methanesulfonyl-piperidine-2-carboxylic acid methyl ester (2.80 g) as a colourless gum, MS: 282 (M-59).

(3SR,5RS)-5-Benzyloxymethyl-1-(naphthalene-2-sulfonyl)-piperidine-3-carboxylic acid methyl ester (2.70 g) was reduced with lithium aluminium hydride as described in Example 17 to obtain (3SR,5RS)-[5-benzyloxymethyl-1-(naphthalene-2-sulfonyl)-piperidin-3-yl]-methanol (1.54 g) as a syrup, MS: 426 (MH$^+$).

In analogy: (2RS,5RS)-5-Benzyloxymethyl-1-(naphthalene-2-sulfonyl)-piperidine-2-carboxylic acid methyl ester (1.30 g) gave (2RS,5RS)-[5-benzyloxymethyl-1-(naphthalene-2-sulfonyl)-piperidin-2-yl]-methanol (0.67 g) as a light yellow viscous oil, MS: 426 (MH$^+$).

(2RS,5RS)-5-Benzyloxymethyl-1-methanesulfonyl-piperidine-2-carboxylic acid methyl ester (2.70 g) gave (2RS,5RS)-(5-benzyloxymethyl-1-methanesulfonyl-piperidin-2-yl)-methanol (1.70 g) as a light yellow syrup, MS: 282 (M-31).

(3SR,5RS)-[5-Benzyloxymethyl-1-(naphthalene-2-sulfonyl)-piperidin-3-yl]-methanol (1.35 g) was reacted with thioacetic acid (see Mitsunobu reaction described in Example 17) to obtain thioacetic acid (3SR,5RS)—S-[5-benzyloxymethyl-1-(naphthalene-2-sulfonyl)-piperidin-3-ylmethyl] ester (0.92 g) as a syrup, MS: 484 (MH$^+$).

In analogy: (2RS,5RS)-[5-Benzyloxymethyl-1-(naphthalene-2-sulfonyl)-piperidin-2-yl]-methanol (0.64 g) gave thioacetic acid (2RS,5RS)—S-[5-benzyloxymethyl-1-(naphthalene-2-sulfonyl)-piperidin-2-ylmethyl] ester (0.48 g) as a light yellow syrup, MS: 484 (MH$^+$).

(2RS,5RS)-(5-Benzyloxymethyl-1-methanesulfonyl-piperidin-2-yl)-methanol (1.41 g) gave thioacetic acid (2RS,5RS)—S-(5-benzyloxymethyl-1-methanesulfonyl-piperidin-2-ylmethyl) ester (0.95 g) as a light brown gum, MS: 372 (MH$^+$).

Thioacetic acid (3SR,5RS)—S-[5-benzyloxymethyl-1-(naphthalene-2-sulfonyl)-piperidin-3-ylmethyl] ester (0.88 g) gave (3SR,5RS)-[5-benzyloxymethyl-1-(naphthalene-2-sulfonyl)-piperidin-3-yl]-methanethiol (0.92 g) as a syrup, MS: 442 (MH$^+$).

In analogy: Thioacetic acid (2RS,5RS)—S-[5-benzyloxymethyl-1-(naphthalene-2-sulfonyl)-piperidin-2-ylmethyl] ester (0.34 g) gave (2RS,5RS)-5-Benzyloxymethyl-1-(naphthalene-2-sulfonyl)-piperidin-2-yl]-methanethiol (0.23 g) as a colourless syrup, MS: 442 (MH$^+$).

Thioacetic acid (2RS,5RS)—S-(5-benzyloxymethyl-1-methanesulfonyl-piperidin-2-ylmethyl) ester (0.78 g) gave (2RS,5RS)-(5-benzyloxymethyl-1-methanesulfonyl-piperidin-2-yl)-methanethiol (0.54 g) as a colourless syrup, MS: 330 (MH$^+$).

Example 18

Ethers, 3,4-Substituted Pyrrolidine-Ethers

To a solution of (3RS,4RS)-pyrrolidine-3,4-dicarboxylic acid diethyl ester (2.04 g, 9.48 mmol) [Bull. Soc. Chim. Fr. 1988, 579] in dichloromethane (30 ml) was added pyridine (1.12 g, 14.22 mmol), N,N-dimethylaminopyridine (10 mg) and methanesulfonyl chloride (1.30 g, 11.38 mmol) and stirred for 2 h at RT The solution was washed with 0.5 M aqueous HCl and water, dried and evaporated. Flash chromatography (EtOAc/hexane 1:1) gave 1.6 g (42%) of (3RS,4RS)-1-methanesulfonyl-pyrrolidine-3,4-dicarboxylic acid diethyl ester as a colorless solid, MS: 310 (M+NH$_4$)$^+$.

In analogy: (3RS,4RS)-1-(Naphthalene-2-sulfonyl)-pyrrolidine-3,4-dicarboxylic acid diethyl ester was obtained (44%) as a colorless solid, MS: 410 (MH$^+$).

To a solution of (3RS,4RS)-1-methanesulfonyl-pyrrolidine-3,4-dicarboxylic acid diethyl ester (1.13 g, 3.85 mmol) in THF (40 ml) was slowly added a 1 M solution of LiAlH$_4$ in THF (11.55 ml. 11.55 mmol) at 0° C. The mixture was stirred for 1.5 h at 0° C. Water (0.44 ml), 1 M aqueous NaOH (0.44 ml) and water (1.31 ml) were added subsequently at 0° C. MgSO$_4$ was added and filtered. The solid was washed with EtOAc (4x). The filtrate was evaporated to leave a colorless solid that was washed with hot dichloromethane to give ([3RS,4RS]-4-hydroxymethyl-1-methanesulfonyl-pyrrolidin-3-yl)-methanol as a colorless solid, MS: 268 (M+OAc)$^-$.

In analogy: (3RS,4RS)-[4-Hydroxymethyl-1-(naphthalene-2-sulfonyl)-pyrrolidin-3-yl]-methanol was obtained (74%) from (3RS,4RS)-1-(naphthalene-2-sulfonyl)-pyrrolidine-3,4-dicarboxylic acid diethyl ester as a colorless solid, MS: 321 (M)$^+$.

To a suspension of 60% NaH (66 mg, 1.64 mmol) in DMF (3 ml) was added a solution of ([3RS,4RS]-4-hydroxymethyl-1-methanesulfonyl-pyrrolidin-3-yl)-methanol (327 mg, 1.56 mmol) in DMF (5 ml) at −12° C. After 5 min, benzylbromide (286 mg, 1.64 mmol) was added and the mixture was stirred at −12° C. for 30 min. The mixture was allowed to warm to room temperature. The solvent was evaporated. Water was added and extracted with dichloromethane. The organic phase was dried, filtered and evaporated. Flash chromatography (hexane/EtOAc 2:1=>1:1) gave 275 mg (58%) of ([3RS,4RS]-4-benzyloxymethyl-1-methanesulfonyl-pyrrolidin-3-yl)-methanol as a colorless oil, MS: 358 (M+OAc)$^-$.

To a solution of ([3RS,4RS]-4-benzyloxymethyl-1-methanesulfonyl-pyrrolidin-3-yl)-methanol (267 mg, 0.89 mmol) and triethylamine (372 ml, 2.67 mmol) in Et$_2$O (4 ml)

was slowly added methanesulfonyl chloride (137 ml, 1.78 mmol) at −20° C. After 15 min the mixture was allowed to warm to room temperature 1 M aqueous HCl (0.5 ml) was added. The organic phase was washed with water, dried, filtered and evaporated to give a colorless oil (264 mg). DMF (2.5 ml) and potassium thioacetate (120 mg, 1.05 mmol) were added and the mixture was heated to 100° C. for 1 h. Dichloromethane was added and washed with water. The organic phase was dried, filtered and evaporated. Flash chromatography (EtOAc/hexane 1:1) gave 151 mg (48%) of thioacetic acid (3RS,4RS)—S-(4-benzyloxymethyl-1-methanesulfonyl-pyrrolidin-3-ylmethyl) ester as a light yellow solid, MS: 416 (M+OAc)$^-$.

To a solution of LiAlH$_4$ (0.23 mmol, 1 M in THF) in Et$_2$O (6 ml) was added a suspension of thioacetic acid (3RS, 4RS)—S-(4-benzyloxymethyl-1-methanesulfonyl-pyrrolidin-3-ylmethyl) ester (75.5 mg, 0.21 mmol) in Et$_2$O. The mixture was stirred at RT for 30 min and refluxed for 2 h. After cooling to r.t., water and 1 M aqueous HCl were added. The organic phase was dried and evaporated to give 63 mg (95%) of [(3RS,4RS)-4-benzyloxymethyl-1-methanesulfonyl-pyrrolidin-3-yl]-methanethiol as a colorless oil, MS: 333 (M+NH$_4$)$^+$.

A solution of ([3RS,4RS]-4-hydroxymethyl-1-methanesulfonyl-pyrrolidin-3-yl)-methanol (316 mg, 1.51 mmol), tosylchloride (288 mg, 1.51 mmol), N,N-dimethylaminopyridine (10 mg) and triethylamine (153 mg, 1.51 mmol) in THF (10 ml) was stirred overnight at room temperature Dichloromethane and 1 M aqueous HCl were added. The organic phase was separated. The aqueous phase was extracted with dichloromethane. The combined organic phases were washed with water, dried and evaporated to give the crude tosylate as a colorless oil.

To a solution of triphenylmethane thiol (639 mg, 2.26 mmol) in DMF (3 ml) was added KotBu (220 mg, 1.96 mmol) at 0° C. and stirred for 20 min. A solution of the crude tosylate in DMF was added and stirred for 3 h at room temperature. Water was added and the mixture was extracted with dichloromethane. The organic phase was dried, filtered and evaporated. Flash chromatography (dichloromethane=>dichloromethane/MeOH 95:5) gave 236 mg (33%) of [(3RS,4RS)-1-methanesulfonyl-4-tritylsulfanylmethyl-pyrrolidin-3-yl]-methanol as a colorless foam, MS: 526 (M+OAc)$^-$.

In analogy: (3RS,4RS)-1-l(Naphthalene-2-sulfonyl)-4-tritylsulfanylmethyl-pyrrolidin-3-yl]-methanol was obtained (55%) from (3RS,4RS)-[4-hydroxymethyl-1-(naphthalene-2-sulfonyl)-pyrrolidin-3-yl]-methanol as a colorless foam, MS: 602 (M+Na)$^+$.

To a solution of [(3RS,4RS)-1-methanesulfonyl-4-tritylsulfanylmethyl-pyrrolidin-3-yl]-methanol (106 mg, 0.226 mmol) in THF (15 ml) were added triethylamine (47 ml, 0.34 mmol) and methanesulfonyl chloride (26 ml, 0.34 mmol) at 0° C. The mixture was stirred at 0° C. for 30 min and at RTfor 1 h. Water and 1 M aqueous HCl were added and the mixture was extracted with EtOAc. The organic phase was dried, filtered and evaporated to give the crude mesylate as a colorless oil.

To a suspension of 60% NaH (14 mg, 0.339 mmol) in DMF (1 ml) was added phenol (43 mg, 0.452 mmol) and stirred for 15 min. A solution of the crude mesylate in DMF was added and the mixture was stirred for 8 h. Water was added and the mixture was extracted with dichloromethane. The organic phase was dried, filtered and evaporated. Flash chromatography (hexane/EtOAc 4:1=>1:1) gave 52 mg (43%) of (3RS,4RS)-1-methanesulfonyl-3-phenoxymethyl-4-tritylsulfanylmethyl-pyrrolidine as a colorless foam, MS: 566 (M+Na)$^+$.

In analogy: (3RS,4RS)-1-(Naphthalene-2-sulfonyl)-3-phenoxymethyl-4-tritylsulfanylmethyl-pyrrolidine was obtained (43%) from (3RS,4RS)-[1-(naphthalene-2-sulfonyl)-4-tritylsulfanylmethyl-pyrrolidin-3-yl]-methanol as a colorless oil, MS: 656 (MH$^+$).

To a solution of (3RS,4RS)-[1-(naphthalene-2-sulfonyl)-4-tritylsulfanylmethyl-pyrrolidin-3-yl]-methanol (200 mg, 0.345 mmol) in DMF (2 ml) was added 60% NaH (15.2 mg, 0.379 mmol) at 0° C. and stirred for 10 min. Benzyl bromide (45 µl, 0.379 mmol) was added and stirred for 30 min at 0° C. and for 1 h at room temperature. Water was added and the mixture was extracted with dichloromethane. The organic phase was dried, filtered and evaporated. Flash chromatography (hexane/EtOAc 4:1=>1:1) gave 140 mg (61%) of (3RS,4RS)-1-(naphthalene-2-sulfonyl)-3-benzyloxymethyl-4-tritylsulfanylmethyl-pyrrolidine as a colorless foam, MS: 692 (M+Na)$^+$.

To a solution of (3RS,4RS)-1-methanesulfonyl-3-phenoxymethyl-4-tritylsulfanyl-methyl-pyrrolidine (50 mg, 0.092 mmol) in trifluoroacetic acid (1.4 ml, 18.4 mmol) was added triethylsilane (107 mg, 0.92 mmol) at 0° C. The mixture was stirred for 30 min at 0° C. The solvent was evaporated at room temperature. Flash chromatography (dichloromethane=>dichloromethane/MeOH 98:2) gave 27 mg (97%) of [(3RS,4RS)-1-methanesulfonyl-4-phenoxymethyl-pyrrolidin-3-yl]-methanethiol as a colorless oil, MS: 301 (M)$^+$.

In analogy: (3RS,4RS)-[1-(Naphthalene-2-sulfonyl)-4-phenoxymethyl-pyrrolidin-3-yl]-methanethiol was obtained (88%) from (3RS,4RS)— 1-(naphthalene-2-sulfonyl)-3-phenoxymethyl-4-tritylsulfanylmethyl-pyrrolidine as a colorless oil, MS: 414 (MH$^+$).

(3RS,4RS)-[4-Benzyloxymethyl-1-(naphthalene-2-sulfonyl)-pyrrolidin-3-yl]-methanethiol was obtained (quant.) from (3RS,4RS)-1-(naphthalene-2-sulfonyl)-3-benzyloxymethyl-4-tritylsulfanylmethyl-pyrrolidine as a colorless oil, MS: 428 (MH$^+$).

Example 19

6-Ring Ether

A suspension of 31.15 g (150 mmol) 3-Ethoxycarbonyl-4-piperidone hydrochloride was suspended in 400 ml hexamethyldisilazane and heated under reflux (140° C.) for 2.5 h. The solution was evaporated complete, the residue dissolved in 400 ml THF and treated with 34 g (150 mmol) of naphthalene-2-sulfonylchloride in 150 ml THF. The reaction was stirred 16 h at room temperature, evaporated, treated with 400 ml aqueous 10% NaCl, stirred for 10 min and extracted with EtOAc (3×400 ml). The organic phase was dried (Na$_2$SO$_4$) and evaporated and crystallized from Et$_2$O at 5° C. to give 53.1 g (90%) of 4-hydroxy-1-(naphthalene-2-sulfonyl)-1,2,5,6-tetrahydro-pyridine-3-carboxylic acid ethyl ester, MS: 362 (MH$^+$).

In analogy: 3-Ethoxycarbonyl-4-piperidone hydrochloride and methanesulfonyl chloride gave 4-hydroxy-1- methanesulfonyl-1,2,5,6-tetrahydro-pyridine-3-carboxylic acid ethyl ester, mp 87–88° C., MS: 250 (MH$^+$).

A suspension of 28.9 g (80 mmol) 4-hydroxy-1-(naphthalene-2-sulfonyl)-1,2,5,6-tetrahydro-pyridine-3-carboxylic acid ethyl ester in 150 ml MeOH was cooled to room temperature and treated in portion with 3.03 g (80 mmol) of NaBH4. After 3 h the reaction was adjusted to pH 4 with AcOH, evaporated and treated with aqueous saturated NaHCO$_3$/EtOAc (3×). The organic phase was dried (Na$_2$SO$_4$) and evaporated to give 29.3 g (quant.) of 1:1 mixture of (3RS,4RS)- and (3RS,4SR)-4-hydroxy-1-(naphthalene-2-sulfonyl)-piperidine-3-carboxylic acid ethyl ester, MS: 364 (MH$^+$).

In analogy: 4-Hydroxy-1-methanesulfonyl-1,2,5,6-tetrahydro-pyridine-3-carboxylic acid ethyl ester gave a 1:1 mixture of (3RS,4RS)- and (3RS,4SR)-4-hydroxy-1-methanesulfonyl-piperidine-3-carboxylic acid ethyl ester which was immediately used for the next reaction.

A solution of 23.8 g (65 mmol) 1:1 mixture of (3RS,4RS)- and (3RS,4SR)-4-hydroxy-1-(naphthalene-2-sulfonyl)-piperidine-3-carboxylic acid ethyl ester in 400 ml CH$_2$Cl$_2$ was treated at 0° C. with 5.56 ml (71.5 mmol) methanesulfonyl chloride, 7.85 ml (97.5 mmol) pyridine and 7.94 g (65 mmol) DMAP. The reaction was stirred 24 h at room temperature and partitioned between aqueous 1 N HCl/Et$_2$O (3×). The organic phases were washed with aqueous 10% NaCl solution, dried over Na$_2$SO$_4$ and evaporated to give 28.75 g (quantitative) of a 1:1 mixture of (3RS,4RS)- and (3RS,4SR) 4-methanesulfonyloxy-1-(naphthalene-2-sulfonyl)-piperidine-3-carboxylic acid ethyl ester.

2.76 ml (17.83 mmol) of 4-methoxybenzyl mercaptan was slowly added at room temperature to a solution of 1.83 g (16.35 mmol) of potassium tert-butylate in 60 ml DMF and stirred mechanically for 20 min. Then 6.56 g (14.86 mmol) of a 1:1 mixture of (3RS,4RS)- and (3RS,4SR) 4-methanesulfonyloxy-1-(naphthalene-2-sulfonyl)-piperidine-3-carboxylic acid ethyl ester in 60 ml DMF were slowly added at 20° C. The reaction was stirred for 45 min at room temperature, and partitioned between cooled saturated aqueous NH$_4$Cl/EtOAc (3×300). The organic phases were washed with aqueous 10% NaCl, dried (Na$_2$SO$_4$) and evaporated. Flash chromatography on silica gel (toluene/CH$_3$CN 97.5:2.5 to 95:5) gave 4.00 g (54%) of 1:1 mixture of (3RS,4RS)- and (3RS,4SR)-4-(4-methoxy-benzylsulfanyl)-1-(naphthalene-2-sulfonyl)-piperidine-3-carboxylic acid ethyl ester, MS: 500 (MH$^+$).

In analogy: A 1:1 mixture of (3RS,4RS)- and (3RS,4SR)-4-hydroxy-1-methanesulfonyl-piperidine-3-carboxylic acid ethyl ester gave via a 1:1 mixture of (3RS,4RS)- and (3RS,4SR)-1-methanesulfonyl-4-methanesulfonyloxy-piperidine-3-carboxylic acid ethyl ester a 1:1 mixture of (3RS,4RS)- and (3RS,4SR)-1-methanesulfonyl-4-(4-methoxy-benzylsulfanyl)-piperidine-3-carboxylic acid ethyl ester, MS: 388 (MH$^+$).

1.2 ml (1.2 mmol, IM THF solution) of LAH was added during 5 min to a cold solution (−20° C.) of 500 mg (1.2 mmol) in 10 ml THF. The reaction was stirred for 20 min, cooled to −78° C. and quenched with a suspension of 0.3 g silica gel/0.3 g MgSO$_4$.7H$_2$O in 2 ml aqueous 10% KHSO$_4$. After the addition of 0.5 ml H$_2$O, the suspension was stirred for 10 min at room temperature, filtered and washed with THF. After evaporation of the THF, the residue was taken up in CH$_2$Cl$_2$, dried over Na$_2$SO$_4$, evaporated and oile out of Et$_2$O/pentane to give 430 mg (94%) of 1:1 mixture of (3RS,4RS)- and (3RS,4SR)-[4-(4-methoxy-benzylsulfanyl)-1-(naphthalene-2-sulfonyl)-piperidin-3-yl]-methanol, MS: 458 (MH$^+$).

In analogy: 1:1 Mixture of (3RS,4RS)- and (3RS,4SR)-1-methanesulfonyl-4-(4-methoxy-benzylsulfanyl)-piperidine-3-carboxylic acid ethyl ester gave a 1:1 mixture of (3RS,4RS)- and (3RS,4SR)-[1-methanesulfonyl-4-(4-methoxy-benzylsulfanyl)-piperidin-3-yl]-methanol, MS: 345 (M).

150 mg (0.3 mmol) of (3RS,4RS)- and (3RS,4SR)-[4-(4-methoxy-benzylsulfanyl)-1-(naphthalene-2-sulfonyl)-piperidin-3-yl]-methanol and 0.039 ml (0.33 mmol) of benzylbromide were dissolved in 15 ml DMF, cooled to 0° C. and treated with 14.4 mg (0.33 mmol) of 55% NaH and a catalytic amount of NaI. The reaction was warmed up over night and treated with saturated NH$_4$Cl solution/EtOAc (3×). The organic phase was washed with 10% NaCl solution, dried over Na$_2$SO$_4$ and evaporated. Flash-chromatography on silica gel (toluene/CH$_3$CN 98:2) gave 90 mg (20%) of (3SR,4RS)-3-benzyloxymethyl-4-(4-methoxy-benzylsulfanyl)-1-(naphthalene-2-sulfonyl)-piperidine (proven by $^1$H-NMR, NOE), MS: 548 (MH$^+$) and 77 mg (17%) of (3SR,4SR)-3-benzyloxymethyl-4-(4-methoxy-benzylsulfanyl)-1-(naphthalene-2-sulfonyl)-piperidine (profane by $^1$H-NMR, NOE), MS: 548 (MH$^+$) and 110 mg (24%) of a 1:1 mixture of both diastereomers.

In analogy: 1:1 Mixture of (3RS,4RS)- and (3RS,4SR)-[1-methanesulfonyl-4-(4-methoxy-benzylsulfanyl)-piperidin-3-yl]-methanol gave (3RS,4RS)-3-Benzyloxymethyl-1-methanesulfonyl-4-(4-methoxy-benzylsulfanyl)-piperidine, MS: 435 (M) and (3RS,4SR)-3-benzyloxymethyl-1-methanesulfonyl-4-(4-methoxy-benzylsulfanyl)-piperidine, MS: 435 (M).

Method 1: 84 mg (0.153 mmol) (3SR,4RS)-3-Benzyloxymethyl-4-(4-methoxy-benzylsulfanyl)-1-(naphthalene-2-sulfonyl)-piperidine were dissolved in 2 ml TFA and treated at 0° C. with 0.244 ml (1.53 mmol) of triethylsilane. After 2 h at 0° C. and 18 h at room temperature, the mixture was evaporated and purified by precipitation with Et$_2$O/pentane to give 40 mg (61%) of (3SR,4RS)-3-benzyloxymethyl-1-(naphthalene-2-sulfonyl)-piperidine-4-thiol, MS: 427 (M).

In analogy: (3SR,4SR)-3-Benzyloxymethyl-4-(4-rmethoxy-benzylsulfanyl)-1-(naphthalene-2-sulfonyl)-piperidine gave (3SR,4SR)-3-benzyloxymethyl-1-(naphthalene-2-sulfonyl)-piperidine-4-thiol, MS: 428 (MH$^+$).

(3RS,4RS)-3-Benzyloxymethyl-1-methanesulfonyl-4-(4-methoxy-benzylsulfanyl)-piperidine gave (3RS,4RS)-3-benzyloxymethyl-1-methanesulfonyl-piperidine-4-thiol, MS: 316 (MH$^+$).

(3RS,4SR)-3-Benzyloxymethyl-1-methanesulfonyl-4-(4-methoxy-benzylsulfanyl)-piperidine gave (3RS,4SR)-3-benzyloxymethyl-1-methanesulfonyl-piperidine-4-thiol, MS: 316 (MH$^+$).

Example 20
Synthesis of Tert. Thiols

Oxo-pyrrolidine-1,2-dicarboxylic acid 1-tert-butyl ester wrere prepared from BOC-Hyp-OH following literature procedure [Baldwin, Jack E.; Field, Robert A.; Lawrence, Christopher C.; Merritt, Kristen D.; Schofield, Christopher J.; Tetrahedron Lett.; 34; 1993; 7489–7492; and Herdewijn, Piet; Claes, Paul J.; Vanderhaeghe, Hubert; Can.J.Chem.; 60; 1982; 2903–2907;]

To a solution of methylenetriphenyl phosphorane, previously prepared from 37 g (777 mmol, 50% NaH in mineral oil, 4 eq) and 277.6 g (777 mmol, 4 eq) methyltriphenyl-phosphonium bromide in 1.5 l THF by stirring at 50° C. for 4 h, were added 44.5 g (194 mmol, leq) (2S)-4-Oxo-pyrrolidine-1,2-dicarboxylic acid 1-tert-butyl ester in 300 ml over a period of 30 min at RT. The suspension was stirred at 50° C. over night. After cooling to RT the suspension was added to a 5% NaHCO$_3$ solution, washed with ether, the inorganic phase was acidified and extracted with EtOAc, washed with brine, dried over Na$_2$SO$_4$ and evaporated. 32.1 g (72%) (2S)-4-Methylene-pyrrolidine-1,2-dicarboxylic acid 1-tert-butyl ester were isolated as white solid.

To 14.7 g (64.7 mmol) (2S)-4-Methylene-pyrrolidine-1, 2-dicarboxylic acid 1-tert-butyl ester in 80 ml THF were added 7.13 ml (64.7 mmol, 1.0 eq) N-methylmorpholine and 8.5 ml (64.0 mmol, 1.0 eq) isobutylchloro formate at −5° C. and the solution was stirred at that temperature for 1.5 h. The mixture was filtered and added to a suspension of 3.7 g (97.8 mmol, 1.5 eq) NaBH$_4$ in 30 ml water over a period of 25 min at 0° C. The reaction was stirred at 0° C. for 2 h and at RT over night. Ether was added, the layers were separated and the inorganic layer was extracted with ether and CH$_2$Cl$_2$, the organic layers were washed with brine, dried over Na$_2$SO$_4$, filtered and evaporated, yielding 9.3 g (68%) (2S)-2-Hydroxymethyl-4-methylene-pyrrolidine-1-carboxylic acid tert-butyl ester as light brown oil, MS: 182 (M-CH$_2$OH.).

To 9.6 g (45 mmol) (2S)-2-Hydroxymethyl-4-methylene-pyrrolidine-1-carboxylic acid tert-butyl ester and 25 g (112.5 mmol, 2.5 eq) 2,4,5-trifluorobenzyl bromide in 950 ml THF were added 3.2 g (73.1 mmol, 50% in mineral oil, 1.6 eq) NaH at 0° C. over a period of 30 min. The reaction was warmed to RT over night, and added to a cooled mixture of saturated aqueous NH$_4$Cl solution and EtOAc, the phases were separated and the inorganic one was extracted with EtOAc, the combined organic ones were washed with brine, dried over Na$_2$SO$_4$, filtered and evaporated. The crude product was purified by flash chromatography using hexane/EtOAc 4:1 as an eluent yielding 5.4 g (34%) (2S)-4-Methylene-2-(2,4,5-trifluoro-benzyloxymethyl)-pyrrolidine-1-carboxylic acid tert-butyl ester as yellow oil, MS: 358 (MH$^+$) and 1.7 g (13%) recovered starting material.

To 3.7 g (10.4 mmol) (2S)-4-Methylene-2-(2,4,5-trifluoro-benzyloxymethyl)-pyrrolidine-1-carboxylic acid tert-butyl ester in 160 ml CH$_2$Cl$_2$ were added 5.1 g (20.8 mmol, 2 eq) 3-chloroperoxybenzoic acid. The mixture was stirred at RT over night, Na$_2$S$_2$O$_3$ solution was added and the reaction was stirred for 1.5 h. The phases were separated and the inorganic one was extracted with ether. The organic phases were washed with 1M NaOH and brine, dried over Na$_2$SO$_4$, filtered and evaporated yielding 3.9 g crude product as a mixture of (3R,6S)- and (3S,6S)-6-(2,4,5-trifluoro-benzyloxymethyl)-1-oxa-5-aza-spiro[2.4]heptane-5-carboxylic acid tert-butyl, MS: 374 (MH$^+$).

g (10.4 mmol) crude mixture of (3R,6S)- and (3S,6S)-6-(2,4,5-trifluoro-benzyloxymethyl)-1-oxa-5-aza-spiro [2.4] heptane-5-carboxylic acid tert-butyl were dissolved in 20 ml EtOH and were treated with 2.07 g (20.8 mmol, 2 eq) potassium rhodamide in 2 ml H$_2$O for 16 h at RT. The mixture was concentrated, redissolved in EtOAc and washed with brine, dried over Na$_2$SO$_4$, filtered and evaporated. The crude material was purified by flash chromatography yielding 1.84 g (45%,2 steps) a mixture of (3R,6S)- and (3S,6S)-6-(2,4,5-trifluoro-benzyloxymethyl)-1-thia-5-aza-spiro[2.4]heptane-5-carboxylic acid tert-butyl ester in the ratio 5:1, MS: 390 (MH$^+$).

To 70 mg (0.18 mmol) (major diastereomer) in 3 ml THF were added 1.08 ml (1.08 mmol, 10 eq) 1M lithium triethylborohydride in THF. After 1 h the reaction was stopped by the addition of saturated aqueous NH$_4$Cl solution and the temperature was raised to RT. The mixture was extracted with EtOAc, the organic phases were washed with brine, dried over Na$_2$SO$_4$, filtered and concentrated.

The material was dissolved in 5.7 ml trifluoro ethanol and 3.8 ml CH$_2$Cl$_2$ and treated with 44,3 µl (0.17 mmol) tri-n-butyl phosphine and 19 µl H$_2$O at 0° C. The solution was stirred for 45 min, concentrated and purified by flash chromatography with hexane/EtOAc 4:1 yielding 23 mg (33%, 2 steps) (2S,4R)-4-Mercapto-4-methyl-2-(2,4,5-trifluoro-benzyloxymethyl)-pyrrolidine-1-carboxylic acid tert-butyl ester as yellow oil, MS: 392 (MH$^+$).

Analogously, the following compound was prepared from the minor diastereomer: (2S,4S)-4-Mercapto-4-methyl-2-(2,4,5-trifluoro-benzyloxymethyl)-pyrrolidine-1-carboxylic acid tert-butyl ester colorless oil, MS: 392 (MH$^+$).

Example 21.a
S-Acetyl and Benzoyl-Compounds

A solution of 10 g (21.96 mmol) (2S,4R)-4-Mercapto-2-(2,4,5-trifluoro-benzyloxymethyl)-pyrrolidine-1-carboxylic acid 2,3-dihydro-benzo [1,4]dioxin-5-yl ester in 130 ml pyridine were treated at 0° C. with 3.12 ml (43.92 mmol) acetyl chloride and stirred for 6 h at RT. The reaction was poured on ice water and extracted wit Et$_2$O (3×). The organic phases were washed with aqueous 1 N HCl and 10% NaCl, dried (Na$_2$SO4) and evaporated. Flash chromatography on silica gel (CH$_2$Cl$_2$/Et$_2$O 99.5:0.5 to 98:2) gave 9.94 g (91%) (2S,4R)-4-Acetylsulfanyl-2-(2,4,5-trifluoro-benzyloxymethyl)-pyrrolidin-1-carboxylic acid 2,3-dihydro-benzo[1,4]dioxin-5-yl ester, MS: 498 (MH$^+$).

In analogy: (3R,5S)-5-Benzyloxymethyl-1-methanesulfonyl-pyrrolidine-3-thiol gave Thioacetic acid (3R,5S)—S-(5-benzyloxymethyl-1-methanesulfonyl-pyrrolidin-3-yl) ester, mp: 79–80° C.; MS: 344 (MH$^+$);

(3R,5S)-1-Methanesulfonyl-5-(2,4,5-trifluoro-benzyloxymethyl)-pyrrolidine-3-thiol gave Thioacetic acid (3R,5S)—S-[1-methanesulfonyl-5-(2,4,5-trifluoro-benzyloxymethyl)-pyrrolidin-3-yl] ester, MS: 398 (MH$^+$);

(2S,4R)-4-Mercapto-2-(2,4,5-trifluoro-benzyloxymethyl)-pyrrolidine-1-carboxylic acid 2-methoxycarbonyl-phenyl ester gave (2S,4R)-4-Acetylsulfanyl-2-(2,4,5-trifluoro-benzyloxymethyl)-pyrrolidine-1-carboxylic acid 2-methoxycarbonyl-phenyl ester, MS: 498 (MH$^+$);

4-Mercapto-2-(2,4,5-trifluoro-benzyloxymethyl)-pyrrolidine-1-sulfonic acid butylamide gave (3R,5S)-

Thioacetic acid S-[1-butylsulfamoyl-5-(2,4,5-trifluoro-benzyloxymethyl)-pyrrolidin-3-yl] ester, MS: 455 (MH⁺);

(2S,4R)-1-[4-Mercapto-2-(2,4,5-trifluoro-benzyloxymethyl)-pyrrolidin-1-yl]-3-methyl-butan-1-one gave (5S,3R)-Thioacetic acid S-[1-(3-methyl-butyryl)-5-(2,4,5-trifluoro-benzyloxymethyl)-pyrrolidin-3-yl] ester, MS: 404 (MH⁺);

(2S,4R)-4-Mercapto-2-(2,4,5-trifluoro-benzyloxymethyl)-pyrrolidine-1-carboxylic acid 2,3-dihydro-benzo[1,4]dioxin-5-yl ester and benzoyl chloride gave (2S,4R)-4-Benzoylsulfanyl-2-(2,4,5-trifluoro-benzyloxymethyl)-pyrrolidine-1-carboxylic acid 2,3-dihydro-benzo[1,4]dioxin-5-yl, MS: 560 (MH⁺).

Example 21.b
S-Acetyl and Benzoyl-Compounds 534.1 mg (0.889 mmol) (2S,4R)-2-[(2,5-difluoro-benzylamino)-methyl]-4-tritylsulfanyl-pyrrolidine-1-carboxylic acid tert-butyl ester in 15 ml CH₂Cl₂ were treated with 180 µl (1.08 mmol, 1.27 eq) iPr₂NEt and 80 µl (1.08 mmol, 1.2 eq) acetylchloride at 0° C. 70 mg (0.11 mmol, 0.12 eq) 4-(N-benzyl-N-methylamino) pyridine, polymer-supported, were added, and the mixture was shaken for 1 h, before 220 mg (2.0 mmol/g, 0.44 mmol) polystyrene-divinylbenzene-supported tris(2-aminoethyl)amine [synthesized according to: Polymer-Supported Quenching Reagents for Parallel Purification. Booth, R. John; Hodges, John C, J. Am. Chem. Soc. (1997), 119(21), 4882–4886.] were added.

After 1 h 700 µl (8.9 mmol, 10 eq) TFA were added carefully to the mixture, followed by additional 700 µl (8.9 mmol, 10 eq) TFA after 1 h, the reaction mixture was shaken for 3 h, and treated carefully with 3.3 ml (20 mmol) iPr₂NEt, followed by 70 mg (0.11 mmol, 0.12 eq) 4-(N-benzyl-N-methylamino)pyridine, polymer-supported, and 150 µl (1.16 mmol, 1.3 eq) n-butyl chloro formate. After 45 min the mixture was filtered and the resin was washed thoroughly. To the organic phase was added saturated NaHCO₃ solution, the layers were separated, and the inorganic one was extracted with CH₂Cl₂, the organic phases were washed with brine, dried over Na₂SO₄ and evaporated. Purification by flash chromatography EtOAc/hexane 1:3 yielded 330 mg (57%, 3 steps) [2S,4R]-2-{[acetyl-(2,5-difluoro-benzyl)-amino]-methyl}-4-tritylsulfanyl-pyrrolidine-1-carboxylic acid butyl ester as light yellow oil which was dissolved in 10 ml CH₂Cl₂ and treated with 400 µl (5.2 mmol, 10 eq) TFA and 1.1 ml (5.2 mmol, 10 eq) triisopropyl silane for 30 min at 0° C. and 1 h at RT. The solution was added to a saturated solution of NaHCO₃, and the inorganic phase was extracted with CH₂Cl₂, the organic phase was washed with brine, and dried over Na₂SO₄. Column chromatography with EtOAc/hexane 1:1 yielded 156.5 mg (75%) [2S,4R]-2-{[acetyl-(2,5-difluoro-benzyl)-amino]-methyl}-4-mercapto-pyrrolidine-1-carboxylic acid butyl ester as light yellow oil, MS: 401 (MH⁺).

Analogously, the following compound was prepared from (2S,4R)-2-[(2,5-difluoro-benzylamino)-methyl]-4-tritylsulfanyl-pyrrolidine-1-carboxylic acid tert-butyl ester and benzyl chloro formate:

(2S,4R)-2-[[benzyloxycarbonyl-(2,5-difluoro-benzyl)-amino]-methyl]-4-mercapto-pyrrolidine-1-carboxylic acid butyl ester as colorless oil, MS: 493 (MH⁺), via (2S,4R)-2-[[benzyloxycarbonyl-(2,5-difluoro-benzyl)-amino]-methyl]-4-tritylsulfanyl-pyrrolidine-1-carboxylic acid tert-butyl ester as colorless oil MS: 735 (MH⁺).

130 mg (0.325 mmol) [2S,4R]-2-{[acetyl-(2,5-difluoro-benzyl)-amino]-methyl}-4-mercapto-pyrrolidine-1-carboxylic acid butyl ester in 3 ml pyridine were treated with 120 µl (1.68 mmol, 5.1 eq) acetyl chloride at 0° C. The resulting suspension was diluted with 8 ml CH₂Cl₂, and the mixture was stirred at RT over night, concentrated in vacuo and the oil was redissolved in EtOAc/1M HCl. The inorganic phase was extracted with CH₂Cl₂ and the organic phases were washed with 1M HCl and brine, dried over Na₂SO₄. The crude product was purified by flash column chromatography with EtOAc/hexane 1:1 as eluent yielding 118.2 mg (82%) [2S,4R]-2-{[acetyl-(2,5-difluoro-benzyl)-amino]-methyl}-4-acetylsulfanyl-pyrrolidine-1-carboxylic acid butyl ester as light yellow oil, MS: 443 (MHf).

Analogously, the following compounds were prepared from (2S,4R)-2-{[benzyloxy-carbonyl-(2,5-difluoro-benzyl)-amino]-methyl}-4-mercapto-pyrrolidine-1-carboxylic acid butyl ester with acetyl chloride or benzoyl chloride:

(2S,4R)-4-acetylsulfanyl-2-{[benzyloxycarbonyl-(2,5-difluoro-benzyl)-amino]-methyl}-pyrrolidine-1-carboxylic acid butyl ester as colorless oil, MS: 535 (MH⁺).

(2S,4R)-4-benzoylsulfanyl-2-{[benzyloxycarbonyl-(2,5-difluoro-benzyl)-amino]-methyl}-pyrrolidine-1-carboxylic acid butyl ester as colorless oil, MS: 597 (MH⁺).

50 mg (0.09 mmol) (2S,4R)-4-acetylsulfanyl-2-{[benzyloxycarbonyl-(2,5-difluoro-benzyl)-amino]-methyl}-pyrrolidine-1-carboxylic acid butyl ester were dissolved in 130 µl 33%HBr in acetic acid and stirred at 0° C. for 30 min, and at RT for 1 h. The solution was diluted with ether and poured on saturated NaHCO₃ solution, carefully. The inorganic layer was extracted with EtOAc, the combined organic phases were washed with water and brine, dried over Na₂SO₄ and evaporated. Column chromatography yielded 13 mg (35%) (2S,4R)-4-acetylsulfanyl-2-[(2,5-difluoro-benzylamino)-methyl]-pyrrolidine-1-carboxylic acid butyl ester as colorless oil, MS: 401 (MH⁺).

Analogously, the following compound was prepared from (2S,4R)-4-benzoylsulfanyl-2-[[benzyloxycarbonyl-(2,5-difluoro-benzyl)-amino]-methyl]-pyrrolidine-1-carboxylic acid butyl ester and isolated as hydrobromide:

(2S,4R)-4-benzoylsulfanyl-2-[(2,5-difluoro-benzylamino)-methyl]-pyrrolidine-1-carboxylic acid butyl ester hydrobromide as light brown solid, MS: 463 (MH⁺).

Example 22a
S-Cys-Compounds (3R,5S)-1-Methanesulfonyl-5-(2,4,5-trifluoro-benzyloxymethyl)-pyrrolidine-3-thiol (100 mg, 0.28 mmol) and Boc-Cys(Npys)-OH (105 mg, 0.28 mmol) were dissolved in argon-degassed DMF (abs. 3 ml) and degassed 0.1 M phosphate buffer (pH 6.2, 2 ml) was added. The reaction mixture was magnetically stirred for 2 h under argon. Ethyl acetate (30 ml), water (20 ml) were added and the organic phase was washed with water (3×20 ml) and concentrated under reduced pressure to give a yellow oil. The oil was dissolved in 4 M HCl/1,4-dioxane (5 ml) for 0.5 h. Diethyl ether (30 ml) was added and the precipitated product was filtered, washed with diethyl ether and dried. Prep. RP-HPLC purification followed by pooling and freeze-drying of desired fractions yielded (R)-2-amino-3-[(3R,5S)-1-methanesulfonyl-5-(2,4,5-trifluoro-benzyloxymethyl)-pyrrolidin-3-yldisulfanyl]-propionic acid TFA salt (148 mg), MS: 473 (MH$^-$).1

Analogously, the following compound was prepared from (3R,5S)-5-Benzyloxy-methyl-1-methanesulfonyl-pyrrolidine-3-thiol: (R)-2-amino-3-[(3R,5S)-5-benzyloxymethyl-1-methanesulfonyl-pyrrolidin-3-yldisulfanyl]-propionic acid TFA salt, MS: 419 (MH$^-$).

Example 22b

N-Acetyl-S-Cys-Compounds (3R,5S)-1-Methanesulfonyl-5-(2,4,5-trifluoro-benzyloxymethyl)-pyrrolidine-3-thiol (100 mg, 0.28 mmol) and Ac-Cys(Npys)-OH (89 mg, 0.28 mmol) were dissolved in argon-degassed DMF (abs. 2 ml) and degassed 0.1 M phosphate buffer (pH 6.2, 2 ml) was added. The reaction mixture was magnetically stirred for 2 h under argon. Work-up as above (Example 22a) yielded (R)-2-acetylamino-3-[(3R,5S)-1-methanesulfonyl-5-(2,4,5-trifluoro-benzyloxymethyl)-pyrrolidin-3-yldisulfanyl]-propionic acid (135 mg), MS: 515 (MH$^-$).

Analogously, the following compound was prepared from (3R,5S)-5-Benzyloxymethyl-1-methanesulfonyl-pyrrolidine-3-thiol: (R)-2-acetylamino-[(3R,5S)-benzyloxymethyl-1-methanesulfonyl-pyrrolidin-3-yldisulfanyl]-propionic acid, MS: 463 (MH$^+$).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

Example D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single dosages which can be applied individually.

What is claimed is:

1. A compound selected from the group consisting of compounds of formula:

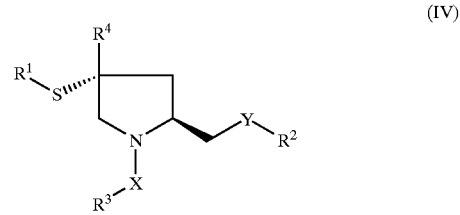

wherein $R^1$ is hydrogen, alkylcarbonyl, or arylcarbonyl;

$R^2$ is alkyl, alkenyl, alkinyl, cyanoalkyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylcarbamoyl, diarylalkyl, aryl(carboxyalkyl)amide, arylamino, arylcarbonyl, arylsulfonyl, cycloalkyl, cycloalkylcarbonyl, cycloallcylallcyl, heteroaryl, heteroarylalkyl, heterocyclylalkyl, or the group $YR^2$ is heterocyclyl or $R^2$ is a group of the formula:

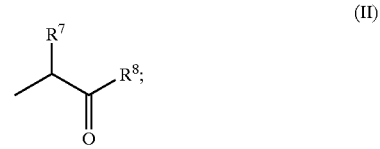

$R^3$ is alkyl, alkylcycloalkyl, alkylcycloallcylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl (alkoxycarbonyl)alkyl, heteroaryl, heteroarylalkyl, heterocyclyl or hetercycylalkyl $R^4$ is alkyl or hydrogen;

$R^7$ is hydrogen, aryl, alkyl, arylalkyl, heterocyclylalkyl, arylamino, alkyl(arylalkyl)amino, alkoxycarbonylalkyl, carboxyalkyl, or alkylthioalkyl;

$R^8$ is hydroxy, alkyl, aryl, cyanoalkyl, alkoxy, arylalkyl, arylalkoxy, mono- or dialkylamino, arylamino, aryl (alkyl)amino, cyanoalkylamino, arylalkyl(alkyl)amino, heteroaryl, heteroarylalkyl, or heterocyclyl;

X is C(O)O—;

Y is —CH², —O—, or —S—; and pharmaceutically acceptable esters, and pharmaceutically acceptable salts thereof.

2. The compound according to claim 1, wherein $R^1$ is hydrogen or alkylcarbonyl.

3. The compound according to claim 2, wherein said alkylcarbonyl is acetyl.

4. The compound according to claim 2, wherein $R^1$ is hydrogen.

5. The compound according to claim 1, wherein $R^2$ is aryl, arylalkyl, arylalkoxyalkyl, arylcarbamoyl, arylamino, arylcarbonyl, arylsulfonyl, cycloalkyl, cycloalkylcarbonyl, cycloallcylallcyl, or heteroarylalkyl.

6. The compound according to claim 5, wherein $R^2$ is aryl, arylalkyl, arylcarbamoyl, arylamino, arylcarbonyl, arylsulfonyl, or heteroarylalkyl.

7. The compound according to claim 6, wherein $R^2$ is arylalkyl.

8. The compound according to claim 7, wherein the arylalkyl of $R^2$ is phenylalkyl or phenylalkyl substituted with 2 or 3 halogen atoms.

9. The compound according to claim 1, wherein $R^3$ is alkyl, halogenalkyl, alkylcycloalkyl, alkylcycloallcylalkyl, cycloalkyl, halogenalkyl, alkoxyalkyl, alkoxycarbonylalkyl, alkinyl, aryl, arylalkyl, arlyalkyl(alkoxycarbonyl)alkyl, arylcarbonylalkyl, aryloxyalkyl, arylalkenyl, aryl(alkoxycarbonyl)alkyl, heteroaryl, heteroarylalkyl, or heterocyclyl.

10. The compound according to claim 9, wherein $R^3$ is alkyl, arylalkyl, arylcarbonylalkyl, aryloxylakyl, alkylcycloalkyl, alkylcycloylkylalkyl, cycloalkyl, heteroarylalkyl, or halogenalkyl.

11. The compound according to claim 10, wherein $R^3$ is alkyl, arylalkyl, aryl, aryloxyalkyl, or halogenalkyl.

12. The compound according to claim 1, wherein $R^4$ is hydrogen.

13. The compound according to claim 1, wherein $R^7$ is hydrogen or aryl.

14. The compound according to claim 1, wherein $R^8$ is hydroxy or alkoxy.

15. The compound according to claim 1, wherein Y is —O—.

16. The compound according to claim 1, wherein $R^1$ is hydrogen or alkylcarbonyl;

$R^2$ is arylalkyl that is phenylalkyl substituted with 2 or 3 halogen atoms;

$R^3$ is alkyl, aryl, arylalkyl, aryloxyalkyl, or halogenalkyl.

17. The compound according to claim 16, wherein said alkylcarbonyl of $R^1$ is acetyl, and $R^2$ is difluorobenzyl, or trifluorobenzyl.

18. The compound according to claim 1 which is (2S, 4R)-4-acetylsufanyl-2-(2,4,5-trifluoro-benzyloxymethyl)-pyrrolidine-1-carboxylic acid 2,3-dihydro-benzo[1,4]dioxin-5-yl ester.

19. The compound according to claim 1 which is (2S, 4R)-4-acetylsulfanyl-2-(2,4,5-trifluoro-benzyloxymethyl)-pyrrolidine-1-carboxylic acid 2-methoxycarbonyl-phenyl ester.

20. A pharmaceutical composition comprising a compound according to claim 1 and a pharmaceutically acceptable excipient.

21. A dimeric form of a compound of the formula:

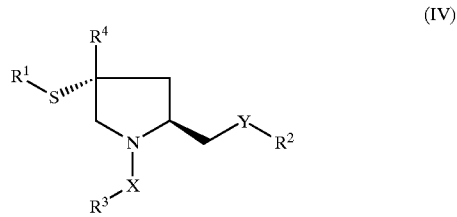

(IV)

wherein $R^1$ is hydrogen, alkylcarbonyl, or arylcarbonyl;

$R^2$ is alkyl, alkenyl, alkinyl, cyanoalkyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylcarbamoyl, diarylalkyl, aryl(carboxyalkyl)amide, arylamino, arylcarbonyl, arylsulfonyl, cycloalkyl, cycloalkylcarbonyl, cycloalkylalkyl, heteroaryl, heteroarylalkyl, heterocyclylalkyl, or the group $YR^2$ is heterocyclyl or $R^2$ is a group of the formula:

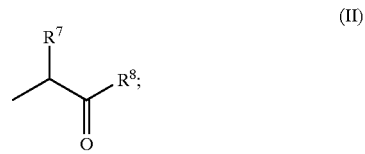

(II)

$R^3$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl(alkoxycarbonyl)alkyl, heteroaryl, heteroarylalkyl, heterocyclyl or heterocycylalkyl;

$R^4$ is alkyl or hydrogen;

$R^7$ is hydrogen, aryl, alkyl, arylalkyl, heterocyclylalkyl, arylamino, alkyl(arylalkyl)amino, alkoxycarbonylalkyl, carboxyalkyl, or alkylthioalkyl;

$R^8$ is hydroxy, alkyl, aryl, cyanoalkyl, alkoxy, arylalkyl, arylalkoxy, mono- or dialkylamino, arylamino, aryl(alkyl)amino, cyanoalkylamino, arylalkyl(alkyl)amino, heteroaryl, heteroarylalkyl, or heterocyclyl;

X is C(O)O—; and

Y is —CH², —O—, or —S—.

22. The compound according to claim 1 which is (2S, 4R)-4-mercapto-2-(2,4,5-trifluoro-benzyloxymethyl)-pyrrolidine-1-carboxylic acid 2,3-dihydro-benzo[1,4]dioxin-5-yl ester.

23. The compound according to claim 1 which is (2S, 4R)-4-mercapto-2-(2,4,5-trifluoro-benzyloxymethyl)-pyrrolidine-1 -carboxylic acid 2-methoxycarbonyl-phenyl ester.

* * * * *

UNITED STATES PATENT AND TRADEMARK OFFICE
CERTIFICATE OF CORRECTION

PATENT NO. : 6,790,860 B2
DATED : September 14, 2004
INVENTOR(S) : Johannes Aebi et al.

It is certified that error appears in the above-identified patent and that said Letters Patent is hereby corrected as shown below:

Column 104,
Line 43, delete "cycloalkyl, cycloalkylcarbonyl, cycloallcylallclyl," and insert
-- cycloalkyl, cycloalkylcarbonyl, cycloalkylalkyl --.

Column 105,
Line 17, delete "cycloallcylallcyl or heteroarylalkyl." and insert -- cycloalkylcarbonyl, cycloalkylalkyl, or heteroarylalkyl. --
Line 29, delete "alkyl, halogenalkyl, alkylcycloalkyl, alkylcycloallcylalkyl," and insert
-- alkyl, halogenalkyl, alkylcycloalkyl, alkylcyoalkylalkyl, --.
Line 54, delete "halogen atoms;" and insert -- halogen atoms; and --.

Signed and Sealed this

Twenty-first day of December, 2004

JON W. DUDAS
*Director of the United States Patent and Trademark Office*